(12) United States Patent
Nishimura et al.

(10) Patent No.: US 9,492,569 B2
(45) Date of Patent: Nov. 15, 2016

(54) ANTIBODIES THAT BIND INTEGRIN ALPHA-V BETA-8

(75) Inventors: Stephen Nishimura, Mill Valley, CA (US); Jianlong Lou, San Bruno, CA (US); Jody Lynn Baron, Mill Valley, CA (US); James Marks, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 119 days.

(21) Appl. No.: 14/239,124

(22) PCT Filed: Aug. 17, 2012

(86) PCT No.: PCT/US2012/051373
§ 371 (c)(1),
(2), (4) Date: May 30, 2014

(87) PCT Pub. No.: WO2013/026004
PCT Pub. Date: Feb. 21, 2013

(65) Prior Publication Data
US 2014/0271478 A1 Sep. 18, 2014

Related U.S. Application Data

(60) Provisional application No. 61/646,111, filed on May 11, 2012, provisional application No. 61/524,708, filed on Aug. 17, 2011.

(51) Int. Cl.
| | | |
|---|---|---|
| *A61K 38/00* | (2006.01) | |
| *A61K 39/00* | (2006.01) | |
| *C07K 16/18* | (2006.01) | |
| *A61K 49/00* | (2006.01) | |
| *C07K 14/705* | (2006.01) | |
| *C07K 16/28* | (2006.01) | |

(52) U.S. Cl.
CPC ......... *A61K 49/00* (2013.01); *C07K 14/70546* (2013.01); *C07K 16/2839* (2013.01); *A01K 2207/15* (2013.01); *A01K 2217/075* (2013.01); *A61K 2039/505* (2013.01); *C07K 2317/24* (2013.01); *C07K 2317/30* (2013.01); *C07K 2317/34* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,530,101 A | 6/1996 | Queen et al. | |
| 5,635,601 A | 6/1997 | Moyle et al. | |
| 7,087,405 B2 | 8/2006 | Johanson et al. | |
| 2004/0170630 A1 | 9/2004 | Huang et al. | |
| 2005/0002934 A1 | 1/2005 | Reed | |
| 2009/0324604 A1 | 12/2009 | Liu et al. | |
| 2011/0071278 A1 | 3/2011 | Kojima et al. | |

FOREIGN PATENT DOCUMENTS

| | | | |
|---|---|---|---|
| JP | 6-506115 A | | 7/1994 |
| WO | 2010/022737 A1 | | 3/2010 |
| WO | 2011/020529 A2 | | 2/2011 |
| WO | 2011/103490 A2 | | 8/2011 |
| WO | WO2011/103490 | * | 8/2011 |

OTHER PUBLICATIONS

Wikipedia, Transforming growth factor beta. https://en.wikipedia.org/wiki/Transforming_growth_factor_beta. pp. 1-10, Jan. 6, 2016.*
Hulbert et al Ulcerative colitis and autoimmunity induced by loss of myeloid αv integrins. (PNAS_Oct. 2, 2007_vol. 104_No. 40_15823-15828).*
Mamuya et al . αV integrins and TGF-β-induced EMT: a circle of regulation. J. Cell. Mol. Med. vol. 16, No. 3, 2012 pp. 445-455.*
Khan et al. Mesangial Cell Integrin αvB8 Provides Glomerular Endothelial Cell Cytoprotection by Sequestering TGF-β and Regulating PECAM-1. The American Journal of Pathology, vol. 178, No. 2, Feb. 2011).*
Worthington et al. Integrin αvβ8-Mediated TGF-β Activation by Effector Regulatory T Cells Is Essential for Suppression of T-Cell-Mediated Inflammation. Immunity; 42(5): 903-15, May 19, 2015.*
Païdassi et al. Preferential Expression of Integrin αvβ8 Promotes Generation of Regulatory T Cells by Mouse CD103+ Dendritic Cells. Gastroenterology. Nov. 2011; 141(5): 1813-1820.*
Melton et al. Expression of αvβ8 integrin on dendritic cells regulates Th17 cell development and experimental autoimmune encephalomyelitis in mice (J Clin Invest. 2010;120(12):4436-4444).*
Office Action from U.S. Appl. No. 13/580,105, dated Dec. 12, 2014.
UniProt Accession No. P26012, "ITB8_HUMAN"; Feb. 9, 2012 (4 pages).
US Biological Technical Data Sheet, No. I7661-37E1; "Integrin alphaV, beta 3 (PE)"; no date (1 page) Retrieved from the internet at usbio.net/technicalsheet.php?item=17661-37E1 (Aug. 9, 2011).
Cambier et al.; "A role for the integrin alphavbeta8 in the negative regulation of epithelial cell growth"; *Cancer Res.*; 60(24):7084-7093 (2000).
Cambier et al.; "Integrin alpha(v)beta8-mediated activation of transforming growth factor-beta by perivascular astrocytes: an angiogenic control switch"; *Am. J. Pathol.*; 166(6):1883-1894 (2005).
Fjellbirkeland et al.; "Integrin alphavbeta8-mediated activation of transforming growth factor-beta inhibits human airway epithelial proliferation in intact bronchial tissue"; *Am. J. Pathol.*; 163(2):533-542 (2003).
Neurohr et al.; "Activation of transforming growth factor-beta by the integrin alphavbeta8 delays epithelial wound closure"; *Am. J. Respir. Cell Mol. Biol.*; 35(2):252-9 (2006). Epub Mar. 30, 2006.
Nishimura, SL; "Integrin-mediated transforming growth factor-beta activation, a potential therapeutic target in fibrogenic disorders"; *Am J Pathol.*; 175(4):1362-1370 (2009). Epub Sep. 3, 2009.
International Search Report from PCT/US2011/025514, dated Aug. 31, 2011.
Supplementary European Search Report from EP 11745373 mailed Nov. 28, 2013.
Office Action from CN 201180018213.9, dated Dec. 25, 2013 (English translation only).
Partial Supplementary European Search Report from EP Application No. 12823966.2, dated Feb. 20, 2015.
Office Action from U.S. Appl. No. 13/580,105, dated Apr. 8, 2015.
Office Action from CN 201180018213.9, dated Jul. 21, 2014.

(Continued)

*Primary Examiner* — Maher Haddad
(74) *Attorney, Agent, or Firm* — Kilpatrick Townsend & Stockton LLP

(57) ABSTRACT

Provided herein are antibodies with high affinity for the β8 subunit of αvβ8.

9 Claims, 16 Drawing Sheets

(56) References Cited

OTHER PUBLICATIONS

Araya et al.; "Intergrin-Mediated Transforming Growth Factor-β Activation Regulates Homeostasis of the Pulmonary Epithelial-Mesenchymal Trophic Unit"; *Am. J. Pathol.*; 169:405-415 (2006).
Mu et al.; "The integrin αvβ8 mediates epithelial homeostasis through MT1-MMP-dependent activation of TGF-β1"; *J. Cell Biol.*; 157(3):493-507.
International Search Report and Written Opinion from PCT/US2012/051373, dated Feb. 4, 2013.
Acharya M, et al., "αv Integrin expression by DCs is required for Th17 cell differentiation and development of experimental autoimmune encephalomyelitis in mice," *J Clin Invest.* 2010;120(12):4445-52.
Aluwihare P, et al., "Mice that lack activity of αvβ6- and αvβ8-integrins reproduce the abnormalities of *Tgfb1-* and *Tgfb3-*null mice," *J Cell Sci.* 2009;122(Pt 2):227-32.
Bottinger EP, et al., "TGF-β signaling in renal disease," *J Am Soc Nephrol.* 2002;13(10):2600-10.
Culhane AC, et al., "A six-gene signature predicting breast cancer lung metastasis," *Cancer Res.* 2009;69(18):7480-5.
Ganesan AP, et al., "Tumor-infiltrating regulatory T cells inhibit endogenous cytotoxic T cell responses to lung adenocarcinoma," *J Immunol.* 2013;191(4):2009-17.
Kitamura H, et al., "Mouse and human lung fibroblasts regulate dendritic cell trafficking, airway inflammation, and fibrosis through integrin αvβ8-mediated activation of TGF-β," *J Clin Invest.* 2011;121(7):2863-75.
Reyes SB, et al., "αvβ8 integrin interacts with RhoGDI1 to regulate Rac1 and Cdc42 activation and drive glioblastoma cell invasion," *Mol Biol Cell.* 2013;24(4):474-82.
Wang WW, et al., "Integrin beta-8 (ITGB8) silencing reverses gefitinib resistance of human hepatic cancer HepG2/G cell line," *Int J Clin Exp Med.* 2015;8(2):3063-71.

* cited by examiner

Framework 1     CDR1     Framework 2     CDR2     Framework 3     CDR3     Framework 4

37E1 (SEQ ID NO:4)
EVQLVESGGGLVQPGGSLMLSCAASGFVFSRYWMSWVRQAPGKGLEWIGEINPDSSTINYTSSLKDKFIISRDNAKNTLYLQMNKVRSEDTALYYCACLITTEDYWGQGTSVTVSS

37E1B5 (SEQ ID NO:6)
EVQLVESGGGLVQPGGSLMLSCAVSGFVFSRYWMSWVRQAPGKGLEWIGEINPDSSTINYTSSLKDKFIISRDNAKNTLYLQMNKVRSEDTALYYCACLITTEDYWGQGTSVTVSS

Hu37E1B5 (SEQ ID NO:8)
EVQLVESGGGLVQPGGSLRLSCAVSGFVFSRYWMSWVRQAPGKGLEWIGEINPDSSTINYTSSLKDRFTISRDNAKNSLYLQMNSLRAEDTAVYYCASLITTEDYWGQGTTVTVSS

VL

Framework 1     CDR1     Framework 2     CDR2     Framework 3     CDR3     Framework 4

37E1wt (SEQ ID NO:5)
QIVLTQSPSSMYASLGERVTIPCKASQDINSYLSWFQQKPGKSPKTLIYRANRLVDGVPSRFSGSGSGQDYSLTISSLEYEDMGIYYCLQYDEFPYTFGGGTKLEIKA

37E1B5 (SEQ ID NO:7)
QIVLTQSPSSMYASLGERVTIPCKASQDINSYLSWFQQKPGKSPKTLIYYANRLVDGVPSRFSGSGSGQDYSLTISSLEYEDMGIYYCLQYDEFPYTFGGGTKLEIKA

Hu37E1B5 (SEQ ID NO:9)
EIVLTQSPSSLSLSPGERVTITCKASQDINSYLSWYQQKPGKAPKLLIYYANRLVDGVPARFSGSGSGQDYTLTISSLEPEDFAVYYCLQYDEFPYTFGGGTKLEIKR

A:
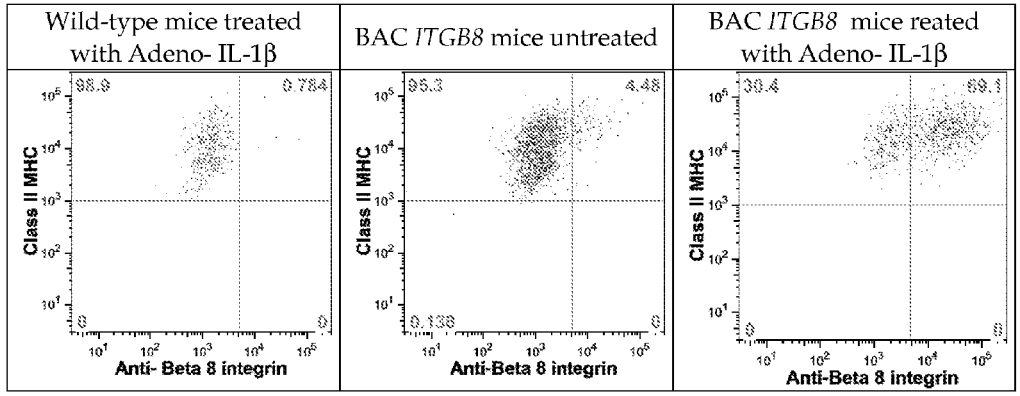
B:
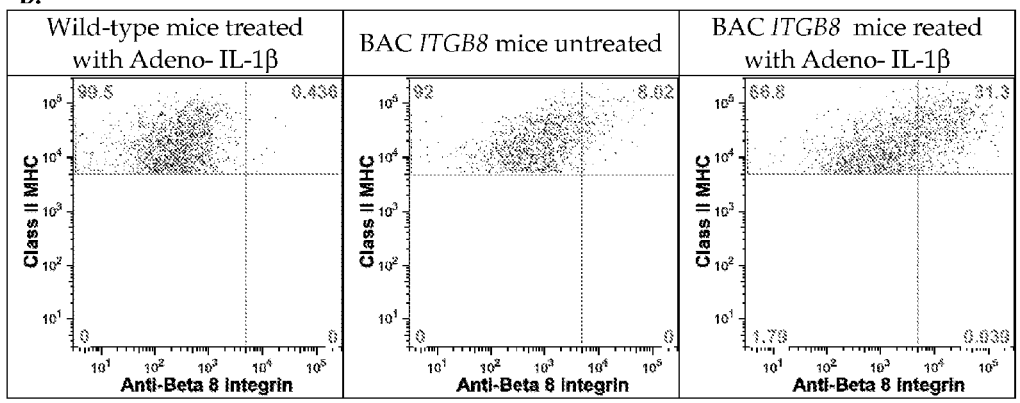
C:
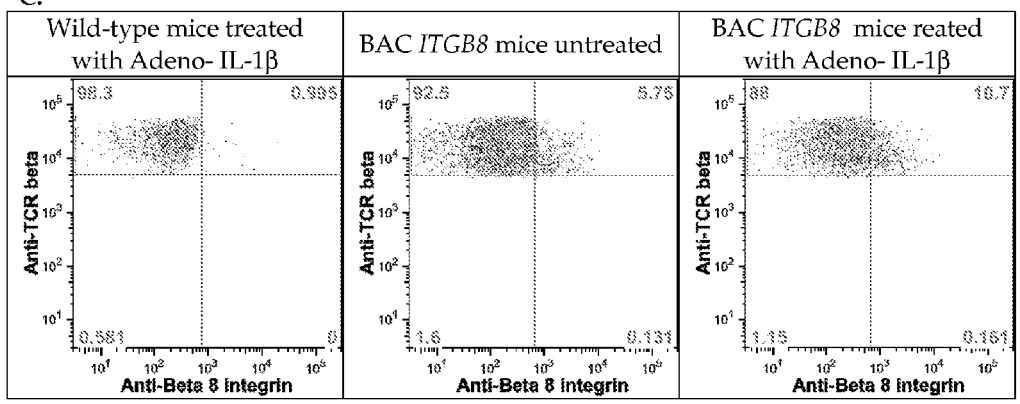
FIGURE 3

D:
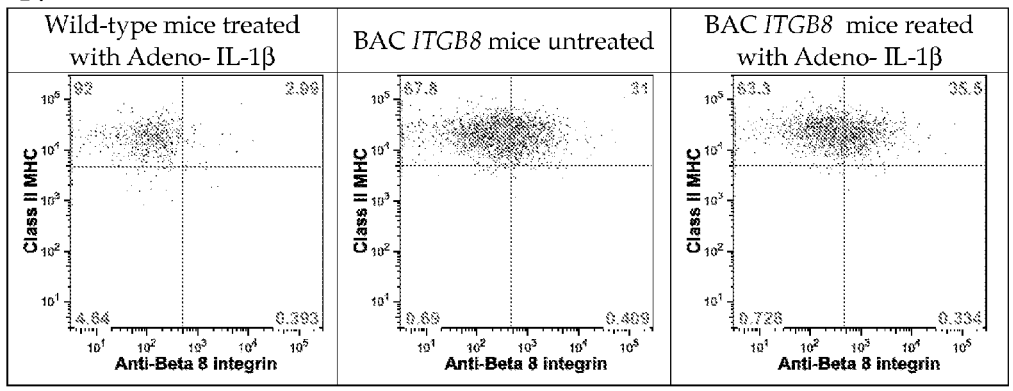
E:
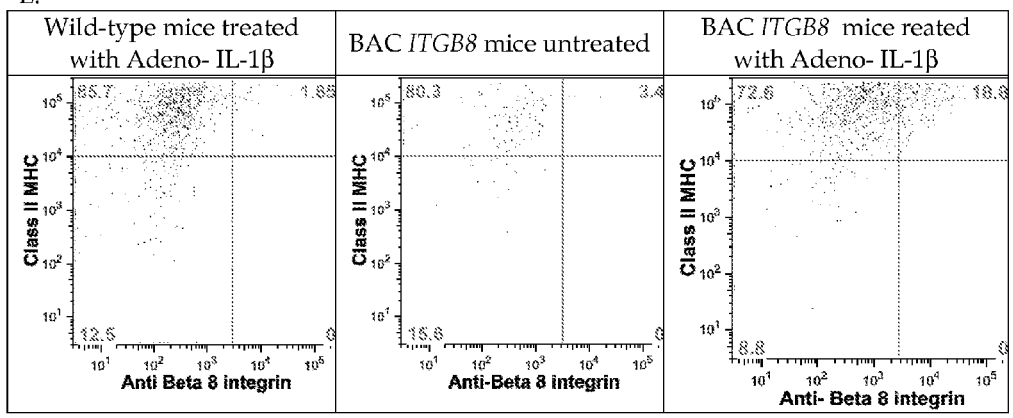
F:
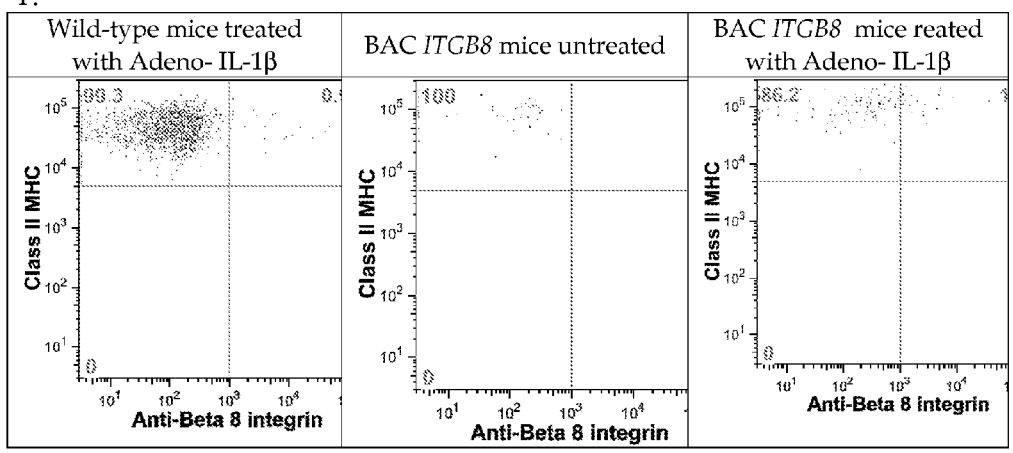
FIGURE 3 (cont.)

G: Summary Table

| Cell Populations | Lung | Liver | Lymphnodes | Spleen | Small Bowel |
|---|---|---|---|---|---|
| T cells | + |  | + | - | + |
| B cells | + |  | + | - | + |
| macrophages | + |  | + | - | + |
| Dendritic cells | + |  | + | - | + |
| Stellate cells | NA | + | NA | NA | NA |

FIGURE 3 (cont.)

VH (heavy chain)

| | | Framework 1 | CDR1 | Framework 2 | CDR2 |
|---|---|---|---|---|---|
| wt 4F1 | SEQ ID NO:20 | QVQLQQSGAELVRPGTSVKVSCKASGYAFT | NYLIE | WVKQRPGQGLEWIG | VINPGTGGTNYNKKFKV |
| wt 6B9 | SEQ ID NO:18 | QVQLQQSGAELVRPGTSVKVSCKASGYAFT | DYLIE | WVKQRPGQGLEWIG | VINPETGGTNYNAKFKG |
| 6B9Mut1 | SEQ ID NO:31 | QVQLQQSGAELVRPGTSVKVSCKASGYAFT | DYLIE | WVKQRPGQGLEWIG | VINPETGGTNYNAKFRG |
| wt 11E8 | SEQ ID NO:10 | EVQLQQSGPELMKTGASVKISCKATGYTFS | SYWIE | WVKQRPGHGLEWIG | DILPGSGTTNYNEKFKG |
| 11E8Mut28 | SEQ ID NO:32 | EVQLQQSGPELMKTGASVKISCKATGYTFS | SYWIE | WVKQRPGHGLEWIG | DILPGSGTTNYNEKFKG |
| 11E8Mut94 | SEQ ID NO:88 | EVQLQQSGPELMKTGASVKISCKATGYTFS | SYWIE | WVKQRPGHGFEWIG | DILPGSGTTNYNEKFEG |
| 11E8Mut39 | SEQ ID NO:102 | EVQLQQSGPELMKTGASVKISCKATGYTFS | TYWIE | WVKQRPGHGLEWIG | HTLPGSGTTNYNEKFKG |
| wt 14E5 | SEQ ID NO:12 | EVQLQQSGAELMKPGASVKISCKATGYTFS | TYWIE | WIKQRPGHGLEWIG | HILPGSVITNYNEKFKG |
| 14E5Mut11 | SEQ ID NO:33 | EVQLQQSGAELMKPGASVKISCKATGYTFS | TNWIE | WIKQRPGHGLEWIG | HILPGSVITNYNEKFKG |
| 14E5Mut42 | SEQ ID NO:34 | EVPLQQSGAELMKPGASVKISCKATGYTFS | TYWIE | WIKQRPGHGLEWIG | HILPGSVITNYNEKFKG |
| 14E5Mut54 | SEQ ID NO:35 | EVQLQQSGAELMKPGASVKISCKATGYTFS | TNWIE | WIKQRPGHGLEWIG | HILPGSVITNYNEKFKG |
| 14E5Mut68 | SEQ ID NO:36 | EVQLQQSGAELMKPGASVKISCKATGYTFS | TYWIE | WIKQRPGHGLEWIG | DILPGSGTTNYNEKFKG |
| 14E5Mut65 | SEQ ID NO:37 | QVQLQQSGAELMKPGASVKISCKATGYSFS | TNWIE | WIKQRPGHGLEWIG | DILPGSVITNYNEKFKG |
| 14E5Mut83 | SEQ ID NO:38 | EVQLQQSGAVLMKPGASVKISCKATGYTFS | THWIE | WIKQRPGHGLEWIG | HILPGSVITNYNEKFKG |
| 14E5Mut93 | SEQ ID NO:135 | EVQLQQSGAELMKPGSSVKISCKATGYTFS | TYWIE | WIKQRPGHGLEWIG | HILPGSVITNYNEKFKG |
| 14E5Mut95 | SEQ ID NO:39 | EVQLQQTGAELMKPGASVKISCKATGYTFS | TYWIE | WIKQRPGHGLEWIG | HILPGSVITNYNEKFKG |

FIGURE 11A

VH (heavy chain)

| | | Framework 3 | CDR3 | Framework 4 |
|---|---|---|---|---|
| wt 4F1 | SEQ ID NO:20 | KATLTADKSSSTAYMQLGGLTFDDSAVYFCAR | EGNARTYYYAMDY | WGQGTSVTVSS |
| wt 6B9 | SEQ ID NO:18 | KATLTADKSSSSAYMQLSSLTSGDSAVYFCAR | EAGNYIYAMDY | WGQGTSVTVSS |
| 6B9Mut1 | SEQ ID NO:31 | KATLTADKSSSSAYMQLSSLTSGDSAVYFCAR | EAGNYIYAMDY | WGQGTSVTVSS |
| wt 11E8 | SEQ ID NO:10 | RATVTADRSSNTAYMQLSSLTYGDSAVYYCAT | WGWDTY | WDQGTSVTVSS |
| 11E8Mut28 | SEQ ID NO:32 | KAAITADTSSNTSYLQLSSLTSEDSAVYYCAR | WGWDSY | WGQGTLVTVSS |
| 11E8Mut94 | SEQ ID NO:88 | RAAITADTSSNTSYMQLSSLTSEDSAVYYCAR | WGWDSY | WGQGTLVTVSS |
| 11E8Mut39 | SEQ ID NO:102 | RATITADRPSNTSYMQLSSLTYGDSAVFYCAT | WGWDTY | WDHGTSVTVSS |
| wt 14E5 | SEQ ID NO:12 | KAAITADTSSNTSYMQLSSLTSEDSAVYYCAR | WGWDSY | WGQGTLVTVSS |
| 14E5Mut11 | SEQ ID NO:33 | KAAITADTSSNTSYMQLSSLTSEDSAVYYCAR | WGWDSY | WGQGTLVTVSS |
| 14E5Mut42 | SEQ ID NO:34 | KAAITADTSSNTSYMQLSSLTSEDSAVYYCAR | WGWDSY | WGQGTLVTVSS |
| 14E5Mut54 | SEQ ID NO:35 | KAAITADTSSNTSYMQLTSLTSEDSAVYYCAR | WGWDSY | WGQGTLVTVSS |
| 14E5Mut68 | SEQ ID NO:36 | RATVTADRSSNTAYMQLSSLTSEDSAVYYCAR | WGWDSY | WGQGTLVTVSS |
| 14E5Mut65 | SEQ ID NO:37 | KAAITADTSSNTSYMQLSSLTSDDSAVYYCAR | WGWDSY | WGQGTLVTVSS |
| 14E5Mut83 | SEQ ID NO:38 | KAAITADTSSNTSYMQLSSLTSEDSAVYYCAR | WGWDSY | WGQGTLVTVSS |
| 14E5Mut93 | SEQ ID NO:135 | KAAITADTSSNTSYMQLSSLTSEDSAVYYCAR | WGWDSY | WGQGTLVTVSS |
| 14E5Mut95 | SEQ ID NO:39 | KAVITADTSSNTSYMQLSSLTSEDSAVYYCAR | WGWDSY | WGQGTLVTVSS |

FIGURE 11B

VK (light chain)

| | | Framework 1 | CDR1 | Framework 2 | CDR2 |
|---|---|---|---|---|---|
| wt 4F1 | SEQ ID NO:21 | DIEMTQTPASLSASVGETVTITC | RASENIYSYLV | WYQQKQGKSPQVLVY | NAKTLAE |
| wt 6B9 | SEQ ID NO:19 | DIQMTQSPASLSASVGETVTITC | RASVNIYSYLV | WYQQKQGKSPQLLVH | NAKTLAE |
| 6B9Mut1 | SEQ ID NO:22 | DIVMTQSPASLSASVGETVTITC | RASVNIYSYLV | WYQQKQGKSPQLLVH | NAKTLAE |
| wt 11E8 | SEQ ID NO:11 | DIVMTQSPSSLSASLGDRVTISC | SASQGISNYLN | WYQQKPDGTVKLLIY | YTSSLHS |
| 11E8Mut28 | SEQ ID NO:23 | DIVMTQSPSSLSASLGDRVTISC | SASQGISNYLN | WYQQKPDGTVKLLIY | YTSSLHS |
| 11E8Mut94 | SEQ ID NO:89 | DIKMTQTPSSLSASLGDRVTISC | SASQGISNYLN | WYQQKPDGTVKLLIY | YTSSLHS |
| 11E8Mut39 | SEQ ID NO:104 | DIEMTQSPSSLSASLGDRVTISC | STSQDVSSYLN | WYQQKPDGTVTLLIY | YASNLHS |
| wt 14E5 | SEQ ID NO:13 | DIEMTQSPSSLSASLGDRVTISC | STSQDISSSLN | WYQQKPDGTVTLLIY | YTSNLHS |
| 14E5Mut11 | SEQ ID NO:24 | DILMTQSPSSLSASLGDRVTISC | SASQGISKYLN | WYQQKPDGTVKLLIY | YTSSLHS |
| 14E5Mut42 | SEQ ID NO:25 | DIVMTQTPSSLSASLGDRVTISC | SASQGISNYLN | WYQQKPDGTVKLLIY | YTSSLHS |
| 14E5Mut54 | SEQ ID NO:26 | DIVMTQTPSSLSASLGDRVTIRC | SASQGISNYLN | WYQQKPDGTVKLLIY | YTSSLHS |
| 14E5Mut68 | SEQ ID NO:27 | DIKMTQSPSSLSASLGDRVTISC | SASQGISNYLN | WYQQKPDGTVKLLIY | YTSSLHS |
| 14E5Mut65 | SEQ ID NO:28 | DIKMTQSPSSLSASLGDRVTISC | SASQGISNYLN | WYQQKPDGTVKLLIY | YTSSLHS |
| 14E5Mut83 | SEQ ID NO:29 | DILMTQSPSSLSASLGDRVTISC | SASQGISNYLN | WYQQKPDGTVKLLIY | YTSSLHS |
| 14E5Mut93 | SEQ ID NO:136 | DIMMTQSPSSLSASLGDRVTISC | SASQGISNYLN | WYQQKPDGTVKLLIY | YTSSLHS |
| 14E5Mut95 | SEQ ID NO:30 | DIEMTQSPSSLSASLGDRVTISC | SBSQGISNYLN | WYQQKPDGTVKLLIY | YTSSLHS |

FIGURE 12A

VK (light chain)

| | | Framework 3 | CDR3 | Framework 4 |
|---|---|---|---|---|
| wt 4F1 | SEQ ID NO:21 | GVPSRFSGSGSGTQFSLKINSLQPEDFGSYYC | QHHNGTPYT | FGGGTKLEIKR |
| wt 6B9 | SEQ ID NO:19 | GVPSRFSGSGSGTQFSLKINSLQPEDFGSYYC | QHHHGTPYT | FGGGTKLEIKR |
| 6B9Mut1 | SEQ ID NO:22 | GVPSRFSGSGSGTQFSLKINSLQPEDFGSYYC | QHHHGTPYT | FGGGTKLEIKR |
| wt 11E8 | SEQ ID NO:11 | GVPSRFSGSGSGTDYSLTISNLEPEDIATYYC | QQYSNLPYT | FGGGTKLEIKR |
| 11E8Mut28 | SEQ ID NO:23 | GVPSRFSGSGSGTDYSLTISNLEPEDIATYYC | QQFSNLPYT | FGGGTKLEIKR |
| 11E8Mut94 | SEQ ID NO:89 | GVPSRFSGSGSGTDYSLTISNLEPEDIATYYC | QQYSNLPYT | FGGGTKLEIKR |
| 11E8Mut39 | SEQ ID NO:104 | GVPSRFSGSGSGTDYSLAISNLEPEDIATYYC | QQYSNLPYT | FGGGTKLEIKA |
| wt 14E5 | SEQ ID NO:13 | GVPSRFSGSGSGTDYSLTISNLEPEDIATYYC | QQYSKLPYT | FGGGTKLEIKR |
| 14E5Mut11 | SEQ ID NO:24 | GVPSRFSGSGSGTDYSLTISNLEPEDIATYYC | QQYSNLPYT | FGGGTKLEIKR |
| 14E5Mut42 | SEQ ID NO:25 | GVPSRFSGSGSGTDYSLTISNLEPEDIATYYC | QQYSDLPYT | FGGGTKLEIKR |
| 14E5Mut54 | SEQ ID NO:26 | GVPSRFSGSGSGTDYSLTISNLEPEDIATYYC | QQYSNLPYT | FGGGTKLEIKR |
| 14E5Mut68 | SEQ ID NO:27 | GVPSRFSGSGSGTDYSLTISNLEPEDIATYYC | QQYSELPYT | FGGGTKLEIKR |
| 14E5Mut65 | SEQ ID NO:28 | GVPSRFSGSGSGTDYSLTISNLEPEDIATYYC | QQFSNLPYT | FGGGTKLEIKR |
| 14E5Mut83 | SEQ ID NO:29 | GVPSRFSGGGSGTDYSLTISNLEPEDIATYYC | QQYSDLPYT | FGGGTKLEIKR |
| 14E5Mut93 | SEQ ID NO:136 | GVPSRFSGSRSGTDYSLTISNLEPEDIATYYC | QQYSNLPYT | FGGGTKLEIKR |
| 14E5Mut95 | SEQ ID NO:30 | GVPSRFSGSGSGTDYSLTISNLEPEDIATYYC | QQYSDLPYT | FGGGTKLEIKR |

FIGURE 12B

SEQUENCE LISTING

```
<160> NUMBER OF SEQ ID NOS: 136

<210> SEQ ID NO 1
<211> LENGTH: 60
<212> TYPE: PRT
<213> ORGANISM: Artificial sequence
<220> FEATURE:
<223> OTHER INFORMATION: synthetic region of human integrin beta8
      including 37E1B5 epitope, amino acids 121-180

<400> SEQUENCE: 1

Gly Glu Val Ser Ile Gln Leu Arg Pro Gly Ala Glu Ala Asn Phe Met
1               5                   10                  15

Leu Lys Val His Pro Leu Lys Lys Tyr Pro Val Asp Leu Tyr Tyr Leu
                20                  25                  30

Val Asp Val Ser Ala Ser Met His Asn Asn Ile Glu Lys Leu Asn Ser
            35                  40                  45

Val Gly Asn Asp Leu Ser Arg Lys Met Ala Phe Phe
        50                  55                  60

<210> SEQ ID NO 2
<211> LENGTH: 60
<212> TYPE: PRT
<213> ORGANISM: Artificial sequence
<220> FEATURE:
<223> OTHER INFORMATION: synthetic homologous murine region of human
      integrin beta8 including 37E1B5 epitope

<400> SEQUENCE: 2

Gly Glu Val Ser Val Gln Leu His Pro Gly Ala Glu Ala Asn Phe Met
1               5                   10                  15

Leu Lys Val Arg Pro Leu Lys Lys Tyr Pro Val Asp Leu Tyr Tyr Leu
                20                  25                  30

Val Asp Val Ser Ala Ser Met His Asn Asn Ile Glu Lys Leu Asn Ser
            35                  40                  45

Val Gly Asn Asp Leu Ser Lys Lys Met Ala Leu Tyr
        50                  55                  60

<210> SEQ ID NO 3
<211> LENGTH: 60
<212> TYPE: PRT
<213> ORGANISM: Artificial sequence
<220> FEATURE:
<223> OTHER INFORMATION: synthetic alignment sequence of human integrin
      beta8 including 37E1B5 epitope and mouse homologous region
<220> FEATURE:
<221> NAME/KEY: VARIANT
<222> LOCATION: (5)..(5)
<223> OTHER INFORMATION: Xaa = Val or Ile
```

```
<220> FEATURE:
<221> NAME/KEY: VARIANT
<222> LOCATION: (8)..(8)
<223> OTHER INFORMATION: Xaa = His or Arg
<220> FEATURE:
<221> NAME/KEY: VARIANT
<222> LOCATION: (20)..(20)
<223> OTHER INFORMATION: Xaa = Arg or His
<220> FEATURE:
<221> NAME/KEY: VARIANT
<222> LOCATION: (55)..(55)
<223> OTHER INFORMATION: Xaa = Lys or Arg
<220> FEATURE:
<221> NAME/KEY: VARIANT
<222> LOCATION: (59)..(59)
<223> OTHER INFORMATION: Xaa = Leu or Phe
<220> FEATURE:
<221> NAME/KEY: VARIANT
<222> LOCATION: (60)..(60)
<223> OTHER INFORMATION: Xaa = Tyr or Phe

<400> SEQUENCE: 3

Gly Glu Val Ser Xaa Gln Leu Xaa Pro Gly Ala Glu Ala Asn Phe Met
1               5                   10                  15

Leu Lys Val Xaa Pro Leu Lys Lys Tyr Pro Val Asp Leu Tyr Tyr Leu
            20                  25                  30

Val Asp Val Ser Ala Ser Met His Asn Asn Ile Glu Lys Leu Asn Ser
        35                  40                  45

Val Gly Asn Asp Leu Ser Xaa Lys Met Ala Xaa Xaa
    50                  55                  60

<210> SEQ ID NO 4
<211> LENGTH: 116
<212> TYPE: PRT
<213> ORGANISM: Artificial sequence
<220> FEATURE:
<223> OTHER INFORMATION: synthetic heavy chain (VH) of 37E1 monoclonal
      antibody

<400> SEQUENCE: 4

Glu Val Gln Leu Val Glu Ser Gly Gly Gly Leu Val Gln Pro Gly Gly
1               5                   10                  15

Ser Leu Asn Leu Ser Cys Ala Ala Ser Gly Phe Val Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Ser Ser Leu
    50                  55                  60

Lys Asp Lys Phe Ile Ile Ser Arg Asp Asn Ala Lys Asn Thr Leu Tyr
65                  70                  75                  80

Leu Gln Met Asn Lys Val Arg Ser Glu Asp Thr Ala Leu Tyr Tyr Cys
                85                  90                  95

Ala Cys Leu Ile Thr Thr Glu Asp Tyr Trp Gly Gln Gly Thr Ser Val
            100                 105                 110

Thr Val Ser Ser
        115

<210> SEQ ID NO 5
<211> LENGTH: 108
<212> TYPE: PRT
<213> ORGANISM: Artificial sequence
<220> FEATURE:
<223> OTHER INFORMATION: synthetic light chain (VL) of 37E1 monoclonal
      antibody
```

```
<400> SEQUENCE: 5

Gln Ile Val Leu Thr Gln Ser Pro Ser Ser Met Tyr Ala Ser Leu Gly
1               5                   10                  15

Glu Arg Val Thr Ile Pro Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Ala
            100                 105

<210> SEQ ID NO 6
<211> LENGTH: 116
<212> TYPE: PRT
<213> ORGANISM: Artificial sequence
<220> FEATURE:
<223> OTHER INFORMATION: synthetic heavy chain (VH) of 37E1B5 monoclonal
      antibody

<400> SEQUENCE: 6

Glu Val Gln Leu Val Glu Ser Gly Gly Gly Leu Val Gln Pro Gly Gly
1               5                   10                  15

Ser Leu Asn Leu Ser Cys Ala Val Ser Gly Phe Val Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Ser Ser Leu
50                  55                  60

Lys Asp Lys Phe Ile Ile Ser Arg Asp Asn Ala Lys Asn Thr Leu Tyr
65                  70                  75                  80

Leu Gln Met Asn Lys Val Arg Ser Glu Asp Thr Ala Leu Tyr Tyr Cys
                85                  90                  95

Ala Cys Leu Ile Thr Thr Glu Asp Tyr Trp Gly Gln Gly Thr Ser Val
            100                 105                 110

Thr Val Ser Ser
        115

<210> SEQ ID NO 7
<211> LENGTH: 108
<212> TYPE: PRT
<213> ORGANISM: Artificial sequence
<220> FEATURE:
<223> OTHER INFORMATION: synthetic light chain (VL) of 37E1B5 monoclonal
      antibody

<400> SEQUENCE: 7

Gln Ile Val Leu Thr Gln Ser Pro Ser Ser Met Tyr Ala Ser Leu Gly
1               5                   10                  15

Glu Arg Val Thr Ile Pro Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Tyr Ala Asn Arg Leu Val Asp Gly Val Pro Ser Arg Phe Ser Gly
```

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Ala
            100                 105

<210> SEQ ID NO 8
<211> LENGTH: 116
<212> TYPE: PRT
<213> ORGANISM: Artificial sequence
<220> FEATURE:
<223> OTHER INFORMATION: synthetic heavy chain (VH) of humanized 37E1B5
      (Hu37E1B5) monoclonal antibody

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Val Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Ser Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Leu Ile Thr Thr Glu Asp Tyr Trp Gly Gln Gly Thr Thr Val
            100                 105                 110

Thr Val Ser Ser
        115

<210> SEQ ID NO 9
<211> LENGTH: 108
<212> TYPE: PRT
<213> ORGANISM: Artificial sequence
<220> FEATURE:
<223> OTHER INFORMATION: synthetic light chain (VL) of humanized 37E1B5
      (Hu37E1B5) monoclonal antibody

<400> SEQUENCE: 9

Glu Ile Val Leu Thr Gln Ser Pro Ser Ser Leu Ser Leu Ser Pro Gly
1               5                   10                  15

Glu Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Tyr Ala Asn Arg Leu Val Asp Gly Val Pro Ala Arg Phe Ser Gly
    50                  55                  60

Ser Gly Ser Gly Gln Asp Tyr Thr Leu Thr Ile Ser Ser Leu Glu Pro
65                  70                  75                  80

Glu Asp Phe Ala Val Tyr Tyr Cys Leu Gln Tyr Asp Glu Phe Pro Tyr
                85                  90                  95

Thr Phe Gly Gly Gly Thr Lys Leu Glu Ile Lys Arg
            100                 105

-continued

```
<210> SEQ ID NO 10
<211> LENGTH: 115
<212> TYPE: PRT
<213> ORGANISM: Artificial sequence
<220> FEATURE:
<223> OTHER INFORMATION: synthetic heavy chain variable region of 11E8
      monoclonal antibody

<400> SEQUENCE: 10

Glu Val Gln Leu Gln Gln Ser Gly Pro Glu Leu Met Lys Thr Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Asp Ile Leu Pro Gly Ser Gly Thr Thr Asn Tyr Asn Glu Lys Phe
    50                  55                  60

Lys Gly Arg Ala Thr Val Thr Ala Asp Arg Ser Ser Asn Thr Ala Tyr
65                  70                  75                  80

Met Gln Leu Ser Ser Leu Thr Tyr Gly Asp Ser Ala Val Tyr Tyr Cys
                85                  90                  95

Ala Thr Trp Gly Trp Asp Thr Tyr Trp Asp Gln Gly Thr Ser Val Thr
            100                 105                 110

Val Ser Ser
        115

<210> SEQ ID NO 11
<211> LENGTH: 108
<212> TYPE: PRT
<213> ORGANISM: Artificial sequence
<220> FEATURE:
<223> OTHER INFORMATION: synthetic light chain variable region of 11E8
      monoclonal antibody

<400> SEQUENCE: 11

Asp Ile Val Met Thr Gln Ser Pro Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Asn Leu Pro Tyr
                85                  90                  95

Thr Phe Gly Gly Gly Thr Lys Leu Glu Ile Lys Arg
            100                 105

<210> SEQ ID NO 12
<211> LENGTH: 115
<212> TYPE: PRT
<213> ORGANISM: Artificial sequence
<220> FEATURE:
<223> OTHER INFORMATION: synthetic heavy chain variable region of 14E5
      monoclonal antibody

<400> SEQUENCE: 12

Glu Val Gln Leu Gln Gln Ser Gly Ala Glu Leu Met Lys Pro Gly Ala
1               5                   10                  15
```

Ser Val Lys Ile Ser Cys Lys Ala Thr Gly Tyr Thr Phe Ser Thr Tyr
            20                  25                  30

Trp Ile Glu Trp Ile Lys Gln Arg Pro Gly His Gly Leu Glu Trp Ile
        35                  40                  45

Gly His Ile Leu Pro Gly Ser Val Ile Thr Asn Tyr Asn Glu Lys Phe
    50                  55                  60

Lys Gly Lys Ala Ala Ile Thr Ala Asp Thr Ser Ser Asn Thr Ser Tyr
65                  70                  75                  80

Met Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
            100                 105                 110

Val Ser Ser
        115

<210> SEQ ID NO 13
<211> LENGTH: 108
<212> TYPE: PRT
<213> ORGANISM: Artificial sequence
<220> FEATURE:
<223> OTHER INFORMATION: synthetic light chain variable region of 14E5
      monoclonal antibody

<400> SEQUENCE: 13

Asp Ile Glu Met Thr Gln Ser Pro Ser Ser Leu Ser Ala Ser Leu Gly
1               5                   10                  15

Asp Arg Val Thr Ile Ser Cys Ser Thr Ser Gln Asp Ile Ser Ser Ser
            20                  25                  30

Leu Asn Trp Tyr Gln Gln Lys Pro Asp Gly Thr Val Thr Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 14
<211> LENGTH: 45
<212> TYPE: PRT
<213> ORGANISM: Artificial sequence
<220> FEATURE:
<223> OTHER INFORMATION: synthetic region of human integrin beta8
      including 6B9 and 4F1 epitope, amino acids 61-105

<400> SEQUENCE: 14

Leu Gly Pro Glu Cys Gly Trp Cys Val Gln Glu Asp Phe Ile Ser Gly
1               5                   10                  15

Gly Ser Arg Ser Glu Arg Cys Asp Ile Val Ser Asn Leu Ile Ser Lys
            20                  25                  30

Gly Cys Ser Val Asp Ser Ile Glu Tyr Pro Ser Val His
        35                  40                  45

<210> SEQ ID NO 15
<211> LENGTH: 45
<212> TYPE: PRT
<213> ORGANISM: Artificial sequence -continued

```
<220> FEATURE:
<223> OTHER INFORMATION: synthetic homologous murine region of human
      integrin beta8 including 6B9 and 4F1 epitope

<400> SEQUENCE: 15

Leu Gly Pro Glu Cys Gly Trp Cys Val Gln Glu Asp Phe Val Ser Gly
1               5                   10                  15

Gly Ser Gly Ser Glu Arg Cys Asp Thr Val Ser Ser Leu Ile Ser Lys
            20                  25                  30

Gly Cys Pro Val Asp Ser Ile Glu Tyr Leu Ser Val His
        35                  40                  45

<210> SEQ ID NO 16
<211> LENGTH: 45
<212> TYPE: PRT
<213> ORGANISM: Artificial sequence
<220> FEATURE:
<223> OTHER INFORMATION: synthetic alignment sequence of human integrin
      beta8 including 6B9 and 4F1 epitope and mouse homologous region
<220> FEATURE:
<221> NAME/KEY: VARIANT
<222> LOCATION: (14)..(14)
<223> OTHER INFORMATION: Xaa = Val or Ile
<220> FEATURE:
<221> NAME/KEY: VARIANT
<222> LOCATION: (19)..(19)
<223> OTHER INFORMATION: Xaa = Gly or Arg
<220> FEATURE:
<221> NAME/KEY: VARIANT
<222> LOCATION: (25)..(25)
<223> OTHER INFORMATION: Xaa = Thr or Ile
<220> FEATURE:
<221> NAME/KEY: VARIANT
<222> LOCATION: (28)..(28)
<223> OTHER INFORMATION: Xaa = Ser or Asn
<220> FEATURE:
<221> NAME/KEY: VARIANT
<222> LOCATION: (35)..(35)
<223> OTHER INFORMATION: Xaa = Pro or Ser
<220> FEATURE:
<221> NAME/KEY: VARIANT
<222> LOCATION: (42)..(42)
<223> OTHER INFORMATION: Xaa = Leu or Pro

<400> SEQUENCE: 16

Leu Gly Pro Glu Cys Gly Trp Cys Val Gln Glu Asp Phe Xaa Ser Gly
1               5                   10                  15

Gly Ser Xaa Ser Glu Arg Cys Asp Xaa Val Ser Xaa Leu Ile Ser Lys
            20                  25                  30

Gly Cys Xaa Val Asp Ser Ile Glu Tyr Xaa Ser Val His
        35                  40                  45

<210> SEQ ID NO 17
<211> LENGTH: 769
<212> TYPE: PRT
<213> ORGANISM: Homo sapiens
<220> FEATURE:
<221> NAME/KEY: MISC_FEATURE
<222> LOCATION: (1)..(769)
<223> OTHER INFORMATION: human integrin beta8 full length sequence

<400> SEQUENCE: 17

Met Cys Gly Ser Ala Leu Ala Phe Phe Thr Ala Ala Phe Val Cys Leu
1               5                   10                  15

Gln Asn Asp Arg Arg Gly Pro Ala Ser Phe Leu Trp Ala Ala Trp Val
            20                  25                  30

Phe Ser Leu Val Leu Gly Leu Gly Gln Gly Glu Asp Asn Arg Cys Ala
        35                  40                  45
```

-continued

```
Ser Ser Asn Ala Ala Ser Cys Ala Arg Cys Leu Ala Leu Gly Pro Glu
 50                  55                  60

Cys Gly Trp Cys Val Gln Glu Asp Phe Ile Ser Gly Gly Ser Arg Ser
 65                  70                  75                  80

Glu Arg Cys Asp Ile Val Ser Asn Leu Ile Ser Lys Gly Cys Ser Val
                     85                  90                  95

Asp Ser Ile Glu Tyr Pro Ser Val His Val Ile Pro Thr Glu Asn
            100                 105                 110

Glu Ile Asn Thr Gln Val Thr Pro Gly Glu Val Ser Ile Gln Leu Arg
            115                 120                 125

Pro Gly Ala Glu Ala Asn Phe Met Leu Lys Val His Pro Leu Lys Lys
    130                 135                 140

Tyr Pro Val Asp Leu Tyr Tyr Leu Val Asp Val Ser Ala Ser Met His
145                 150                 155                 160

Asn Asn Ile Glu Lys Leu Asn Ser Val Gly Asn Asp Leu Ser Arg Lys
                165                 170                 175

Met Ala Phe Phe Ser Arg Asp Phe Arg Leu Gly Phe Gly Ser Tyr Val
            180                 185                 190

Asp Lys Thr Val Ser Pro Tyr Ile Ser Ile His Pro Glu Arg Ile His
    195                 200                 205

Asn Gln Cys Ser Asp Tyr Asn Leu Asp Cys Met Pro Pro His Gly Tyr
210                 215                 220

Ile His Val Leu Ser Leu Thr Glu Asn Ile Thr Glu Phe Glu Lys Ala
225                 230                 235                 240

Val His Arg Gln Lys Ile Ser Gly Asn Ile Asp Thr Pro Glu Gly Gly
                245                 250                 255

Phe Asp Ala Met Leu Gln Ala Val Cys Glu Ser His Ile Gly Trp
            260                 265                 270

Arg Lys Glu Ala Lys Arg Leu Leu Leu Val Met Thr Asp Gln Thr Ser
    275                 280                 285

His Leu Ala Leu Asp Ser Lys Leu Ala Gly Ile Val Val Pro Asn Asp
290                 295                 300

Gly Asn Cys His Leu Lys Asn Asn Val Tyr Val Lys Ser Thr Thr Met
305                 310                 315                 320

Glu His Pro Ser Leu Gly Gln Leu Ser Glu Lys Leu Ile Asp Asn Asn
                325                 330                 335

Ile Asn Val Ile Phe Ala Val Gln Gly Lys Gln Phe His Trp Tyr Lys
            340                 345                 350

Asp Leu Leu Pro Leu Leu Pro Gly Thr Ile Ala Gly Glu Ile Glu Ser
    355                 360                 365

Lys Ala Ala Asn Leu Asn Asn Leu Val Val Glu Ala Tyr Gln Lys Leu
370                 375                 380

Ile Ser Glu Val Lys Val Gln Val Glu Asn Gln Val Gln Gly Ile Tyr
385                 390                 395                 400

Phe Asn Ile Thr Ala Ile Cys Pro Asp Gly Ser Arg Lys Pro Gly Met
                405                 410                 415

Glu Gly Cys Arg Asn Val Thr Ser Asn Asp Glu Val Leu Phe Asn Val
            420                 425                 430

Thr Val Thr Met Lys Lys Cys Asp Val Thr Gly Gly Lys Asn Tyr Ala
    435                 440                 445

Ile Ile Lys Pro Ile Gly Phe Asn Glu Thr Ala Lys Ile His Ile His
450                 455                 460
```

Arg Asn Cys Ser Cys Gln Cys Glu Asp Asn Arg Gly Pro Lys Gly Lys
465                 470                 475                 480

Cys Val Asp Glu Thr Phe Leu Asp Ser Lys Cys Phe Gln Cys Asp Glu
            485                 490                 495

Asn Lys Cys His Phe Asp Glu Asp Gln Phe Ser Ser Glu Ser Cys Lys
        500                 505                 510

Ser His Lys Asp Gln Pro Val Cys Ser Gly Arg Gly Val Cys Val Cys
    515                 520                 525

Gly Lys Cys Ser Cys His Lys Ile Lys Leu Gly Lys Val Tyr Gly Lys
530                 535                 540

Tyr Cys Glu Lys Asp Asp Phe Ser Cys Pro Tyr His His Gly Asn Leu
545                 550                 555                 560

Cys Ala Gly His Gly Glu Cys Glu Ala Gly Arg Cys Gln Cys Phe Ser
            565                 570                 575

Gly Trp Glu Gly Asp Arg Cys Gln Cys Pro Ser Ala Ala Ala Gln His
            580                 585                 590

Cys Val Asn Ser Lys Gly Gln Val Cys Ser Gly Arg Gly Thr Cys Val
        595                 600                 605

Cys Gly Arg Cys Glu Cys Thr Asp Pro Arg Ser Ile Gly Arg Phe Cys
    610                 615                 620

Glu His Cys Pro Thr Cys Tyr Thr Ala Cys Lys Glu Asn Trp Asn Cys
625                 630                 635                 640

Met Gln Cys Leu His Pro His Asn Leu Ser Gln Ala Ile Leu Asp Gln
            645                 650                 655

Cys Lys Thr Ser Cys Ala Leu Met Glu Gln Gln His Tyr Val Asp Gln
            660                 665                 670

Thr Ser Glu Cys Phe Ser Ser Pro Ser Tyr Leu Arg Ile Phe Phe Ile
        675                 680                 685

Ile Phe Ile Val Thr Phe Leu Ile Gly Leu Leu Lys Val Leu Ile Ile
    690                 695                 700

Arg Gln Val Ile Leu Gln Trp Asn Ser Asn Lys Ile Lys Ser Ser Ser
705                 710                 715                 720

Asp Tyr Arg Val Ser Ala Ser Lys Lys Asp Lys Leu Ile Leu Gln Ser
            725                 730                 735

Val Cys Thr Arg Ala Val Thr Tyr Arg Arg Glu Lys Pro Glu Glu Ile
            740                 745                 750

Lys Met Asp Ile Ser Lys Leu Asn Ala His Glu Thr Phe Arg Cys Asn
        755                 760                 765

Phe

<210> SEQ ID NO 18
<211> LENGTH: 120
<212> TYPE: PRT
<213> ORGANISM: Artificial sequence
<220> FEATURE:
<223> OTHER INFORMATION: synthetic heavy chain variable region of 6B9
      monoclonal antibody

<400> SEQUENCE: 18

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
            20                  25                  30

Leu Ile Glu Trp Val Lys Gln Arg Pro Gly Gln Gly Leu Glu Trp Ile
        35                  40                  45

```
Gly Val Ile Asn Pro Glu Thr Gly Gly Thr Asn Tyr Asn Ala Lys Phe
 50                  55                  60

Lys Gly Lys Ala Thr Leu Thr Ala Asp Lys Ser Ser Ser Ser Ala Tyr
 65                  70                  75                  80

Met Gln Leu Ser Ser Leu Thr Ser Gly Asp Ser Ala Val Tyr Phe Cys
                 85                  90                  95

Ala Arg Glu Ala Gly Asn Tyr Ile Tyr Ala Met Asp Tyr Trp Gly Gln
             100                 105                 110

Gly Thr Ser Val Thr Val Ser Ser
            115                 120

<210> SEQ ID NO 19
<211> LENGTH: 108
<212> TYPE: PRT
<213> ORGANISM: Artificial sequence
<220> FEATURE:
<223> OTHER INFORMATION: synthetic light chain variable region of 6B9
      monoclonal antibody

<400> SEQUENCE: 19

Asp Ile Gln Met Thr Gln Ser Pro Ala Ser Leu Ser Ala Ser Val Gly
 1               5                  10                  15

Glu Thr Val Thr Ile Thr Cys Arg Ala Ser Val Asn Ile Tyr Ser Tyr
                 20                  25                  30

Leu Val Trp Tyr Gln Lys Gln Gly Lys Ser Pro Gln Leu Leu Val
         35                  40                  45

His Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His His Gly Thr Pro Tyr
                 85                  90                  95

Thr Phe Gly Gly Gly Thr Lys Leu Glu Ile Lys Arg
             100                 105

<210> SEQ ID NO 20
<211> LENGTH: 122
<212> TYPE: PRT
<213> ORGANISM: Artificial sequence
<220> FEATURE:
<223> OTHER INFORMATION: synthetic heavy chain variable region of 4F1
      monoclonal antibody

<400> SEQUENCE: 20

Gln Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asn Tyr
                 20                  25                  30

Leu Ile Glu Trp Val Lys Gln Arg Pro Gly Gln Gly Leu Glu Trp Ile
         35                  40                  45

Gly Val Ile Asn Pro Gly Thr Gly Gly Thr Asn Tyr Asn Lys Lys Phe
 50                  55                  60

Lys Val Lys Ala Thr Leu Thr Ala Asp Lys Ser Ser Ser Thr Ala Tyr
 65                  70                  75                  80

Met Gln Leu Gly Gly Leu Thr Phe Asp Asp Ser Ala Val Tyr Phe Cys
                 85                  90                  95

Ala Arg Glu Gly Asn Ala Arg Thr Tyr Tyr Tyr Ala Met Asp Tyr Trp
             100                 105                 110
```

```
Gly Gln Gly Thr Ser Val Thr Val Ser Ser
        115                 120
```

<210> SEQ ID NO 21
<211> LENGTH: 108
<212> TYPE: PRT
<213> ORGANISM: Artificial sequence
<220> FEATURE:
<223> OTHER INFORMATION: synthetic light chain variable region of 4F1
      monoclonal antibody

<400> SEQUENCE: 21

```
Asp Ile Glu Met Thr Gln Thr Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Val Trp Tyr Gln Gln Lys Gln Gly Lys Ser Pro Gln Val Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Asn Gly Thr Pro Tyr
                85                  90                  95

Thr Phe Gly Gly Gly Thr Lys Leu Glu Ile Lys Arg
            100                 105
```

<210> SEQ ID NO 22
<211> LENGTH: 108
<212> TYPE: PRT
<213> ORGANISM: Artificial sequence
<220> FEATURE:
<223> OTHER INFORMATION: synthetic light chain variable region (VK) of
      6B9Mut1 monoclonal antibody

<400> SEQUENCE: 22

```
Asp Ile Val Met Thr Gln Ser Pro Ala Ser Leu Ser Ala Ser Val Gly
1               5                   10                  15

Glu Thr Val Thr Ile Thr Cys Arg Ala Ser Val Asn Ile Tyr Ser Tyr
            20                  25                  30

Leu Val Trp Tyr Gln Gln Lys Gln Gly Lys Ser Pro Gln Leu Leu Val
        35                  40                  45

His Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His His Gly Thr Pro Tyr
                85                  90                  95

Thr Phe Gly Gly Gly Thr Lys Leu Glu Ile Lys Arg
            100                 105
```

<210> SEQ ID NO 23
<211> LENGTH: 108
<212> TYPE: PRT
<213> ORGANISM: Artificial sequence
<220> FEATURE:
<223> OTHER INFORMATION: synthetic light chain variable region (VK) of
      11E8Mut28 monoclonal antibody

<400> SEQUENCE: 23

```
Asp Ile Val Met Thr Gln Ser Pro Ser Ser Leu Ser Ala Ser Leu Gly
```

```
                1               5                  10                 15
Asp Arg Val Thr Ile Ser Cys Ser Ala Ser Gln Gly Ile Ser Asn Tyr
                20                 25                 30

Leu Asn Trp Tyr Gln Gln Lys Pro Asp Gly Thr Val Lys Leu Leu Ile
            35                 40                 45

Tyr Tyr Thr Ser Ser Leu His Ser Gly Val Pro Ser Arg Phe Ser Gly
        50                 55                 60

Ser Gly Ser Gly Thr Asp Tyr Ser Leu Thr Ile Ser Asn Leu Glu Pro
65                 70                 75                 80

Glu Asp Ile Ala Thr Tyr Tyr Cys Gln Gln Phe Ser Asn Leu Pro Tyr
                85                 90                 95

Thr Phe Gly Gly Gly Thr Lys Leu Glu Ile Lys Arg
            100                105

<210> SEQ ID NO 24
<211> LENGTH: 108
<212> TYPE: PRT
<213> ORGANISM: Artificial sequence
<220> FEATURE:
<223> OTHER INFORMATION: synthetic light chain variable region (VK) of
      14E5Mut11 monoclonal antibody

<400> SEQUENCE: 24

Asp Ile Leu Met Thr Gln Ser Pro Ser Ser Leu Ser Ala Ser Leu Gly
1               5                  10                 15

Asp Arg Val Thr Ile Ser Cys Ser Ala Ser Gln Gly Ile Ser Lys Tyr
                20                 25                 30

Leu Asn Trp Tyr Gln Gln Lys Pro Asp Gly Thr Val Lys Leu Leu Ile
            35                 40                 45

Tyr Tyr Thr Ser Ser Leu His Ser Gly Val Pro Ser Arg Phe Ser Gly
        50                 55                 60

Ser Gly Ser Gly Thr Asp Tyr Ser Leu Thr Ile Ser Asn Leu Glu Pro
65                 70                 75                 80

Glu Asp Ile Ala Thr Tyr Tyr Cys Gln Gln Tyr Ser Asn Leu Pro Tyr
                85                 90                 95

Thr Phe Gly Gly Gly Thr Lys Leu Glu Ile Lys Arg
            100                105

<210> SEQ ID NO 25
<211> LENGTH: 108
<212> TYPE: PRT
<213> ORGANISM: Artificial sequence
<220> FEATURE:
<223> OTHER INFORMATION: synthetic light chain variable region (VK) of
      14E5Mut42 monoclonal antibody

<400> SEQUENCE: 25

Asp Ile Val Met Thr Gln Thr Pro Ser Ser Leu Ser Ala Ser Leu Gly
1               5                  10                 15

Asp Arg Val Thr Ile Ser Cys Ser Ala Ser Gln Gly Ile Ser Asn Tyr
                20                 25                 30

Leu Asn Trp Tyr Gln Gln Lys Pro Asp Gly Thr Val Lys Leu Leu Ile
            35                 40                 45

Tyr Tyr Thr Ser Ser Leu His Ser Gly Val Pro Ser Arg Phe Ser Gly
        50                 55                 60

Ser Gly Ser Gly Thr Asp Tyr Ser Leu Thr Ile Ser Asn Leu Glu Pro
65                 70                 75                 80

Glu Asp Ile Ala Thr Tyr Tyr Cys Gln Gln Tyr Ser Asp Leu Pro Tyr
```

```
                       85                  90                  95

Thr Phe Gly Gly Gly Thr Lys Leu Glu Ile Lys Arg
                100                 105

<210> SEQ ID NO 26
<211> LENGTH: 108
<212> TYPE: PRT
<213> ORGANISM: Artificial sequence
<220> FEATURE:
<223> OTHER INFORMATION: synthetic light chain variable region (VK) of
      14E5Mut54 monoclonal antibody

<400> SEQUENCE: 26

Asp Ile Val Met Thr Gln Thr Pro Ser Ser Leu Ser Ala Ser Leu Gly
1               5                   10                  15

Asp Arg Val Thr Ile Arg Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Asn Leu Pro Tyr
                85                  90                  95

Thr Phe Gly Gly Gly Thr Lys Leu Glu Ile Lys Arg
                100                 105

<210> SEQ ID NO 27
<211> LENGTH: 108
<212> TYPE: PRT
<213> ORGANISM: Artificial sequence
<220> FEATURE:
<223> OTHER INFORMATION: synthetic light chain variable region (VK) of
      14E5Mut68 monoclonal antibody

<400> SEQUENCE: 27

Asp Ile Lys Met Thr Gln Ser Pro Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Glu Leu Pro Tyr
                85                  90                  95

Thr Phe Gly Gly Gly Thr Lys Leu Glu Ile Lys Arg
                100                 105

<210> SEQ ID NO 28
<211> LENGTH: 108
<212> TYPE: PRT
<213> ORGANISM: Artificial sequence
<220> FEATURE:
<223> OTHER INFORMATION: synthetic light chain variable region (VK) of
      14E5Mut65 monoclonal antibody

<400> SEQUENCE: 28
```

```
Asp Ile Lys Met Thr Gln Ser Pro Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Phe Ser Asn Leu Pro Tyr
                85                  90                  95

Thr Phe Gly Gly Gly Thr Lys Leu Glu Ile Lys Arg
            100                 105
```

<210> SEQ ID NO 29
<211> LENGTH: 108
<212> TYPE: PRT
<213> ORGANISM: Artificial sequence
<220> FEATURE:
<223> OTHER INFORMATION: synthetic light chain variable region (VK) of
      14E5Mut83 monoclonal antibody

<400> SEQUENCE: 29

```
Asp Ile Leu Met Thr Gln Ser Pro Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Asp Leu Pro Tyr
                85                  90                  95

Thr Phe Gly Gly Gly Thr Lys Leu Glu Ile Lys Arg
            100                 105
```

<210> SEQ ID NO 30
<211> LENGTH: 108
<212> TYPE: PRT
<213> ORGANISM: Artificial sequence
<220> FEATURE:
<223> OTHER INFORMATION: synthetic light chain variable region (VK) of
      14E5Mut95 monoclonal antibody

<400> SEQUENCE: 30

```
Asp Ile Glu Met Thr Gln Ser Pro Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80
```

```
Glu Asp Ile Ala Thr Tyr Tyr Cys Gln Gln Tyr Ser Asp Leu Pro Tyr
                85                  90                  95

Thr Phe Gly Gly Gly Thr Lys Leu Glu Ile Lys Arg
            100                 105
```

<210> SEQ ID NO 31
<211> LENGTH: 120
<212> TYPE: PRT
<213> ORGANISM: Artificial sequence
<220> FEATURE:
<223> OTHER INFORMATION: synthetic heavy chain variable region (VH) of
      6B9Mut1 monoclonal antibody

<400> SEQUENCE: 31

```
Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asp Tyr
                20                  25                  30

Leu Ile Glu Trp Val Lys Gln Arg Pro Gly Gln Gly Leu Glu Trp Ile
            35                  40                  45

Gly Val Ile Asn Pro Glu Thr Gly Gly Thr Asn Tyr Asn Ala Lys Phe
    50                  55                  60

Arg Gly Lys Ala Thr Leu Thr Ala Asp Lys Ser Ser Ser Ser Ala Tyr
65                  70                  75                  80

Met Gln Leu Ser Ser Leu Thr Ser Gly Asp Ser Ala Val Tyr Phe Cys
                85                  90                  95

Ala Arg Glu Ala Gly Asn Tyr Ile Tyr Ala Met Asp Tyr Trp Gly Gln
            100                 105                 110

Gly Thr Ser Val Thr Val Ser Ser
        115                 120
```

<210> SEQ ID NO 32
<211> LENGTH: 115
<212> TYPE: PRT
<213> ORGANISM: Artificial sequence
<220> FEATURE:
<223> OTHER INFORMATION: synthetic heavy chain variable region (VH) of
      11E8Mut28 monoclonal antibody

<400> SEQUENCE: 32

```
Glu Val Gln Leu Gln Gln Ser Gly Pro Glu Leu Met Lys Thr Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Asp Ile Leu Pro Gly Ser Gly Thr Thr Asn Tyr Asn Glu Lys Phe
    50                  55                  60

Lys Gly Lys Ala Ala Ile Thr Ala Asp Thr Ser Ser Asn Thr Ser Tyr
65                  70                  75                  80

Leu Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
            100                 105                 110

Val Ser Ser
        115
```

<210> SEQ ID NO 33

```
<211> LENGTH: 115
<212> TYPE: PRT
<213> ORGANISM: Artificial sequence
<220> FEATURE:
<223> OTHER INFORMATION: synthetic heavy chain variable region (VH) of
      14E5Mut11 monoclonal antibody

<400> SEQUENCE: 33

Glu Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Thr Asn
            20                  25                  30

Trp Ile Glu Trp Ile Lys Gln Arg Pro Gly His Gly Leu Glu Trp Ile
        35                  40                  45

Gly His Ile Leu Pro Gly Ser Val Ile Thr Asn Tyr Asn Glu Lys Phe
    50                  55                  60

Lys Gly Lys Ala Ala Ile Thr Ala Asp Thr Ser Ser Asn Thr Ser Tyr
65                  70                  75                  80

Met Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
            100                 105                 110

Val Ser Ser
        115

<210> SEQ ID NO 34
<211> LENGTH: 115
<212> TYPE: PRT
<213> ORGANISM: Artificial sequence
<220> FEATURE:
<223> OTHER INFORMATION: synthetic heavy chain variable region (VH) of
      14E5Mut42 monoclonal antibody

<400> SEQUENCE: 34

Glu Val Pro Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Thr Tyr
            20                  25                  30

Trp Ile Glu Trp Ile Lys Gln Arg Pro Gly His Gly Leu Glu Trp Ile
        35                  40                  45

Gly His Ile Leu Pro Gly Ser Val Ile Thr Asn Tyr Asn Glu Lys Phe
    50                  55                  60

Lys Gly Lys Ala Ala Ile Thr Ala Asp Thr Ser Ser Asn Thr Ser Tyr
65                  70                  75                  80

Met Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
            100                 105                 110

Val Ser Ser
        115

<210> SEQ ID NO 35
<211> LENGTH: 115
<212> TYPE: PRT
<213> ORGANISM: Artificial sequence
<220> FEATURE:
<223> OTHER INFORMATION: synthetic heavy chain variable region (VH) of
      14E5Mut54 monoclonal antibody

<400> SEQUENCE: 35
```

```
Glu Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Thr Asn
            20                  25                  30

Trp Ile Glu Trp Ile Lys Gln Arg Pro Gly His Gly Leu Glu Trp Ile
        35                  40                  45

Gly His Ile Leu Pro Gly Ser Val Ile Thr Asn Tyr Asn Glu Lys Phe
    50                  55                  60

Lys Gly Lys Ala Ala Ile Thr Ala Asp Thr Ser Asn Thr Ser Tyr
65                  70                  75                  80

Met Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
            100                 105                 110

Val Ser Ser
        115

<210> SEQ ID NO 36
<211> LENGTH: 115
<212> TYPE: PRT
<213> ORGANISM: Artificial sequence
<220> FEATURE:
<223> OTHER INFORMATION: synthetic heavy chain variable region (VH) of
      14E5Mut68 monoclonal antibody

<400> SEQUENCE: 36

Glu Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Thr Tyr
            20                  25                  30

Trp Ile Glu Trp Ile Lys Gln Arg Pro Gly His Gly Leu Glu Trp Ile
        35                  40                  45

Gly Asp Ile Leu Pro Gly Ser Gly Thr Thr Asn Tyr Asn Glu Lys Phe
    50                  55                  60

Lys Gly Arg Ala Thr Val Thr Ala Asp Arg Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
            100                 105                 110

Val Ser Ser
        115

<210> SEQ ID NO 37
<211> LENGTH: 115
<212> TYPE: PRT
<213> ORGANISM: Artificial sequence
<220> FEATURE:
<223> OTHER INFORMATION: synthetic heavy chain variable region (VH) of
      14E5Mut65 monoclonal antibody

<400> SEQUENCE: 37

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Ser Phe Ser Thr Asn
            20                  25                  30

Trp Ile Glu Trp Ile Lys Gln Arg Pro Gly His Gly Leu Glu Trp Ile
        35                  40                  45
```

Gly His Ile Leu Pro Gly Ser Val Ile Thr Asn Tyr Asn Glu Lys Phe
        50                  55                  60

Lys Gly Lys Ala Ala Ile Thr Ala Asp Thr Ser Ser Asn Thr Ser Tyr
 65                  70                  75                  80

Met Gln Leu Ser Ser Leu Thr Ser Asp Asp Ser Ala Val Tyr Tyr Cys
                85                  90                  95

Ala Arg Trp Gly Trp Asp Ser Tyr Trp Gly Gln Gly Thr Leu Val Thr
               100                 105                 110

Val Ser Ser
        115

<210> SEQ ID NO 38
<211> LENGTH: 115
<212> TYPE: PRT
<213> ORGANISM: Artificial sequence
<220> FEATURE:
<223> OTHER INFORMATION: synthetic heavy chain variable region (VH) of
      14E5Mut83 monoclonal antibody

<400> SEQUENCE: 38

Glu Val Gln Leu Gln Gln Ser Gly Ala Val Leu Met Lys Pro Gly Ala
 1               5                  10                  15

Ser Val Lys Ile Ser Cys Lys Ala Thr Gly Tyr Thr Phe Ser Thr His
                20                  25                  30

Trp Ile Glu Trp Ile Lys Gln Arg Pro Gly His Gly Leu Glu Trp Ile
            35                  40                  45

Gly His Ile Leu Pro Gly Ser Val Ile Thr Asn Tyr Asn Glu Lys Phe
        50                  55                  60

Lys Gly Lys Ala Ala Ile Thr Ala Asp Thr Ser Ser Asn Thr Ser Tyr
 65                  70                  75                  80

Met Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
               100                 105                 110

Val Ser Ser
        115

<210> SEQ ID NO 39
<211> LENGTH: 115
<212> TYPE: PRT
<213> ORGANISM: Artificial sequence
<220> FEATURE:
<223> OTHER INFORMATION: synthetic heavy chain variable region (VH) of
      14E5Mut95 monoclonal antibody

<400> SEQUENCE: 39

Glu Val Gln Leu Gln Gln Thr Gly Ala Glu Leu Met Lys Pro Gly Ala
 1               5                  10                  15

Ser Val Lys Ile Ser Cys Lys Ala Thr Gly Tyr Thr Phe Ser Thr Tyr
                20                  25                  30

Trp Ile Glu Trp Ile Lys Gln Arg Pro Gly His Gly Leu Glu Trp Ile
            35                  40                  45

Gly His Ile Leu Pro Gly Ser Val Ile Thr Asn Tyr Asn Glu Lys Phe
        50                  55                  60

Lys Gly Lys Ala Val Ile Thr Ala Asp Thr Ser Ser Asn Thr Ser Tyr
 65                  70                  75                  80

Met Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
            100                 105                 110

Val Ser Ser
        115

<210> SEQ ID NO 40
<211> LENGTH: 5
<212> TYPE: PRT
<213> ORGANISM: Artificial sequence
<220> FEATURE:
<223> OTHER INFORMATION: synthetic heavy chain variable region CDR1 of
      6B9 monoclonal antibody

<400> SEQUENCE: 40

Asp Tyr Leu Ile Glu
1               5

<210> SEQ ID NO 41
<211> LENGTH: 17
<212> TYPE: PRT
<213> ORGANISM: Artificial sequence
<220> FEATURE:
<223> OTHER INFORMATION: synthetic heavy chain variable region CDR2 of
      6B9 monoclonal antibody

<400> SEQUENCE: 41

Val Ile Asn Pro Glu Thr Gly Gly Thr Asn Tyr Asn Ala Lys Phe Lys
1               5                   10                  15

Gly

<210> SEQ ID NO 42
<211> LENGTH: 11
<212> TYPE: PRT
<213> ORGANISM: Artificial sequence
<220> FEATURE:
<223> OTHER INFORMATION: synthetic heavy chain variable region CDR3 of
      6B9 monoclonal antibody

<400> SEQUENCE: 42

Glu Ala Gly Asn Tyr Ile Tyr Ala Met Asp Tyr
1               5                   10

<210> SEQ ID NO 43
<211> LENGTH: 11
<212> TYPE: PRT
<213> ORGANISM: Artificial sequence
<220> FEATURE:
<223> OTHER INFORMATION: synthetic light chain variable region CDR1 of
      6B9 monoclonal antibody

<400> SEQUENCE: 43

Arg Ala Ser Val Asn Ile Tyr Ser Tyr Leu Val
1               5                   10

<210> SEQ ID NO 44
<211> LENGTH: 7
<212> TYPE: PRT
<213> ORGANISM: Artificial sequence
<220> FEATURE:
<223> OTHER INFORMATION: synthetic light chain variable region CDR2 of
      6B9 monoclonal antibody

<400> SEQUENCE: 44

Asn Ala Lys Thr Leu Ala Glu
1               5

```
<210> SEQ ID NO 45
<211> LENGTH: 9
<212> TYPE: PRT
<213> ORGANISM: Artificial sequence
<220> FEATURE:
<223> OTHER INFORMATION: synthetic light chain variable region CDR3 of
      6B9 monoclonal antibody

<400> SEQUENCE: 45

Gln His His His Gly Thr Pro Tyr Thr
1               5

<210> SEQ ID NO 46
<211> LENGTH: 17
<212> TYPE: PRT
<213> ORGANISM: Artificial sequence
<220> FEATURE:
<223> OTHER INFORMATION: synthetic heavy chain variable region CDR2 of
      affinity matured 6B9 monoclonal antibody (6B9Mut1)

<400> SEQUENCE: 46

Val Ile Asn Pro Glu Thr Gly Gly Thr Asn Tyr Asn Ala Lys Phe Arg
1               5                   10                  15

Gly

<210> SEQ ID NO 47
<211> LENGTH: 23
<212> TYPE: PRT
<213> ORGANISM: Artificial sequence
<220> FEATURE:
<223> OTHER INFORMATION: synthetic light chain framework region FR1 of
      affinity matured 6B9 monoclonal antibody (6B9Mut1)

<400> SEQUENCE: 47

Asp Ile Val Met Thr Gln Ser Pro Ala Ser Leu Ser Ala Ser Val Gly
1               5                   10                  15

Glu Thr Val Thr Ile Thr Cys
            20

<210> SEQ ID NO 48
<211> LENGTH: 5
<212> TYPE: PRT
<213> ORGANISM: Artificial sequence
<220> FEATURE:
<223> OTHER INFORMATION: synthetic heavy chain variable region CDR1 of
      11E8 monoclonal antibody

<400> SEQUENCE: 48

Ser Tyr Trp Ile Glu
1               5

<210> SEQ ID NO 49
<211> LENGTH: 17
<212> TYPE: PRT
<213> ORGANISM: Artificial sequence
<220> FEATURE:
<223> OTHER INFORMATION: synthetic heavy chain variable region CDR2 of
      11E8 monoclonal antibody

<400> SEQUENCE: 49

Asp Ile Leu Pro Gly Ser Gly Thr Thr Asn Tyr Asn Glu Lys Phe Lys
1               5                   10                  15

Gly

<210> SEQ ID NO 50
<211> LENGTH: 6
```

```
<212> TYPE: PRT
<213> ORGANISM: Artificial sequence
<220> FEATURE:
<223> OTHER INFORMATION: synthetic heavy chain variable region CDR3 of
      11E8 monoclonal antibody

<400> SEQUENCE: 50

Trp Gly Trp Asp Thr Tyr
1               5

<210> SEQ ID NO 51
<211> LENGTH: 11
<212> TYPE: PRT
<213> ORGANISM: Artificial sequence
<220> FEATURE:
<223> OTHER INFORMATION: synthetic light chain variable region CDR1 of
      11E8 monoclonal antibody

<400> SEQUENCE: 51

Ser Ala Ser Gln Gly Ile Ser Asn Tyr Leu Asn
1               5                   10

<210> SEQ ID NO 52
<211> LENGTH: 7
<212> TYPE: PRT
<213> ORGANISM: Artificial sequence
<220> FEATURE:
<223> OTHER INFORMATION: synthetic light chain variable region CDR2 of
      11E8 monoclonal antibody

<400> SEQUENCE: 52

Tyr Thr Ser Ser Leu His Ser
1               5

<210> SEQ ID NO 53
<211> LENGTH: 9
<212> TYPE: PRT
<213> ORGANISM: Artificial sequence
<220> FEATURE:
<223> OTHER INFORMATION: synthetic light chain variable region CDR3 of
      11E8 monoclonal antibody

<400> SEQUENCE: 53

Gln Gln Tyr Ser Asn Leu Pro Tyr Thr
1               5

<210> SEQ ID NO 54
<211> LENGTH: 6
<212> TYPE: PRT
<213> ORGANISM: Artificial sequence
<220> FEATURE:
<223> OTHER INFORMATION: synthetic heavy chain variable region CDR3 of
      affinity matured 11E8 monoclonal antibody (11E8Mut28 and
      11E8Mut94)

<400> SEQUENCE: 54

Trp Gly Trp Asp Ser Tyr
1               5

<210> SEQ ID NO 55
<211> LENGTH: 9
<212> TYPE: PRT
<213> ORGANISM: Artificial sequence
<220> FEATURE:
<223> OTHER INFORMATION: synthetic light chain variable region CDR3 of
      affinity matured 11E8 monoclonal antibody (11E8Mut28)

<400> SEQUENCE: 55
```

```
Gln Gln Phe Ser Asn Leu Pro Tyr Thr
1               5
```

<210> SEQ ID NO 56
<211> LENGTH: 32
<212> TYPE: PRT
<213> ORGANISM: Artificial sequence
<220> FEATURE:
<223> OTHER INFORMATION: synthetic heavy chain framework region FR3 of
      affinity matured 11E8 monoclonal antibody (11E8Mut28)

<400> SEQUENCE: 56

```
Lys Ala Ala Ile Thr Ala Asp Thr Ser Ser Asn Thr Ser Tyr Leu Gln
1               5                   10                  15

Leu Ser Ser Leu Thr Ser Glu Asp Ser Ala Val Tyr Tyr Cys Ala Arg
            20                  25                  30
```

<210> SEQ ID NO 57
<211> LENGTH: 11
<212> TYPE: PRT
<213> ORGANISM: Artificial sequence
<220> FEATURE:
<223> OTHER INFORMATION: synthetic heavy chain framework region FR4 of
      affinity matured 11E8 monoclonal antibody (11E8Mut28 and
      11E8Mut94)

<400> SEQUENCE: 57

```
Trp Gly Gln Gly Thr Leu Val Thr Val Ser Ser
1               5                   10
```

<210> SEQ ID NO 58
<211> LENGTH: 5
<212> TYPE: PRT
<213> ORGANISM: Artificial sequence
<220> FEATURE:
<223> OTHER INFORMATION: synthetic heavy chain variable region CDR1 of
      14E5 monoclonal antibody

<400> SEQUENCE: 58

```
Thr Tyr Trp Ile Glu
1               5
```

<210> SEQ ID NO 59
<211> LENGTH: 17
<212> TYPE: PRT
<213> ORGANISM: Artificial sequence
<220> FEATURE:
<223> OTHER INFORMATION: synthetic heavy chain variable region CDR2 of
      14E5 monoclonal antibody

<400> SEQUENCE: 59

```
His Ile Leu Pro Gly Ser Val Ile Thr Asn Tyr Asn Glu Lys Phe Lys
1               5                   10                  15

Gly
```

<210> SEQ ID NO 60
<211> LENGTH: 6
<212> TYPE: PRT
<213> ORGANISM: Artificial sequence
<220> FEATURE:
<223> OTHER INFORMATION: synthetic heavy chain variable region CDR3 of
      14E5 monoclonal antibody

<400> SEQUENCE: 60

```
Trp Gly Trp Asp Ser Tyr
1               5
```

<210> SEQ ID NO 61
<211> LENGTH: 11
<212> TYPE: PRT
<213> ORGANISM: Artificial sequence
<220> FEATURE:
<223> OTHER INFORMATION: synthetic light chain variable region CDR1 of
      14E5 monoclonal antibody

<400> SEQUENCE: 61

Ser Thr Ser Gln Asp Ile Ser Ser Ser Leu Asn
1               5                   10

<210> SEQ ID NO 62
<211> LENGTH: 7
<212> TYPE: PRT
<213> ORGANISM: Artificial sequence
<220> FEATURE:
<223> OTHER INFORMATION: synthetic light chain variable region CDR2 of
      14E5 monoclonal antibody

<400> SEQUENCE: 62

Tyr Thr Ser Asn Leu His Ser
1               5

<210> SEQ ID NO 63
<211> LENGTH: 9
<212> TYPE: PRT
<213> ORGANISM: Artificial sequence
<220> FEATURE:
<223> OTHER INFORMATION: synthetic light chain variable region CDR3 of
      14E5 monoclonal antibody

<400> SEQUENCE: 63

Gln Gln Tyr Ser Lys Leu Pro Tyr Thr
1               5

<210> SEQ ID NO 64
<211> LENGTH: 5
<212> TYPE: PRT
<213> ORGANISM: Artificial sequence
<220> FEATURE:
<223> OTHER INFORMATION: synthetic heavy chain variable region CDR1 of
      affinity matured 14E5 monoclonal antibody (14E5Mut11, 14E5Mut54
      and 14E5Mut65)

<400> SEQUENCE: 64

Thr Asn Trp Ile Glu
1               5

<210> SEQ ID NO 65
<211> LENGTH: 11
<212> TYPE: PRT
<213> ORGANISM: Artificial sequence
<220> FEATURE:
<223> OTHER INFORMATION: synthetic light chain variable region CDR1 of
      affinity matured 14E5 monoclonal antibody (14E5Mut11)

<400> SEQUENCE: 65

Ser Ala Ser Gln Gly Ile Ser Lys Tyr Leu Asn
1               5                   10

<210> SEQ ID NO 66
<211> LENGTH: 7
<212> TYPE: PRT
<213> ORGANISM: Artificial sequence
<220> FEATURE:
<223> OTHER INFORMATION: synthetic light chain variable region CDR2 of
      affinity matured 14E5 monoclonal antibody (14E5Mut11, 14E5Mut42, -continued 14E5Mut54, 14E5Mut68, 14E5Mut65, 14E5Mut83 and 14E5Mut95)

<400> SEQUENCE: 66

Tyr Thr Ser Ser Leu His Ser
1               5

<210> SEQ ID NO 67
<211> LENGTH: 9
<212> TYPE: PRT
<213> ORGANISM: Artificial sequence
<220> FEATURE:
<223> OTHER INFORMATION: synthetic light chain variable region CDR3 of
      affinity matured 14E5 monoclonal antibody (14E5Mut11 and
      14E5Mut54)

<400> SEQUENCE: 67

Gln Gln Tyr Ser Asn Leu Pro Tyr Thr
1               5

<210> SEQ ID NO 68
<211> LENGTH: 23
<212> TYPE: PRT
<213> ORGANISM: Artificial sequence
<220> FEATURE:
<223> OTHER INFORMATION: synthetic light chain framework region FR1 of
      affinity matured 14E5 monoclonal antibody (14E5Mut11 and
      14E5Mut83)

<400> SEQUENCE: 68

Asp Ile Leu Met Thr Gln Ser Pro Ser Ser Leu Ser Ala Ser Leu Gly
1               5                   10                  15

Asp Arg Val Thr Ile Ser Cys
            20

<210> SEQ ID NO 69
<211> LENGTH: 15
<212> TYPE: PRT
<213> ORGANISM: Artificial sequence
<220> FEATURE:
<223> OTHER INFORMATION: synthetic light chain framework region FR2 of
      affinity matured 14E5 monoclonal antibody (14E5Mut11, 14E5Mut42,
      14E5Mut54, 14E5Mut68, 14E5Mut65, 14E5Mut83 and 14E5Mut95)

<400> SEQUENCE: 69

Trp Tyr Gln Gln Lys Pro Asp Gly Thr Val Lys Leu Leu Thr Tyr
1               5                   10                  15

<210> SEQ ID NO 70
<211> LENGTH: 11
<212> TYPE: PRT
<213> ORGANISM: Artificial sequence
<220> FEATURE:
<223> OTHER INFORMATION: synthetic light chain variable region CDR1 of
      affinity matured 14E5 monoclonal antibody (14E5Mut42, 14E5Mut54,
      14E5Mut68, 14E5Mut65, 14E5Mut83 and 14E5Mut95)

<400> SEQUENCE: 70

Ser Ala Ser Gln Gly Ile Ser Asn Tyr Leu Asn
1               5                   10

<210> SEQ ID NO 71
<211> LENGTH: 9
<212> TYPE: PRT
<213> ORGANISM: Artificial sequence
<220> FEATURE:
<223> OTHER INFORMATION: synthetic light chain variable region CDR3 of
      affinity matured 14E5 monoclonal antibody (14E5Mut42, 14E5Mut83
      and 14E5Mut95)

<400> SEQUENCE: 71

Gln Gln Tyr Ser Asp Leu Pro Tyr Thr
1               5

<210> SEQ ID NO 72
<211> LENGTH: 30
<212> TYPE: PRT
<213> ORGANISM: Artificial sequence
<220> FEATURE:
<223> OTHER INFORMATION: synthetic heavy chain framework region FR1 of
      affinity matured 14E5 monoclonal antibody (14E5Mut42)

<400> SEQUENCE: 72

Glu Val Pro Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser
            20                  25                  30

<210> SEQ ID NO 73
<211> LENGTH: 23
<212> TYPE: PRT
<213> ORGANISM: Artificial sequence
<220> FEATURE:
<223> OTHER INFORMATION: synthetic light chain framework region FR1 of
      affinity matured 14E5 monoclonal antibody (14E5Mut42)

<400> SEQUENCE: 73

Asp Ile Val Met Thr Gln Thr Pro Ser Ser Leu Ser Ala Ser Leu Gly
1               5                   10                  15

Asp Arg Val Thr Ile Ser Cys
            20

<210> SEQ ID NO 74
<211> LENGTH: 32
<212> TYPE: PRT
<213> ORGANISM: Artificial sequence
<220> FEATURE:
<223> OTHER INFORMATION: synthetic heavy chain framework region FR3 of
      affinity matured 14E5 monoclonal antibody (14E5Mut54)

<400> SEQUENCE: 74

Lys Ala Ala Ile Thr Ala Asp Thr Ser Ser Asn Thr Ser Tyr Met Gln
1               5                   10                  15

Leu Thr Ser Leu Thr Ser Glu Asp Ser Ala Val Tyr Tyr Cys Ala Arg
            20                  25                  30

<210> SEQ ID NO 75
<211> LENGTH: 23
<212> TYPE: PRT
<213> ORGANISM: Artificial sequence
<220> FEATURE:
<223> OTHER INFORMATION: synthetic light chain framework region FR1 of
      affinity matured 14E5 monoclonal antibody (14E5Mut54)

<400> SEQUENCE: 75

Asp Ile Leu Met Thr Gln Thr Pro Ser Ser Leu Ser Ala Ser Leu Gly
1               5                   10                  15

Asp Arg Val Thr Ile Arg Cys
            20

<210> SEQ ID NO 76
<211> LENGTH: 17
<212> TYPE: PRT
<213> ORGANISM: Artificial sequence

```
<220> FEATURE:
<223> OTHER INFORMATION: synthetic heavy chain variable region CDR2 of
      affinity matured 14E5 monoclonal antibody (14E5Mut68)

<400> SEQUENCE: 76

Asp Ile Leu Pro Gly Ser Gly Thr Thr Asn Tyr Asn Glu Lys Phe Lys
1               5                   10                  15

Gly

<210> SEQ ID NO 77
<211> LENGTH: 9
<212> TYPE: PRT
<213> ORGANISM: Artificial sequence
<220> FEATURE:
<223> OTHER INFORMATION: synthetic light chain variable region CDR3 of
      affinity matured 14E5 monoclonal antibody (14E5Mut68)

<400> SEQUENCE: 77

Gln Gln Tyr Ser Glu Leu Pro Tyr Thr
1               5

<210> SEQ ID NO 78
<211> LENGTH: 32
<212> TYPE: PRT
<213> ORGANISM: Artificial sequence
<220> FEATURE:
<223> OTHER INFORMATION: synthetic heavy chain framework region FR3 of
      affinity matured 14E5 monoclonal antibody (14E5Mut68)

<400> SEQUENCE: 78

Arg Ala Thr Val Thr Ala Asp Arg Ser Ser Asn Thr Ser Tyr Met Gln
1               5                   10                  15

Leu Ser Ser Leu Thr Ser Glu Asp Ser Ala Val Tyr Tyr Cys Ala Arg
                20                  25                  30

<210> SEQ ID NO 79
<211> LENGTH: 23
<212> TYPE: PRT
<213> ORGANISM: Artificial sequence
<220> FEATURE:
<223> OTHER INFORMATION: synthetic light chain framework region FR1 of
      affinity matured 14E5 monoclonal antibody (14E5Mut68 14E5Mut65)

<400> SEQUENCE: 79

Asp Ile Lys Met Thr Gln Ser Pro Ser Ser Leu Ser Ala Ser Leu Gly
1               5                   10                  15

Asp Arg Val Thr Ile Ser Cys
                20

<210> SEQ ID NO 80
<211> LENGTH: 9
<212> TYPE: PRT
<213> ORGANISM: Artificial sequence
<220> FEATURE:
<223> OTHER INFORMATION: synthetic light chain variable region CDR3 of
      affinity matured 14E5 monoclonal antibody (14E5Mut65)

<400> SEQUENCE: 80

Gln Gln Phe Ser Asn Leu Pro Tyr Thr
1               5

<210> SEQ ID NO 81
<211> LENGTH: 30
<212> TYPE: PRT
<213> ORGANISM: Artificial sequence
<220> FEATURE:
```

```
<223> OTHER INFORMATION: synthetic heavy chain framework region FR1 of
      affinity matured 14E5 monoclonal antibody (14E5Mut65)

<400> SEQUENCE: 81

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Ser Phe Ser
            20                  25                  30

<210> SEQ ID NO 82
<211> LENGTH: 32
<212> TYPE: PRT
<213> ORGANISM: Artificial sequence
<220> FEATURE:
<223> OTHER INFORMATION: synthetic heavy chain framework region FR3 of
      affinity matured 14E5 monoclonal antibody (14E5Mut65)

<400> SEQUENCE: 82

Lys Ala Ala Ile Thr Ala Asp Thr Ser Ser Asn Thr Ser Tyr Met Gln
1               5                   10                  15

Leu Ser Ser Leu Thr Ser Asp Asp Ser Ala Val Tyr Tyr Cys Ala Arg
            20                  25                  30

<210> SEQ ID NO 83
<211> LENGTH: 5
<212> TYPE: PRT
<213> ORGANISM: Artificial sequence
<220> FEATURE:
<223> OTHER INFORMATION: synthetic heavy chain variable region CDR1 of
      affinity matured 14E5 monoclonal antibody (14E5Mut83)

<400> SEQUENCE: 83

Thr His Trp Ile Glu
1               5

<210> SEQ ID NO 84
<211> LENGTH: 30
<212> TYPE: PRT
<213> ORGANISM: Artificial sequence
<220> FEATURE:
<223> OTHER INFORMATION: synthetic heavy chain framework region FR1 of
      affinity matured 14E5 monoclonal antibody (14E5Mut83)

<400> SEQUENCE: 84

Glu Val Gln Leu Gln Gln Ser Gly Ala Val Leu Met Lys Pro Gly Ala
1               5                   10                  15

Ser Val Lys Ile Ser Cys Lys Ala Thr Gly Tyr Thr Phe Ser
            20                  25                  30

<210> SEQ ID NO 85
<211> LENGTH: 30
<212> TYPE: PRT
<213> ORGANISM: Artificial sequence
<220> FEATURE:
<223> OTHER INFORMATION: synthetic heavy chain framework region FR1 of
      affinity matured 14E5 monoclonal antibody (14E5Mut95)

<400> SEQUENCE: 85

Glu Val Gln Leu Gln Gln Thr Gly Ala Glu Leu Met Lys Pro Gly Ala
1               5                   10                  15

Ser Val Lys Ile Ser Cys Lys Ala Thr Gly Tyr Thr Phe Ser
            20                  25                  30

<210> SEQ ID NO 86
<211> LENGTH: 32
```

```
<212> TYPE: PRT
<213> ORGANISM: Artificial sequence
<220> FEATURE:
<223> OTHER INFORMATION: synthetic heavy chain framework region FR3 of
      affinity matured 14E5 monoclonal antibody (14E5Mut95)

<400> SEQUENCE: 86

Lys Ala Val Ile Thr Ala Asp Thr Ser Ser Asn Thr Ser Tyr Met Gln
1               5                  10                  15

Leu Ser Ser Leu Thr Ser Glu Asp Ser Ala Val Tyr Tyr Cys Ala Arg
            20                  25                  30

<210> SEQ ID NO 87
<211> LENGTH: 23
<212> TYPE: PRT
<213> ORGANISM: Artificial sequence
<220> FEATURE:
<223> OTHER INFORMATION: synthetic light chain framework region FR1 of
      affinity matured 14E5 monoclonal antibody (14E5Mut95)

<400> SEQUENCE: 87

Asp Ile Glu Met Thr Gln Ser Pro Ser Ser Leu Ser Ala Ser Leu Gly
1               5                  10                  15

Asp Arg Val Thr Ile Ser Cys
            20

<210> SEQ ID NO 88
<211> LENGTH: 115
<212> TYPE: PRT
<213> ORGANISM: Artificial sequence
<220> FEATURE:
<223> OTHER INFORMATION: synthetic heavy chain variable region (VH) of
      11E8Mut94 monoclonal antibody

<400> SEQUENCE: 88

Glu Val Gln Leu Gln Gln Ser Gly Pro Glu Leu Met Lys Thr Gly Ala
1               5                  10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Asp Ile Leu Pro Gly Ser Gly Thr Thr Asn Tyr Asn Glu Lys Phe
    50                  55                  60

Glu Gly Arg Ala Ala Ile Thr Ala Asp Thr Ser Ser Asn Thr Ser Tyr
65                  70                  75                  80

Met Gln Leu Ser Ser Leu Thr Ser Glu Asp Ser Ala Val Tyr Tyr Cys
                85                  90                  95

Ala Arg Trp Gly Trp Asp Ser Tyr Trp Gly Gln Gly Thr Leu Val Thr
            100                 105                 110

Val Ser Ser
        115

<210> SEQ ID NO 89
<211> LENGTH: 108
<212> TYPE: PRT
<213> ORGANISM: Artificial sequence
<220> FEATURE:
<223> OTHER INFORMATION: synthetic light chain variable region (VK) of
      11E8Mut94 monoclonal antibody

<400> SEQUENCE: 89

Asp Ile Lys Met Thr Gln Thr Pro Ser Ser Leu Ser Ala Ser Leu Gly
1               5                  10                  15
```

```
Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Asn Leu Pro Tyr
                85                  90                  95

Thr Phe Gly Gly Gly Thr Lys Leu Glu Ile Lys Arg
            100                 105

<210> SEQ ID NO 90
<211> LENGTH: 17
<212> TYPE: PRT
<213> ORGANISM: Artificial sequence
<220> FEATURE:
<223> OTHER INFORMATION: synthetic heavy chain variable region CDR2 of
      affinity matured 11E8 monoclonal antibody (11E8Mut94)

<400> SEQUENCE: 90

Asp Ile Leu Pro Gly Ser Gly Thr Thr Asn Tyr Asn Glu Lys Phe Glu
1               5                   10                  15

Gly

<210> SEQ ID NO 91
<211> LENGTH: 14
<212> TYPE: PRT
<213> ORGANISM: Artificial sequence
<220> FEATURE:
<223> OTHER INFORMATION: synthetic heavy chain framework region FR2 of
      affinity matured 11E8 monoclonal antibody (11E8Mut94)

<400> SEQUENCE: 91

Trp Val Lys Gln Arg Pro Gly His Gly Phe Glu Trp Ile Gly
1               5                   10

<210> SEQ ID NO 92
<211> LENGTH: 32
<212> TYPE: PRT
<213> ORGANISM: Artificial sequence
<220> FEATURE:
<223> OTHER INFORMATION: synthetic heavy chain framework region FR3 of
      affinity matured 11E8 monoclonal antibody (11E8Mut94)

<400> SEQUENCE: 92

Arg Ala Ala Ile Thr Ala Asp Thr Ser Ser Asn Thr Ser Tyr Met Gln
1               5                   10                  15

Leu Ser Ser Leu Thr Ser Glu Asp Ser Ala Val Tyr Tyr Cys Ala Arg
            20                  25                  30

<210> SEQ ID NO 93
<211> LENGTH: 23
<212> TYPE: PRT
<213> ORGANISM: Artificial sequence
<220> FEATURE:
<223> OTHER INFORMATION: synthetic light chain framework region FR1 of
      affinity matured 11E8 monoclonal antibody (11E8Mut94)

<400> SEQUENCE: 93

Asp Ile Lys Met Thr Gln Thr Pro Ser Ser Leu Ser Ala Ser Leu Gly
1               5                   10                  15
```

```
Asp Arg Val Thr Ile Ser Cys
            20

<210> SEQ ID NO 94
<211> LENGTH: 5
<212> TYPE: PRT
<213> ORGANISM: Artificial sequence
<220> FEATURE:
<223> OTHER INFORMATION: synthetic heavy chain variable region CDR1 of
      37E1, 37E1B5 and Hu37E1B5 monoclonal antibody

<400> SEQUENCE: 94

Arg Tyr Trp Met Ser
1               5

<210> SEQ ID NO 95
<211> LENGTH: 17
<212> TYPE: PRT
<213> ORGANISM: Artificial sequence
<220> FEATURE:
<223> OTHER INFORMATION: synthetic heavy chain variable region CDR2 of
      37E1, 37E1B5 and Hu37E1B5 monoclonal antibody

<400> SEQUENCE: 95

Glu Ile Asn Pro Asp Ser Ser Thr Ile Asn Tyr Thr Ser Ser Leu Lys
1               5                   10                  15

Asp

<210> SEQ ID NO 96
<211> LENGTH: 7
<212> TYPE: PRT
<213> ORGANISM: Artificial sequence
<220> FEATURE:
<223> OTHER INFORMATION: synthetic heavy chain variable region CDR3 of
      37E1, 37E1B5 and Hu37E1B5 monoclonal antibody

<400> SEQUENCE: 96

Leu Ile Thr Thr Glu Asp Tyr
1               5

<210> SEQ ID NO 97
<211> LENGTH: 10
<212> TYPE: PRT
<213> ORGANISM: Artificial sequence
<220> FEATURE:
<223> OTHER INFORMATION: synthetic light chain variable region CDR1 of
      37E1, 37E1B5 and Hu37E1B5 monoclonal antibody

<400> SEQUENCE: 97

Lys Ala Ser Gln Asp Ile Asn Ser Tyr Leu
1               5                   10

<210> SEQ ID NO 98
<211> LENGTH: 7
<212> TYPE: PRT
<213> ORGANISM: Artificial sequence
<220> FEATURE:
<223> OTHER INFORMATION: synthetic light chain variable region CDR2 of
      37E1 monoclonal antibody

<400> SEQUENCE: 98

Arg Ala Asn Arg Leu Val Asp
1               5

<210> SEQ ID NO 99
<211> LENGTH: 9
```

<212> TYPE: PRT
<213> ORGANISM: Artificial sequence
<220> FEATURE:
<223> OTHER INFORMATION: synthetic light chain variable region CDR3 of
      37E1, 37E1B5 and Hu37E1B5 monoclonal antibody

<400> SEQUENCE: 99

Leu Gln Tyr Asp Glu Phe Pro Tyr Thr
1               5

<210> SEQ ID NO 100
<211> LENGTH: 7
<212> TYPE: PRT
<213> ORGANISM: Artificial sequence
<220> FEATURE:
<223> OTHER INFORMATION: synthetic light chain variable region CDR2 of
      37E1B5 and Hu37E1B5 monoclonal antibody

<400> SEQUENCE: 100

Tyr Ala Asn Arg Leu Val Asp
1               5

<210> SEQ ID NO 101

<400> SEQUENCE: 101

000

<210> SEQ ID NO 102
<211> LENGTH: 115
<212> TYPE: PRT
<213> ORGANISM: Artificial sequence
<220> FEATURE:
<223> OTHER INFORMATION: synthetic heavy chain variable region (VH) of
      11E8Mut39 monoclonal antibody

<400> SEQUENCE: 102

Glu Val Gln Leu Gln Gln Ser Gly Pro Glu Leu Met Lys Thr Gly Ala
1               5                   10                  15

Ser Val Lys Ile Ser Cys Lys Ala Thr Gly Tyr Thr Phe Ser Thr Tyr
                20                  25                  30

Trp Ile Glu Trp Val Lys Gln Arg Pro Gly His Gly Leu Glu Trp Ile
            35                  40                  45

Gly His Thr Leu Pro Gly Ser Gly Thr Thr Asn Tyr Asn Glu Lys Phe
        50                  55                  60

Lys Gly Arg Ala Thr Ile Thr Ala Asp Arg Pro Ser Asn Thr Ser Tyr
65                  70                  75                  80

Met Gln Leu Ser Ser Leu Thr Tyr Gly Asp Ser Ala Val Phe Tyr Cys
                85                  90                  95

Ala Thr Trp Gly Trp Asp Thr Tyr Trp Asp His Gly Thr Ser Val Thr
            100                 105                 110

Val Ser Ser
        115

<210> SEQ ID NO 103

<400> SEQUENCE: 103

000

<210> SEQ ID NO 104
<211> LENGTH: 108
<212> TYPE: PRT
<213> ORGANISM: Artificial sequence

```
<220> FEATURE:
<223> OTHER INFORMATION: synthetic light chain variable region (VK) of
      11E8Mut39 monoclonal antibody

<400> SEQUENCE: 104

Asp Ile Glu Met Thr Gln Ser Pro Ser Leu Ser Ala Ser Leu Gly
1               5                   10                  15

Asp Arg Val Thr Ile Ser Cys Ser Thr Ser Gln Asp Val Ser Ser Tyr
            20                  25                  30

Leu Asn Trp Tyr Gln Gln Lys Pro Asp Gly Thr Val Thr Leu Leu Ile
        35                  40                  45

Tyr Tyr Ala Ser Asn Leu His Ser Gly Val Pro Ser Arg Phe Ser Gly
    50                  55                  60

Ser Gly Ser Gly Thr Asp Tyr Ser Leu Ala Ile Ser Asn Leu Glu Pro
65                  70                  75                  80

Glu Asp Ile Ala Thr Tyr Tyr Cys Gln Gln Tyr Ser Asn Leu Pro Tyr
                85                  90                  95

Thr Phe Gly Gly Gly Thr Lys Leu Glu Ile Lys Ala
            100                 105

<210> SEQ ID NO 105
<211> LENGTH: 11
<212> TYPE: PRT
<213> ORGANISM: Artificial sequence
<220> FEATURE:
<223> OTHER INFORMATION: synthetic light chain variable region CDR1 of
      affinity matured 11E8 monoclonal antibody (11E8Mut39)

<400> SEQUENCE: 105

Ser Thr Ser Gln Asp Val Ser Ser Tyr Leu Asn
1               5                   10

<210> SEQ ID NO 106
<211> LENGTH: 30
<212> TYPE: PRT
<213> ORGANISM: Artificial sequence
<220> FEATURE:
<223> OTHER INFORMATION: synthetic heavy chain framework region FR1 of
      affinity matured 11E8 monoclonal antibody (11E8Mut39)

<400> SEQUENCE: 106

Gln Val Gln Leu Gln Gln Ser Gly Pro Glu Leu Met Lys Thr Gly Ala
1               5                   10                  15

Ser Val Lys Ile Ser Cys Lys Ala Thr Gly Tyr Thr Phe Ser
            20                  25                  30

<210> SEQ ID NO 107
<211> LENGTH: 7
<212> TYPE: PRT
<213> ORGANISM: Artificial sequence
<220> FEATURE:
<223> OTHER INFORMATION: synthetic light chain variable region CDR2 of
      affinity matured 11E8 monoclonal antibody (11E8Mut39)

<400> SEQUENCE: 107

Tyr Ala Ser Asn Leu His Ser
1               5

<210> SEQ ID NO 108
<211> LENGTH: 11
<212> TYPE: PRT
<213> ORGANISM: Artificial sequence
<220> FEATURE:
<223> OTHER INFORMATION: synthetic heavy chain framework region FR4 of
``` affinity matured 11E8 monoclonal antibody (11E8Mut39)

<400> SEQUENCE: 108

Trp Asp His Gly Thr Ser Val Thr Val Ser Ser
1               5                   10

<210> SEQ ID NO 109

<400> SEQUENCE: 109

000

<210> SEQ ID NO 110

<400> SEQUENCE: 110

000

<210> SEQ ID NO 111
<211> LENGTH: 11
<212> TYPE: PRT
<213> ORGANISM: Artificial Sequence
<220> FEATURE:
<223> OTHER INFORMATION: Synthetic light chain framework region FR4 of
      affinity matured 11E8 monoclonal antibody (11E8Mut39)

<400> SEQUENCE: 111

Phe Gly Gly Gly Thr Lys Leu Glu Ile Lys Ala
1               5                   10

<210> SEQ ID NO 112
<211> LENGTH: 5
<212> TYPE: PRT
<213> ORGANISM: Artificial sequence
<220> FEATURE:
<223> OTHER INFORMATION: synthetic heavy chain variable region CDR1 of
      affinity matured 11E8 monoclonal antibody (11E8Mut39)

<400> SEQUENCE: 112

Thr Tyr Trp Ile Glu
1               5

<210> SEQ ID NO 113
<211> LENGTH: 17
<212> TYPE: PRT
<213> ORGANISM: Artificial sequence
<220> FEATURE:
<223> OTHER INFORMATION: synthetic heavy chain variable region CDR2 of
      affinity matured 11E8 monoclonal antibody (11E8Mut39)

<400> SEQUENCE: 113

His Thr Leu Pro Gly Ser Gly Thr Thr Asn Tyr Asn Glu Lys Phe Lys
1               5                   10                  15

Gly

<210> SEQ ID NO 114
<211> LENGTH: 32
<212> TYPE: PRT
<213> ORGANISM: Artificial sequence
<220> FEATURE:
<223> OTHER INFORMATION: synthetic heavy chain framework region FR3 of
      affinity matured 11E8 monoclonal antibody (11E8Mut39)

<400> SEQUENCE: 114

Arg Ala Thr Ile Thr Ala Asp Arg Pro Ser Asn Thr Ser Tyr Met Gln
1               5                   10                  15

```
Leu Ser Ser Leu Thr Tyr Gly Asp Ser Ala Val Phe Tyr Cys Ala Thr
            20                  25                  30
```

<210> SEQ ID NO 115
<211> LENGTH: 23
<212> TYPE: PRT
<213> ORGANISM: Artificial sequence
<220> FEATURE:
<223> OTHER INFORMATION: synthetic light chain framework region FR1 of
      affinity matured 11E8 monoclonal antibody (11E8Mut39)

<400> SEQUENCE: 115

```
Asp Ile Met Met Thr Gln Thr Pro Ser Ser Leu Ser Ala Ser Leu Gly
1               5                   10                  15

Asp Arg Val Thr Ile Ser Cys
            20
```

<210> SEQ ID NO 116
<211> LENGTH: 5
<212> TYPE: PRT
<213> ORGANISM: Artificial sequence
<220> FEATURE:
<223> OTHER INFORMATION: synthetic heavy chain variable region CDR1 of
      4F1 monoclonal antibody

<400> SEQUENCE: 116

```
Asn Tyr Leu Ile Glu
1               5
```

<210> SEQ ID NO 117
<211> LENGTH: 17
<212> TYPE: PRT
<213> ORGANISM: Artificial sequence
<220> FEATURE:
<223> OTHER INFORMATION: synthetic heavy chain variable region CDR2 of
      4F1 monoclonal antibody

<400> SEQUENCE: 117

```
Val Ile Asn Pro Gly Thr Gly Gly Thr Asn Tyr Asn Lys Lys Phe Lys
1               5                   10                  15

Val
```

<210> SEQ ID NO 118
<211> LENGTH: 13
<212> TYPE: PRT
<213> ORGANISM: Artificial sequence
<220> FEATURE:
<223> OTHER INFORMATION: synthetic heavy chain variable region CDR3 of
      4F1 monoclonal antibody

<400> SEQUENCE: 118

```
Glu Gly Asn Ala Arg Thr Tyr Tyr Tyr Ala Met Asp Tyr
1               5                   10
```

<210> SEQ ID NO 119
<211> LENGTH: 11
<212> TYPE: PRT
<213> ORGANISM: Artificial sequence
<220> FEATURE:
<223> OTHER INFORMATION: synthetic light chain variable region CDR1 of
      4F1 monoclonal antibody

<400> SEQUENCE: 119

```
Arg Ala Ser Glu Asn Ile Tyr Ser Tyr Leu Val
1               5                   10
```

```
<210> SEQ ID NO 120
<211> LENGTH: 7
<212> TYPE: PRT
<213> ORGANISM: Artificial sequence
<220> FEATURE:
<223> OTHER INFORMATION: synthetic light chain variable region CDR2 of
      4F1 monoclonal antibody

<400> SEQUENCE: 120

Asn Ala Lys Thr Leu Ala Glu
1               5

<210> SEQ ID NO 121
<211> LENGTH: 9
<212> TYPE: PRT
<213> ORGANISM: Artificial sequence
<220> FEATURE:
<223> OTHER INFORMATION: synthetic light chain variable region CDR3 of
      4F1 monoclonal antibody

<400> SEQUENCE: 121

Gln His His Asn Gly Thr Pro Tyr Thr
1               5

<210> SEQ ID NO 122
<211> LENGTH: 5
<212> TYPE: PRT
<213> ORGANISM: Artificial sequence
<220> FEATURE:
<223> OTHER INFORMATION: synthetic homologous murine region of human
      integrin beta8 including 6B9 and 4F1 epitope

<400> SEQUENCE: 122

Val Gly Thr Ser Pro
1               5

<210> SEQ ID NO 123
<211> LENGTH: 5
<212> TYPE: PRT
<213> ORGANISM: Artificial sequence
<220> FEATURE:
<223> OTHER INFORMATION: synthetic region of human integrin beta8
      including 6B9 and 4F1 epitope

<400> SEQUENCE: 123

Ile Arg Ile Asn Ser
1               5

<210> SEQ ID NO 124
<211> LENGTH: 5
<212> TYPE: PRT
<213> ORGANISM: Artificial sequence
<220> FEATURE:
<223> OTHER INFORMATION: synthetic region of human integrin beta8
      including 6B9 and 4F1 epitope with amino acid swapping

<400> SEQUENCE: 124

Val Arg Ile Asn Ser
1               5

<210> SEQ ID NO 125
<211> LENGTH: 5
<212> TYPE: PRT
<213> ORGANISM: Artificial sequence
<220> FEATURE:
<223> OTHER INFORMATION: synthetic region of human integrin beta8
      including 6B9 and 4F1 epitope with amino acid swapping

<400> SEQUENCE: 125
```

```
Ile Gly Ile Asn Pro
1               5

<210> SEQ ID NO 126
<211> LENGTH: 5
<212> TYPE: PRT
<213> ORGANISM: Artificial sequence
<220> FEATURE:
<223> OTHER INFORMATION: synthetic region of human integrin beta8
      including 6B9 and 4F1 epitope with amino acid swapping

<400> SEQUENCE: 126

Ile Gly Ile Asn Ser
1               5

<210> SEQ ID NO 127
<211> LENGTH: 6
<212> TYPE: PRT
<213> ORGANISM: Artificial sequence
<220> FEATURE:
<223> OTHER INFORMATION: synthetic region of human integrin beta8
      including 37E1B5, 14E5 and 11E8 epitope

<400> SEQUENCE: 127

Arg Lys Met Ala Phe Phe
1               5

<210> SEQ ID NO 128
<211> LENGTH: 6
<212> TYPE: PRT
<213> ORGANISM: Artificial sequence
<220> FEATURE:
<223> OTHER INFORMATION: synthetic homologous murine region of human
      integrin beta8 including 37E1B5, 14E5 and 11E8 epitope

<400> SEQUENCE: 128

Lys Lys Met Ala Leu Tyr
1               5

<210> SEQ ID NO 129
<211> LENGTH: 6
<212> TYPE: PRT
<213> ORGANISM: Artificial sequence
<220> FEATURE:
<223> OTHER INFORMATION: synthetic region of human integrin beta8
      including 37E1B5, 14E5 and 11E8 epitope with amino acid swapping

<400> SEQUENCE: 129

Arg Lys Met Ala Leu Tyr
1               5

<210> SEQ ID NO 130
<211> LENGTH: 6
<212> TYPE: PRT
<213> ORGANISM: Artificial sequence
<220> FEATURE:
<223> OTHER INFORMATION: synthetic region of human integrin beta8
      including 37E1B5, 14E5 and 11E8 epitope with amino acid swapping

<400> SEQUENCE: 130

Arg Lys Met Ala Phe Tyr
1               5

<210> SEQ ID NO 131
<211> LENGTH: 6
<212> TYPE: PRT
<213> ORGANISM: Artificial sequence
```

-continued

```
<220> FEATURE:
<223> OTHER INFORMATION: synthetic region of human integrin beta8
      including 37E1B5, 14E5 and 11E8 epitope with amino acid swapping

<400> SEQUENCE: 131

Lys Lys Met Ala Phe Tyr
1               5

<210> SEQ ID NO 132
<211> LENGTH: 6
<212> TYPE: PRT
<213> ORGANISM: Artificial sequence
<220> FEATURE:
<223> OTHER INFORMATION: synthetic region of human integrin beta8
      including 37E1B5, 14E5 and 11E8 epitope with amino acid swapping

<400> SEQUENCE: 132

Lys Lys Met Ala Leu Phe
1               5

<210> SEQ ID NO 133
<211> LENGTH: 6
<212> TYPE: PRT
<213> ORGANISM: Artificial sequence
<220> FEATURE:
<223> OTHER INFORMATION: synthetic region of human integrin beta8
      including 37E1B5, 14E5 and 11E8 epitope with amino acid swapping

<400> SEQUENCE: 133

Lys Lys Met Ala Phe Phe
1               5

<210> SEQ ID NO 134
<211> LENGTH: 6
<212> TYPE: PRT
<213> ORGANISM: Artificial sequence
<220> FEATURE:
<223> OTHER INFORMATION: synthetic region of human integrin beta8
      including 37E1B5, 14E5 and 11E8 epitope with amino acid swapping

<400> SEQUENCE: 134

Arg Lys Met Ala Leu Phe
1               5

<210> SEQ ID NO 135
<211> LENGTH: 115
<212> TYPE: PRT
<213> ORGANISM: Artificial sequence
<220> FEATURE:
<223> OTHER INFORMATION: synthetic heavy chain variable region (VH) of
      14E5Mut93 monoclonal antibody

<400> SEQUENCE: 135

Glu Val Gln Leu Gln Gln Ser Gly Ala Glu Leu Met Lys Pro Gly Ser
1               5                   10                  15

Ser Val Lys Ile Ser Cys Lys Ala Thr Gly Tyr Thr Phe Ser Thr Tyr
            20                  25                  30

Trp Ile Glu Trp Ile Lys Gln Arg Pro Gly His Gly Leu Glu Trp Ile
        35                  40                  45

Gly His Ile Leu Pro Gly Ser Val Ile Thr Asn Tyr Asn Glu Lys Phe
    50                  55                  60

Lys Gly Lys Ala Ala Ile Thr Ala Asp Thr Ser Ser Asn Thr Ser Tyr
65                  70                  75                  80

Met Gln Leu Ser Ser Leu Thr Ser Glu Asp Ser Ala Val Tyr Tyr Cys
                85

```
Ala Arg Trp Gly Trp Asp Ser Tyr Trp Gly Gln Gly Thr Leu Val Thr
            100                 105                 110

Val Ser Ser
        115

<210> SEQ ID NO 136
<211> LENGTH: 108
<212> TYPE: PRT
<213> ORGANISM: Artificial sequence
<220> FEATURE:
<223> OTHER INFORMATION: synthetic light chain variable region (VK) of
      14E5Mut93 monoclonal antibody

<400> SEQUENCE: 136

Asp Ile Met Met Thr Gln Ser Pro Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Asn Leu Pro Tyr
                85                  90                  95

Thr Phe Gly Gly Gly Thr Lys Leu Glu Ile Lys Arg
            100                 105
```

ANTIBODIES THAT BIND INTEGRIN ALPHA-V BETA-8

CROSS REFERENCES TO RELATED APPLICATIONS

This application is the US National Stage of PCT/US2010/051373, Aug. 17, 2012, claims priority to U.S. Provisional Patent Application No. 61/524,708, filed Aug. 17, 2011 and U.S. Provisional Patent Application No. 61/646,111, filed May 11, 2012, the disclosures of which are incorporated by reference in their entirety.

STATEMENT AS TO RIGHTS TO INVENTIONS MADE UNDER FEDERALLY SPONSORED RESEARCH AND DEVELOPMENT

This invention was made with Government support under Grant No. HL63993 and NS-44155 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 81906-900711_ST25.txt, created on May 30, 2014, 82,342 bytes, machine format IBM-PC, MS-Windows operating system, is hereby incorporated by reference.

BACKGROUND OF THE INVENTION

The multifunctional cytokine transforming growth factor-β (TGF-β) affects immune, endothelial, epithelial, and mesenchymal cells during development and adult life in invertebrate and vertebrate species. In mammals, these functions are mediated by three widely expressed isoforms, TGF-β1, 2, and 3. All three isoforms interact with the same cell surface receptors (TGFBR2 and ALK5) and signal through the same intracellular signaling pathways, which involve either canonical (i.e., SMADs) or noncanonical (i.e., MAPK, JUN, PI3K, PP2A, Rho, PAR6) signaling effectors. In the canonical TGF-β signaling pathway, the signal is propagated from the TGF-β receptor via phosphorylation of cytoplasmic SMAD-2/3, complex formation with SMAD-4, translocation of the SMAD-2/3/4 complex to the nucleus, and binding to SMAD response elements located in the promoter regions of many genes involved in the fibrogenic response. While the TGF-β isoforms have similar signaling partners, each serves distinct biological functions. The TGF-β isoforms have differences in binding affinities to TGF-β receptors, activation mechanism, signaling intensity or duration, or spatial and/or temporal distribution.

Knockout and conditional deletion models of TGF-β isoforms, receptors, and signaling mediators, as well as function-blocking reagents targeting all TGF-β isoforms, have revealed essential roles for TGF-β in T-cell, cardiac, lung, vascular, and palate development. Mice deficient in TGF-β1 either die in utero, owing to defects in yolk sac vasculogenesis, or survive to adulthood with severe multi-organ autoimmunity. Genetic deletion of TGF-β signaling mediator Smad2 reveals that it is essential in early patterning and mesodermal formation. Mice lacking Smad3 are viable and fertile, but exhibit limb malformations, immune dysregulation, colitis, colon carcinomas, and alveolar enlargement. In adult tissues, the TGF-β pathway is involved in the immune, mesenchymal, and epithelial cell interactions to maintain homeostasis in response to environmental stress.

The homeostatic pathways mediated by TGF-β are perturbed in response to chronic repetitive injury. TGF-β is a major profibrogenic cytokine in response to injury, delaying epithelial wound healing. TGF-β inhibits epithelial proliferation and migration, promotes apoptosis, and expands the mesenchymal compartment by inducing fibroblast recruitment, fibroblast contractility, and extracellular matrix deposition. Intratracheal transfer of adenoviral recombinant TGF-β1 to the rodent lung dramatically increases fibroblast accumulation and expression of type I and type III collagen around airways and in the pulmonary interstitium. Neutralizing anti-TGF-β antibodies can block bleomycin or radiation-induced pulmonary fibrosis.

Increased TGF-β activity can play a role in fibrotic lung disease, glomerulosclerosis, and restenosis of cardiac vessels, primarily mediated by TGF-β1. TGF-β1 function in humans is complex, as indicated by hereditary disorders involving either TGF-β1 itself or its signaling effectors. Mutations that increase the activity of the TGF-β pathway lead to defects in bone metabolism (ie, Camurati-Engelmann disease), in connective tissue (ie, Marfan syndrome), and in aortic aneurysms (ie, Loeys-Dietz syndrome). Mutations that lead to decreased activity of the TGF-β pathway correlate with cancer. The role of TGF-β as a tumor suppressor in cancer is not straightforward, however, because TGF-β can also enhance tumor growth and metastasis.

Despite the multiple essential functions of TGF-β, a single dose or short-term administration of a pan-TGF-β neutralizing antibody is well tolerated. No side effects are observed in rodents at doses that inhibit organ fibrosis or carcinoma cell growth and metastasis. This treatment also effectively inhibits experimental fibrosis. Single-dose phase I/II clinical trials using neutralizing pan-TGF-β antibodies are ongoing for metastatic renal cell carcinoma, melanoma, focal segmental glomerulosclerosis, and idiopathic pulmonary fibrosis (Genzyme Corporation, available at genzymeclinicalresearch.com).

BRIEF SUMMARY OF THE INVENTION

Provided herein are antibody compositions that can be used for diagnosis and treatment of disorders associated with elevated TGF-β activity mediated by αvβ8. In some embodiments, provided is an isolated antibody that specifically binds αvβ8, wherein the isolated antibody inhibits release of active, mature TGFβ peptide, but does not significantly inhibit adhesion of latent TGFβ to αvβ8 on a αvβ8-expressing cell, and wherein the isolated antibody binds fixed αvβ8-expressing cells (e.g., formalin fixed). The antibody with these activities is referred to as 11E8, which term includes affinity-matured, humanized, chimeric, and labeled versions of the 11E8 antibodies, as well as αvβ8-binding fragments thereof. In some embodiments, the isolated antibody specifically binds to an epitope on β8 that is within SEQ ID NO:1. In some embodiments, the antibody comprises the heavy chain CDRs shown in SEQ ID NO:10 (SEQ ID NOs:48, 49, and 50). In some embodiments, the antibody comprises the light chain CDRs shown in SEQ ID NO:11 (SEQ ID NOs:51, 52, and 53). In some embodiments, the antibody comprises the heavy chain CDRs shown in SEQ ID NO:10 and the light chain CDRs shown in SEQ ID NO:11. In some embodiments, the antibody comprises the heavy chain variable region shown in SEQ ID NO:10. In some embodiments, the antibody comprises the light chain variable region shown in SEQ ID NO:11. In some embodiments, the antibody comprises the heavy chain variable region shown in SEQ ID NO:10 and the light chain variable region shown in SEQ ID NO:11. In some embodiments, the antibody comprises the heavy chain CDRs and light chain CDRs of 11E8Mut28. In some embodiments, the antibody comprises the heavy chain heavy chain sequence and light chain variable region sequence of 11E8Mut28. In some embodiments, the antibody comprises the heavy chain CDRs and light chain CDRs of 11E8Mut94. In some embodiments, the antibody comprises the heavy chain variable region sequence and light chain variable region sequence of 11E8Mut94. In some embodiments, the antibody comprises the heavy chain CDRs and light chain CDRs of 11E8Mut39. In some embodiments, the antibody comprises the heavy chain variable region sequence and light chain variable region sequence of 11E8Mut39. In some embodiments, the isolated antibody binds to the β8 epitope with high affinity, e.g., with higher affinity than the anti-αvβ8 antibody 37E1, with an affinity in the nanomolar or picomolar range, or with a Kd of $10^{-7}$, $10^{-8}$, $10^{-9}$ or lower. In some embodiments, the isolated antibody is less than 50 kD, less than 25 kD, or is a single chain antibody (e.g., scFv). In some embodiments, the anti-αvβ8 antibody 37E1 or 37E1B5 competes with the 11E8 antibody for binding to αvβ8 on a αvβ8-expressing cell. Also provided is a pharmaceutical composition comprising the isolated antibody described here and a pharmaceutical excipient.

Further provided is a humanized antibody that specifically binds αvβ8, wherein the isolated antibody inhibits release of active, mature TGFβ peptide, but does not significantly inhibit adhesion of latent TGFβ to αvβ8 on a αvβ8-expressing cell. The antibody with this activity is referred to as h37E1B5 (humanized 37E1B5 or Hu37E1B5), which term refers to labeled h37E1B5 and αvβ8-binding fragments thereof. In some embodiments, the humanized antibody specifically binds to an epitope on β8 that is within SEQ ID NO:1. In some embodiments, the humanized antibody binds to the β8 epitope with high affinity, e.g., with higher affinity than the anti-αvβ8 antibody 37E1, with an affinity in the nanomolar or picomolar range, or with a Kd of $10^{-7}$, $10^{-8}$, $10^{-9}$ or lower. In some embodiments, the isolated antibody is less than 50 kD, less than 25 kD, or is a single chain antibody (e.g., scFv). In some embodiments, the humanized antibody comprises a heavy chain variable region of SEQ ID NO:8 and a light chain variable region of SEQ ID NO:9. In some embodiments, the humanized antibody has a heavy chain variable region of SEQ ID NO:8 and a light chain variable region of SEQ ID NO:9. Also provided is a pharmaceutical composition comprising the humanized antibody described here and a pharmaceutical excipient.

Also provided are antibody compositions that can be used for diagnosis of disorders associated with elevated TGF-β activity mediated by αvβ8. In some embodiments, provided is an isolated antibody that specifically binds αvβ8, wherein the antibody does not inhibit release of active, mature TGFβ peptide or adhesion of latent TGFβ to αvβ8 on a αvβ8-expressing cell, wherein the isolated antibody binds fixed (e.g., formalin fixed) αvβ8-expressing cells or tissue, and wherein the antibody distinguishes αvβ8 expression levels in the cell or tissue (e.g., the antibody can be used to compare αvβ8 expression levels on different cells). Antibodies with these activities are referred to as 6B9 and 4F1, which includes affinity-matured, humanized, chimeric, and labeled versions of the 6B9 and 4F1 antibodies, as well as αvβ8-binding fragments thereof. In some embodiments, the isolated antibody specifically binds to an epitope on β8 that is within SEQ ID NO:14. In some embodiments, the epitope includes S95 of human β8, the full length sequence of which is shown in SEQ ID NO:17. In some embodiments, the antibody comprises the heavy chain CDRs shown in SEQ ID NO:18. In some embodiments, the antibody comprises the light chain CDRs shown in SEQ ID NO:19. In some embodiments, the antibody comprises the heavy chain CDRs shown in SEQ ID NO:18 and the light chain CDRs shown in SEQ ID NO:19. In some embodiments, the antibody comprises the heavy chain variable region shown in SEQ ID NO:18. In some embodiments, the antibody comprises the light chain variable region shown in SEQ ID NO:19. In some embodiments, the antibody comprises the heavy chain variable region shown in SEQ ID NO:18 and the light chain variable region shown in SEQ ID NO:19. In some embodiments, the antibody comprises the heavy chain CDRs and light chain CDRs of 6B9Mut1. In some embodiments, the antibody comprises the heavy chain variable region sequence and light chain variable region sequence of 6B9Mut1. In some embodiments, the antibody comprises the heavy chain CDRs shown in SEQ ID NO:20. In some embodiments, the antibody comprises the light chain CDRs shown in SEQ ID NO:21. In some embodiments, the antibody comprises the heavy chain CDRs shown in SEQ ID NO:20 and the light chain CDRs shown in SEQ ID NO:21. In some embodiments, the antibody comprises the heavy chain variable region shown in SEQ ID NO:20. In some embodiments, the antibody comprises the light chain variable region shown in SEQ ID NO:21. In some embodiments, the antibody comprises the heavy chain variable region shown in SEQ ID NO:20 and the light chain variable region shown in SEQ ID NO:21. In some embodiments, the isolated antibody binds to the β8 epitope with high affinity, e.g., with an affinity in the nanomolar or picomolar range, or with a Kd of $10^{-7}$, $10^{-8}$, $10^{-9}$ or lower. In some embodiments, the isolated antibody is less than 50 kD, less than 25 kD, or is a single chain antibody (e.g., scFv). In some embodiments, the anti-αvβ8 antibody 6B9 or 4F1 do not compete for binding with the 37E1, 37E1B5, or 11E8 antibody for binding to αvβ8 on a αvβ8-expressing cell. Also provided is a pharmaceutical composition comprising the isolated antibodies described here and a pharmaceutical excipient.

Provided herein are methods of reducing TGFβ signaling (reducing TGFβ activity, reducing release of mature active TGFβ) in an individual, comprising administering the pharmaceutical composition comprising the 11E8 or h37E1B5 antibody (as described above) to the individual, thereby reducing TGFβ signaling in the individual. In some embodiments, the individual has at least one condition (disease, disorder) selected from the group consisting of inflammatory bowel disease (IBD), chronic obstructive pulmonary disease (COPD), asthma, arthritis, hepatic fibrosis, a pulmonary fibrotic disorder, an inflammatory brain autoimmune disease, multiple sclerosis, a demyelinating disease, neuroinflammation, kidney disease, adenocarcinoma, squamous carcinoma, glioma, and breast carcinoma; and reducing TGFβ signaling results in amelioration of the condition.

Further provided are methods of diagnosing a αvβ8 associated disorder in an individual, comprising contacting a cell from the individual with the 11E8, 6B9, or 4F1 antibody as described above, and detecting binding of the isolated antibody to the cell, wherein binding of the isolated antibody to the cell indicates that the individual has the αvβ8 associated disorder. In some embodiments, the αvβ8 associated disorder is selected from the group consisting of inflammatory bowel disease (IBD), chronic obstructive pulmonary disease (COPD), asthma, arthritis, hepatic fibrosis, a pulmonary fibrotic disorder, an inflammatory brain autoimmune disease, multiple sclerosis, a demyelinating disease, neuroinflammation, kidney disease, adenocarcinoma, squamous carcinoma, glioma, and breast carcinoma. In some embodiments (e.g., in vitro diagnostic techniques), the cell is fixed. In some embodiments, the αvβ8 associated disorder is IBD, and the cell is obtained from the bowel (e.g., colon or intestine) of the individual. In some embodiments, the αvβ8 associated disorder is arthritis and the cell is a chondrocyte or cartilage cell from the individual. In some embodiments, the αvβ8 associated disorder is hepatic fibrosis, and the cell is a hepatic stellate cell from the individual. In some embodiments, the αvβ8 associated disorder is asthma, COPD, or pulmonary fibrosis, and the cell is obtained from the airway of the individual. In some embodiments, the method further comprises administering a pharmaceutical composition (comprising the 11E8, 37E1B5, or h37E1B5 antibody) to the individual.

Further provided are methods of determining the relative level of αvβ8 expression on a test cell. In some embodiments, the method comprises contacting the test cell with a 6B9 antibody, detecting 6B9 antibody binding to the test cell, and comparing the level of 6B9 antibody binding to that of a control cell, thereby determining the relative level of αvβ8 expression on the test cell. In some embodiments, the method comprises contacting the test cell with a 4F1 antibody, detecting 4F1 antibody binding to the test cell, and comparing the level of 4F1 antibody binding to that of a control cell, thereby determining the relative level of αvβ8 expression on the test cell. In some embodiments, the test cell is fixed (e.g., formalin fixed). In some embodiments, the control cell is fixed. In some embodiments, the control cell is a wild type, non-cancer cell. In some embodiments, the control cell is a healthy cell (from an individual not suffering from a αvβ8 related disorder). In some embodiments, the expression level is indicative of the genomic β8 copy number in the cell, e.g., so that a higher relative expression level than a non-cancer control indicates that the test cell has an increased genomic β8 copy number. In some embodiments, the test cell is in a biological sample from an individual (e.g., an in vitro fluid or tissue sample). In some embodiments, the test cell is in situ in the individual. In some embodiments, the method further comprises diagnosing the individual with a αvβ8 associated disorder (as described herein) when αvβ8 expression is higher than normal in the test cell. One of skill will understand that a control cell can be from a healthy individual (e.g., representative of normal expression levels), or can be a positive control, e.g., known to have elevated αvβ8 expression, or from an individual with a αvβ8 associated disorder.

Additionally provided is an isolated antibody that specifically binds to αvβ8, wherein said antibody does not inhibit release of active, mature TGFβ peptide or adhesion of latent TGFβ to αvβ8 on a αvβ8-expressing cell. In some embodiments, the isolated antibody specifically binds to an epitope on β8 that is within SEQ ID NO:1. The antibody with these activities is referred to as 14E5, which term includes affinity-matured, humanized, chimeric, and labeled versions of the 14E5 antibodies, as well as αvβ8-binding fragments thereof. In some embodiments, the antibody comprises the heavy chain CDRs shown in SEQ ID NO:12. In some embodiments, the antibody comprises the light chain CDRs shown in SEQ ID NO:13. In some embodiments, the antibody comprises the heavy chain CDRs shown in SEQ ID NO:12 and the light chain CDRs shown in SEQ ID NO:13. In some embodiments, the antibody comprises the heavy chain CDRs and light chain CDRs of an affinity-matured antibody selected from the group consisting of: 14E5Mut11, 14E5Mut42, 14E5Mut54, 14E5Mut68, 14E5Mut65, 14E5Mut83, and 14E5Mut95. In some embodiments, the antibody comprises the heavy chain variable region shown in SEQ ID NO:12. In some embodiments, the antibody comprises the light chain variable region shown in SEQ ID NO:13. In some embodiments, the antibody comprises the heavy chain variable region shown in SEQ ID NO:12 and the light chain variable region shown in SEQ ID NO:13. In some embodiments, the antibody comprises the heavy chain variable region sequence and light chain variable region sequence of an affinity-matured antibody selected from the group consisting of: 14E5Mut11, 14E5Mut42, 14E5Mut54, 14E5Mut68, 14E5Mut65, 14E5Mut83, and 14E5Mut95. In some embodiments, the isolated antibody binds to the β8 epitope with high affinity, e.g., with higher affinity than the anti-αvβ8 antibody 37E1, with an affinity in the nanomolar or picomolar range, or with a Kd of $10^{-7}$, $10^{-8}$, $10^{-9}$ or lower. In some embodiments, the isolated antibody is less than 50 kD, less than 25 kD, or is a single chain antibody (e.g., scFv). In some embodiments, the anti-αvβ8 antibody 37E1 or 37E1B5 competes with the 14E5 antibody for binding to αvβ8 on a αvβ8-expressing cell.

Provided are methods for detecting the presence of a αvβ8-expressing cell comprising contacting a cell with the 14E5 antibody, and determining whether the antibody binds to the cell, wherein antibody binding to the cell indicates the presence of an αvβ8-expressing cell. In some embodiments, the contacting is in vivo. In some embodiments, the contacting is in vitro.

Such methods can be used in methods of diagnosing an αvβ8 associated disorder in an individual, comprising contacting a cell from the individual with the 14E5 antibody as described above, and detecting binding of the isolated antibody to the cell, wherein binding of the isolated antibody to the cell indicates that the individual has the αvβ8 associated disorder. In some embodiments, the αvβ8 associated disorder is selected from the group consisting of inflammatory bowel disease (IBD), chronic obstructive pulmonary disease (COPD), asthma, arthritis, hepatic fibrosis, a pulmonary fibrotic disorder, an inflammatory brain autoimmune disease, multiple sclerosis, a demyelinating disease, neuroinflammation, kidney disease, adenocarcinoma, squamous carcinoma, glioma, and breast carcinoma. In some embodiments, the αvβ8 associated disorder is IBD, and the cell is obtained from the bowel (e.g., colon or intestine) of the individual. In some embodiments, the αvβ8 associated disorder is arthritis and the cell is a chondrocyte or cartilage cell from the individual. In some embodiments, the αvβ8 associated disorder is hepatic fibrosis, and the cell is a hepatic stellate cell from the individual. In some embodiments, the αvβ8 associated disorder is asthma, COPD, or pulmonary fibrosis, and the cell is obtained from the airway of the individual. In some embodiments, the method further comprises administering a pharmaceutical composition (comprising the 11E8, 37E1B5, or h37E1B5 antibody) to the individual.

BRIEF DESCRIPTION OF THE DRAWINGS

FIG. 1 shows alignment of the heavy and light chain variable regions for 37E1, 37E1B5, and humanized 37E1B5 antibodies. CDR and framework sequences are indicated.

FIG. 3 shows expression of β8 on lung alveolar macrophages, dendritic cells, mediastinal lymph node cells, T and B cells and provides a summary of staining data in other organs. A) Lung macrophages: autofluorescent+, CD11Chi+, F480+, CD8+, CD11B−, Ly6G−, CD103−, Ly6C+/−, TCR−; B) Lung dendritic cells: autofluorescent−, CD11C intermed+, F480 (mostly negative), CD8+, CD11B+, CD103−/+, Ly6C+/−, TCR−, Ly6G−, GR-1− C) C) Lung T cells-TCR αβ+, CD3+, B220−, Class II−, CD19−, non-auto fluorescent; D) Lung B cells-TCR αβ−, CD3−, B220+, Class II+, CD19+, non-auto fluorescent; E) MLN dendritic cells: autofluorescent−, CD11C intermed+, CD11B+, Class II MHC hi, F480−, Ly6C+/−, Ly6G− (probably CD8+, CD103+/−, GR-1+/−); F) MLN B cells-TCR αβ−, CD3−, B220+, Class II+, CD19+, non-auto fluorescent; G) Summary table of staining data in multiple organs. Staining was performed using hybridoma clone 14E5.

FIGS. 11A-B: Heavy chain variable sequence for a variety of discovered antibodies and subsequent affinity matured variants (with "Mut" in designation). Bold and underlined amino acids indicate changes from the original ("wt") antibody heavy chain variable region sequences.

FIGS. 12A-B: Light chain variable sequence for a variety of discovered antibodies and subsequent affinity matured variants (with "Mut" in designation). Bold and underlined amino acids indicate changes from the original ("wt") antibody light chain variable region sequences.

DETAILED DESCRIPTION OF THE INVENTION

I. Introduction

Figure 2:
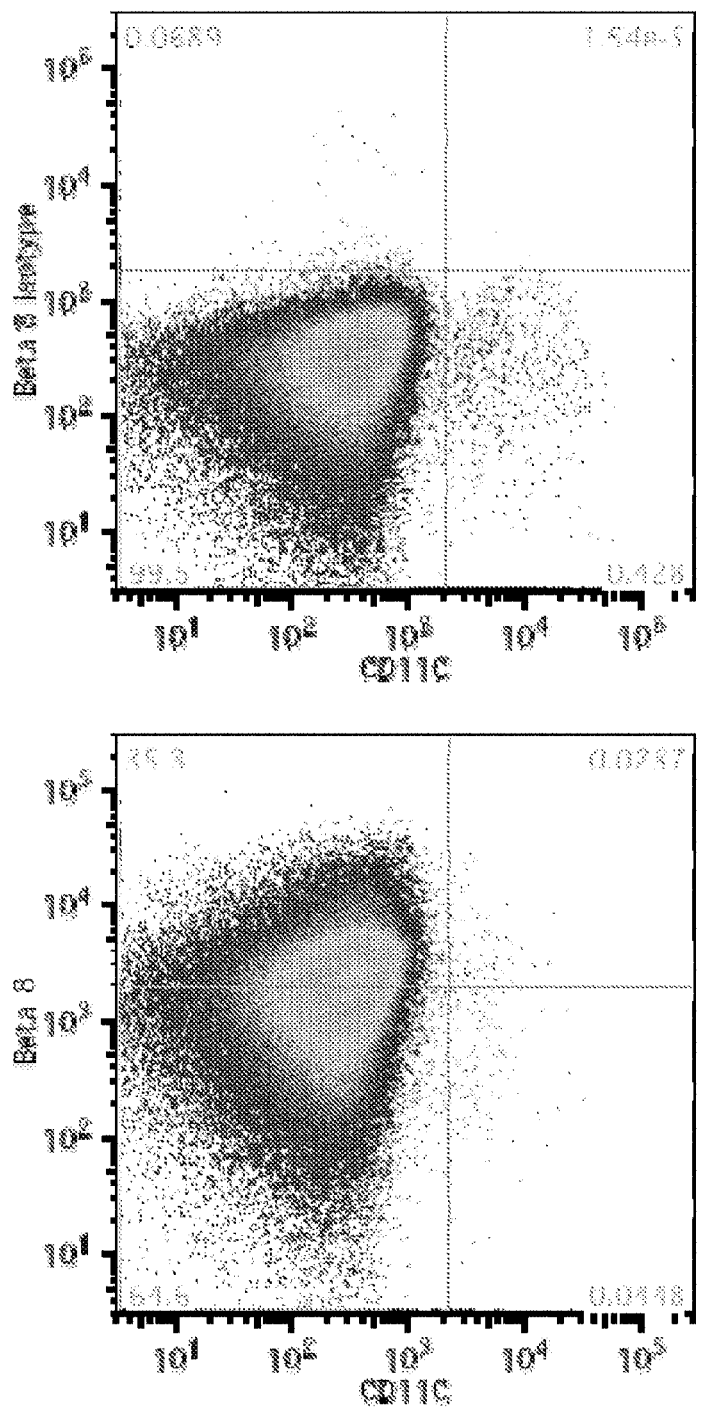
FIG. 2 shows expression of human β8 on hepatic stellate cells in ITGB8 transgenic mice. The top panel shows isotype control, while the bottom panel shows β8 expression, determined using the 14E5 antibody.

Transforming growth factor β (TGFβ) was originally characterized as an oncogene capable of inducing a transformed phenotype in non-neoplastic cells. A number of TGFβ family members have since been characterized, based on the presence of similar amino acid domains.

Some TGF-β isoforms are expressed ubiquitously in mammals (TGF-β1-3), but are maintained in an inactive form by non-covalent interaction with a propeptide, the latency associated domain of TGF-β (LAP). For TGFβ to signal, it must be released from its inactive complex by a process called TGFβ activation. The latent TGF complex includes 3 components: the active (mature) TGFβ dimmer, LAP (latency associated peptide) and LTBP (latent TGFβ binding protein). LAP is a dimer, linked by a disulfide bond, that represents the N-terminal end of the TGFβ precursor protein. The mature TGFβ protein represents the C terminal end (about 25 kD) of the precursor. The bond between the TGFβs and LAP is proteolytically cleaved within the Golgi, but the TGF-β propeptide remains bound to TGFβ by non-covalent interactions. The complex of TGFβ and LAP is called the small latent complex (SLC). It is the association of LAP and TGFβ that confers latency. LAP-TGFβ binding is reversible and the isolated purified components can recombine to form an inactive SLC. Both the SLC and the larger complex are referred to herein as latent TGFβ, as both are inactive.

In general, integrins are adhesion molecules and mediate the attachment of cells to extracellular matrix proteins. Integrin αvβ8 binds to the LAP of TGF-β and mediates the activation of TGF-β1 and 3 (Mu et al. (2002) *J. Cell Biol.* 159:493). Integrin αvβ8-mediated activation of TGF-β is required for in vivo activation of TGF-β (i.e., release of the mature TGF-β polypeptide), thus αvβ8 is a gatekeeper of TGF-β function. Integrin αvβ8 is expressed in normal epithelia (e.g., airway epithelia), mesenchymal cells, and neuronal tissues. The results shown herein indicate that integrin αvβ8-mediated activation of TGF-β can result in COPD, pulmonary fibrosis, arthritis, inflammatory bowel disease, hepatic and renal fibrosis, inflammatory brain autoimmune diseases and demylinating disesases (e.g., MS, transverse myelitis, Devic's disease, Guillain-Barré syndrome), neuroinflammation, kidney disease, and cancer growth and metastasis.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

The terms "anti-αvβ8 antibody," "αvβ8 specific antibody," "αvβ8 antibody," and "anti-αvβ8" are used synonymously herein to refer to an antibody that specifically binds to αvβ8. Similarly, an anti-β8 antibody (and like terms) refer to an antibody that specifically binds to β8. The anti-αvβ8 antibodies and anti-β8 antibodies described herein bind to the protein expressed on αvβ8 expressing cells.

A fixed cell is one that has been treated to inhibit cell metabolism and preserve the cell for characterization. Fixation is commonly practiced in the art, e.g., to observe cytological characteristics by histology, or to observe cell surface marker expression by immunostaining and/or flow cytometry. One of skill will understand that a cell can be fixed in any of a number of known fixation solutions comprising, e.g., formalin, formaldehyde, paraformaldehyde, methanol, acetone, etc. Tissues can be fixed in a similar fashion.

An αvβ8-associated disorder is a condition characterized by the presence of αvβ8-expressing cells, either cells expressing an increased level of αvβ8, or increased number of αvβ8-expressing cells relative to a normal, non-diseased control. TGFβ-associated disorders (disorders characterized by higher than normal TGFβ activity) include αvβ8-associated disorders, as αvβ8 is involved in activating TGFβ in certain circumstances, as described herein.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. As described below, the algorithms can account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "antibody" refers to a polypeptide comprising a framework region from an immunoglobulin gene, or fragments thereof, that specifically bind and recognize an antigen, e.g., β8, a particular cell surface marker, or any desired target. Typically, the "variable region" contains the antigen-binding region of the antibody (or its functional equivalent) and is most critical in specificity and affinity of binding. See Paul, Fundamental Immunology (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities.

As used herein, "V-region" refers to an antibody variable region domain comprising the segments of Framework 1, CDR1, Framework 2, CDR2, Framework 3, CDR3, and Framework 4. These segments are included in the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, (1987) J. Mol. Biol. 196, 901-917; Chothia et al. (1989) Nature 342, 877-883; Chothia et al. (1992) J. Mol. Biol. 227, 799-817; Al-Lazikani et al., J. Mol. Biol 1997, 273(4)). Definitions of antigen combining sites are also described in the following: Ruiz et al. Nucleic Acids Res., 28, 219-221 (2000); and Lefranc Nucleic Acids Res. January 1; 29(1):207-9 (2001); MacCallum et al., J. Mol. Biol., 262: 732-745 (1996); and Martin et al, Proc. Natl Acad. Sci. USA, 86, 9268-9272 (1989); Martin, et al, Methods Enzymol., 203: 121-153, (1991); Pedersen et al, Immunomethods, 1, 126, (1992); and Rees et al, In Sternberg M. J. E. (ed.), Protein Structure Prediction. Oxford University Press, Oxford, 141-172 1996).

A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

The antibody binds to an "epitope" on the antigen. The epitope is the specific antibody binding interaction site on the antigen, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The term "specifically bind" refers to a molecule (e.g., antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, an antibody that specifically binds β8 will typically bind to β8 with at least a 2-fold greater affinity than a non-β8 target (e.g., a different integrin subunit, e.g., β6).

The term "binds" with respect to a cell type (e.g., an antibody that binds fibrotic cells, hepatocytes, chondrocytes, etc.), typically indicates that an agent binds a majority of the cells in a pure population of those cells. For example, an antibody that binds a given cell type typically binds to at least ⅔ of the cells in a population of the indicated cells (e.g., 75, 80, 85, 90, 91, 92, 93, 94, 95, 96, 97, 98, 99, or 100%). One of skill will recognize that some variability will arise depending on the method and/or threshold of determining binding.

As used herein, a first antibody, or an antigen-binding portion thereof, "competes" for binding to a target with a second antibody, or an antigen-binding portion thereof, when binding of the second antibody with the target is detectably decreased in the presence of the first antibody compared to the binding of the second antibody in the absence of the first antibody. The alternative, where the binding of the first antibody to the target is also detectably decreased in the presence of the second antibody, can, but need not be the case. That is, a second antibody can inhibit the binding of a first antibody to the target without that first antibody inhibiting the binding of the second antibody to the target. However, where each antibody detectably inhibits the binding of the other antibody to its cognate epitope or ligand, whether to the same, greater, or lesser extent, the antibodies are said to "cross-compete" with each other for binding of their respective epitope(s). Both competing and cross-competing antibodies are encompassed by the present invention. The term "competitor" antibody can be applied to the first or second antibody as can be determined by one of skill in the art. In some cases, the presence of the competitor antibody (e.g., the first antibody) reduces binding of the second antibody to the target by at least 10%, e.g., 20%, 30%, 40%, 50%, 60%, 70%, 80%, or more, e.g., so that binding of the second antibody to target is undetectable in the presence of the first (competitor) antibody.

The term "differentially expressed" or "differentially regulated" refers generally to a protein or nucleic acid biomarker that is overexpressed (upregulated) or underexpressed (downregulated) in one sample compared to at least one other sample. In the context of the present invention, the term generally refers to overexpression of a biomarker (e.g., αvβ8) on a diseased cell compared to a normal cell.

For example, the terms "overexpressed" or "upregulated" interchangeably refer to a protein or nucleic acid, generally a biomarker, that is transcribed or translated at a detectably greater than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be 10%, 20%, 30%, 40%, 50%, 60%, 70%, 80%, 90% or more in comparison to a normal cell.

The terms "agonist," "activator," "inducer" and like terms refer to molecules that increase activity or expression as compared to a control. Agonists are agents that, e.g., bind to, stimulate, increase, activate, enhance activation, sensitize or upregulate the activity of the target. The expression or activity can be increased 10%, 20%, 30%, 40%, 50%, 60%, 70%, 80%, 90% 100% or more than that in a control. In certain instances, the activation is 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "diagnosis" refers to a relative probability that a disorder such as cancer or an inflammatory condition is present in the subject. Similarly, the term "prognosis" refers to a relative probability that a certain future outcome may occur in the subject. For example, prognosis can refer to the likelihood that an individual will develop a TGFβ or αvβ8 associated disorder, have recurrence, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, a TGFβ or αvβ8 associated disorder. In some embodiments, the sample may be a tissue biopsy, such as needle biopsy, fine needle biopsy, surgical biopsy, etc. The sample can also be a blood sample or blood fraction, e.g., white blood cell fraction, serum, or plasma. The sample can comprise a tissue sample harboring a lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

The terms "therapy," "treatment," and "amelioration" refer to any reduction in the severity of symptoms. In the case of treating an inflammatory condition, the treatment can refer to reducing, e.g., blood levels of inflammatory cytokines, blood levels of active mature TGFβ, pain, swelling, recruitment of immune cells, etc. In the case of treating cancer, treatment can refer to reducing, e.g., tumor size, number of cancer cells, growth rate, metastatic activity, cell death of non-cancer cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (no detectable symptoms remaining) or partial, such that symptoms are less frequent of severe than in a patient without the treatment described herein. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

An "inflammatory condition" refers to any inflammation in an individual, and can be transient (e.g., in response to exposure to a pathogen or allergen) or chronic. Inflammation is characterized by inflammatory cytokines such as IFN-gamma, IL-6, and TNF-alpha that recruit and activate macrophages and other leukocytes. In some cases, inflammation can develop into a chronic, harmful condition or autoimmune condition (e.g., MS, lupus, rheumatoid arthritis, Crohn's disease). Inflammation can be evident locally (e.g., at a localized site of infection or exposure) or systemically (e.g., atherosclerosis, high blood pressure). In some embodiments, the antibody compositions and methods described herein can be used to treat inflammatory conditions.

"Cancer", "tumor," "transformed" and like terms include precancerous, neoplastic, transformed, and cancerous cells, and can refer to a solid tumor, or a non-solid cancer (see, e.g., Edge et al. *AJCC Cancer Staging Manual* (7$^{th}$ ed. 2009); Cibas and Ducatman *Cytology: Diagnostic principles and clinical correlates* (3$^{rd}$ ed. 2009)). Cancer includes both benign and malignant neoplasms (abnormal growth).

"Transformation" refers to spontaneous or induced phenotypic changes, e.g., immortalization of cells, morphological changes, aberrant cell growth, reduced contact inhibition and anchorage, and/or malignancy (see, Freshney, *Culture of Animal Cells a Manual of Basic Technique* (3$^{rd}$ ed. 1994)). Although transformation can arise from infection with a transforming virus and incorporation of new genomic DNA, or uptake of exogenous DNA, it can also arise spontaneously or following exposure to a carcinogen.

The term "cancer" can refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia (AML), chronic myeloid leukemia (CML), and multiple myeloma. In some embodiments, the antibody compositions and methods described herein can be used for treating cancer.

III. Antibodies Specific for αvβ8

A. Humanized 37E1B5

Mouse monoclonal antibody 37E1 (IgG2a) selectively blocks the interaction of the human integrin αvβ8 with its ligand, transforming growth factor-β (TGF-β). The antibody is distinct in that it selectively blocks αvβ8-mediated activation of TGF-β (release of the mature TGF-β polypeptide), but does not prevent αvβ8 binding to immobilized or secreted TGF-β. This affords a high degree of selectivity in perturbing only TGF-β activation, not the cell adhesion properties of αvβ8. In addition, systemic inactivation of TGF-β is undesirable in some cases. The specific activity of the 37E1 antibody provides a targeted therapeutic tool for reducing TGF-β levels.

The heavy and light chain variable regions of 37E1 were refined to make a higher affinity antibody. FIG. 1 shows the specific amino acid substitutions that confer higher affinity for the same epitope on β8. The improved (higher affinity) antibody was named 37E1B5. It shows increased affinity in vitro and stronger efficacy in inhibiting integrin αvβ8-mediated activation of TGF-β in cultured cells. The effective therapeutic dose of the 37E1B5 antibody in vitro is in the picomolar range. A humanized version of 37E1B5, which retains high affinity binding of β8, has been generated, as shown in FIG. 1. As with the parent 37E1 and 37E1B5 antibodies, humanized 37E1B5 blocks αvβ8-mediated activation of TGF-β, but does not prevent αvβ8 binding to immobilized or secreted TGF-β.

Accordingly, provided are antibodies that have heavy chain CDRs 1-3 as found in the variable heavy chain sequences of SEQ ID NOs:4, 6, and 8. The sequences of heavy chain CDRs 1-3 are RYWMS (SEQ ID NO:94), EINPDSSTINYTSSLKD (SEQ ID NO:95), and LITTEDY (SEQ ID NO:96), respectively. Further provided are antibodies that have light chain CDRs 1-3 as found in the variable light chain sequence SEQ ID NO:5, or SEQ ID NOs:7 and 9. The sequences of light chain CDRs 1-3 from SEQ ID NO:5 are KASQDINSYL (SEQ ID NO:97), RANRLVD (SEQ ID NO:98), and LQYDEFPYT (SEQ ID NO:99). Light chain variable region sequences SEQ ID NOs:7 and 9 have the same CDR1 and CDR3 sequences as SEQ ID NO:5, but differ in CDR2 (YANRLVD, SEQ ID NO:100).

In some embodiments, provided are antibodies comprising:

a heavy chain variable region sequence comprising SEQ ID NOs:94, 95, and 96, and a light chain variable region sequence comprising SEQ ID NOs:97, 98, and 99;

a heavy chain variable region sequence comprising SEQ ID NO:94, 95, and 96, and a light chain variable region sequence comprising SEQ ID NOs:97, 100, and 99; or a heavy chain variable region sequence selected from the group consisting of SEQ ID NOs: 4, 6, and 8 and a light chain variable region sequence selected from the group consisting of SEQ ID NO:5, 7, and 9, in any combination.

In some embodiments, the antibody comprises a heavy chain variable region sequence of SEQ ID NO:8 and a light chain variable region sequence of SEQ ID NO:9.

B. 11E8

The 11E8 antibody binds a similar epitope on αvβ8 as 37E1B5, but also binds fixed cells (e.g., fixed with formalin). Similar to 37E1B5, 11E8 specifically binds αvβ8, and inhibits release of active, mature TGFβ peptide, without inhibiting adhesion of latent TGFβ to αvβ8. Because 11E8 can bind αvβ8 on both unfixed and formalin fixed cells, and can reduce release of mature TGFβ, 11E8 is useful for detection (e.g., diagnosis or monitoring), therapy, and combined detection/therapeutic applications.

The heavy and light chain variable regions (with CDRs underlined) for antibody 11E8 are set forth below:

```
SEQ ID NO: 10-Heavy chain variable region for
11E8 (CDRs 1-3 are underlined; SEQ ID NOs:
48-50, respectively)
EVQLQQSGPELMKTGASVKISCKATGYTFSSYWIEWVKQRPGHGLEWIGD

ILPGSGTTNYNEKFKGRATVTADRSSNTAYMQLSSLTYGDSAVYYCATWG

WDTYWDQGTSVTVSS

SEQ ID NO: 11-Light chain variable region for
11E8 (CDRs 1-3 are underlined; SEQ ID NOs:
51-53 respectively)
DIVMTQSPSSLSASLGDRVTISCSASQGISNYLNWYQQKPDGTVKLLIYY

TSSLHSGVPSRFSGSGSGTDYSLTISNLEPEDIATYYCQQYSNLPYTFGG

GTKLEIKR
```

Accordingly, antibodies are provided that that comprise heavy chain CDRs SEQ ID NOS:48, 49, and 50, and light chain CDRs SEQ ID NOS: 51, 52, and 53. In some embodiments, the antibodies comprise the heavy chain variable region SEQ ID NO:10 and/or the light chain variable region SEQ ID NO:11.

As shown in FIGS. 11A-B and 12A-B, an affinity matured antibodies of 11E8 have been discovered and designated 11E8Mut28, 11E8Mut94, and 11E839.

The 11E8Mut28 affinity matured antibody has a change in the heavy chain CDR3 (WGWDSY; SEQ ID NO: 54) and a change in the light chain CDR3 (QQFSNLPYT; SEQ ID NO: 55). Accordingly, in some embodiments, antibodies are provided that comprise:

heavy chain CDRs SEQ ID NOS:48, 49, and 54, and light chain CDRs SEQ ID NOs: 51, 52, and 53; or heavy chain CDRs SEQ ID NOs:48, 49, and 50, and light chain CDRs SEQ ID NOs: 51, 52, and 55; or heavy chain CDRs SEQ ID NOs:48, and 54, and light chain CDRs SEQ ID NOs: 51, 52, and 55.

11E8Mut28 also has changes in heavy chain FR3 (KAAITADTSSNTSYLQLSSLTSEDSAVYYCAR; SEQ ID NO: 56) and heavy chain FR4 (WGQGTLVTVSS; SEQ ID NO: 57). Thus, in some embodiments, the antibodies comprise a heavy chain variable region comprising SEQ ID NO: 56 or 57 (e.g., SEQ ID NO:32), and optionally a light chain variable region comprising SEQ ID NO:23.

The 11E8Mut94 affinity matured antibody has a change in the heavy chain CDR2 and CDR3 (DILPGSGTTNYNEKFEG, SEQ ID NO:90 and WGWDSY, SEQ ID NO:54, respectively). Accordingly, in some embodiments, antibodies are provided that comprise:

heavy chain CDRs SEQ ID NOS:48, 90, and 54, and light chain CDRs SEQ ID NOS: 51, 52, and 53.

11E8Mut94 also has changes in heavy chain FR2 (WVKQRPGHGFEWIG,SEQIDNO:91), heavy chain FR3 (RAAITADTSSNTSYMQLSSLTSEDSAVYYCAR, SEQ ID NO:92) and heavy chain FR4 (WGQGTLVTVSS; SEQ ID NO:57). Thus, in some embodiments, the antibodies comprise a heavy chain variable region comprising SEQ ID NO:91, 92, or 57 (e.g., SEQ ID NO:88), and optionally a light chain variable region comprising SEQ ID NO:89. 11E8Mut94 also has changes in light chain FR1 (DIKMTQTPSSLSASLGDRVTISC, SEQ ID NO:93). In some embodiments, the antibodies comprise a light chain variable region comprising SEQ ID NO:93, e.g., SEQ ID NO:89, and optionally a heavy chain of SEQ ID NO:88.

The 11E8Mut39 affinity matured antibody has a change in the heavy chain CDR1 (TYWIE; SEQ ID NO:112), heavy chain CDR2 (HTLPGSGTTNYNEKFKG; SEQ ID NO:113), light chain CDR1 (STSQDVSSYLN; SEQ ID NO:105) and light chain CDR2 (YASNLHS; SEQ ID NO:107). Accordingly, in some embodiments, antibodies are provided that comprise:

heavy chain CDR SEQ ID NOs:112, 113, and 50, and light chain CDR SEQ ID NOs: 51, 52, and 53;

heavy chain CDR SEQ ID NOs: 48, 49, and 50, and light chain CDR SEQ ID NOs:105, 107, and 53; or heavy chain CDR SEQ ID NOs:112, 113, 50, and light chain CDR SEQ ID NOs:105, 107, and 53.

11E8Mut39 also has changes in heavy chain FR1 (QVQLQQSGPELMKTGASVKISCKATGYTFS; SEQ ID NO:106) heavy chain FR3 (RATITADRPSNTSYMQLSSLTYGDSAVFYCAT; SEQ ID NO:114), and heavy chain FR4 (WDHGTSVTVSS; SEQ ID NO:108). 11E8Mut39 has changes in light chain FR1 (DIMMTQTPSSLSASLGDRVTISC; SEQ ID NO:115) and light chain FR4 (FGGGTKLEIKA; SEQ ID NO:111). Thus, in some embodiments, the antibodies comprise a heavy chain variable region comprising SEQ ID NO:106, 114, or 108 (e.g., SEQ ID NO:102), and optionally a light chain variable region comprising SEQ ID NO:104. In some embodiments, the antibodies have a light chain variable region comprising SEQ ID NO:115 or 111 (e.g., SEQ ID NO:104), and optionally a heavy chain variable region comprising SEQ ID NO:102.

C. 14E5

The 14E5 antibody binds a similar epitope on αvβ8 as 37E1B5. Like 37E1B5, 14E8 specifically binds αvβ8, but unlike 37E1B5, 14E5 does not inhibit release of active, mature TGFβ peptide, or adhesion of latent TGFβ to αvβ8.

Because 14E5 is specific for αvβ8, but does not block activity, it is useful for detection, e.g., in vivo diagnosis or monitoring applications.

The heavy and light chain variable regions (with CDRs underlined) for antibody 14E5 are set forth below:

```
SEQ ID NO: 12-Heavy chain variable region for
14E5 (CDRs 1-3 are underline; SEQ ID NOS:
58-60, respectively)
EVQLQQSGAELMKPGASVKISCKATGYTFSTYWIEWIKQRPGHGLEWIGH

ILPGSVITNYNEKFKGKAAITADTSSNTSYMQLSSLTSEDSAVYYCARWG

WDSYWGQGTLVTVSS

SEQ ID NO: 13-Light chain variable region for
14E5 (CDRs 1-3 are underlined; SEQ ID NOS:
61-63 respectively)
DIEMTQSPSSLSASLGDRVTISCSTSQDISSSLNWYQQKPDGTVTLLIYY

TSNLHSGVPSRFSGSGSGTDYSLTISNLEPEDIATYYCQQYSKLPYTFGG

GTKLEIKR
```

Accordingly, antibodies are provided that that comprise heavy chain CDRs SEQ ID NOS:58, 59, and 60, and light chain CDRs SEQ ID NOS:61, 62 and 63. In some embodiments, the antibodies comprise the heavy chain variable region SEQ ID NO:12 and/or the light chain variable region SEQ ID NO:13.

As shown in FIGS. 11A-B and 12A-B, seven affinity matured antibodies of 14E5 have been discovered, designated 14E5Mut11, 14E5Mut42, 14E5Mut54, 14E5Mut68, 14E5Mut65, 14E5Mut83 and 14E5Mut95. These affinity matured antibodies have changes in the CDR and FR sequences as set out below. In some embodiments, antibodies are provided that comprise CDRs and FRs from 14E5 and the affinity matured forms of 14E5 in various combinations.

14E5Mut11 has a change in the heavy chain CDR1 (TNWIE, SEQ ID NO:64), a change in the light chain CDR1 (SASQGISKYLN, SEQ ID NO:65), a change in the light chain CDR2 (YTSSLHS, SEQ ID NO:66), and a change in the light chain CDR3 (QQYSNLPYT, SEQ ID NO:67). Accordingly, in some embodiments, antibodies are provided that comprise combinations of the CDRs from 14E5 and 14E5Mut11, for example:

heavy chain CDRs SEQ ID NOS:64, 59, and 60, and light chain CDRs SEQ ID NOS: 61, 62, and 63; or heavy chain CDRs SEQ ID NOS:58, 59, and 60, and light chain CDRs SEQ ID NOS: 65, 66, and 67; or heavy chain CDRs SEQ ID NOS:64, 59, and 60, and light chain CDRs SEQ ID NOS:65, 66, and 67.

14E5Mut11 also has changes in the light chain FR1 and FR2 (DILMTQSPSSLSASLGDRVTISC, SEQ ID NO:68 and WYQQKPDGTVKLLTY, SEQ ID NO:69, respectively). Thus, in some embodiments, the antibodies comprise a light chain variable region comprising SEQ ID NO: 68 or 69 (e.g., SEQ ID NO:24), and optionally a heavy chain variable region comprising SEQ ID NO:33.

14E5Mut42 has a change in the light chain CDR1 (SASQGISNYLN, SEQ ID NO:70), a change in the light chain CDR2 (YTSSLHS, SEQ ID NO:66), and a change in the light chain CDR3 (QQYSDLPYT, SEQ ID NO:71). Accordingly, in some embodiments, antibodies are provided that comprise combinations of the CDRs from 14E5 and 14E5Mut42, for example:

heavy chain CDRs SEQ ID NOS:58, 59, and 60, and light chain CDRs SEQ ID NOS:70, 66, and 71.

14E5Mut42 also has changes in the heavy chain FR1 (EVPLQQSGAELMKPGASVKISCKATGYTFS, SEQ ID NO:72) light chain FR1 and FR2 (DIVMTQTPSSLSASLGDRVTISC, SEQ ID NO:73 and WYQQKPDGTVKLLTY, SEQ ID NO:69, respectively). Thus, in some embodiments, the antibodies comprise a heavy chain variable region comprising SEQ ID NO:72 (e.g., SEQ ID NO:34), optionally with a light chain comprising SEQ ID NO:25. In some embodiments, the antibodies comprise a light chain variable region comprising SEQ ID NO:73 or 69 (e.g., SEQ ID NO:25), and optionally a heavy chain variable region comprising SEQ ID NO:34.

14E5Mut54 has a change in the heavy chain CDR1 (TNWIE, SEQ ID NO:64), a change in the light chain CDR1 (SASQGISNYLN, SEQ ID NO:70), a change in the light chain CDR2 (YTSSLHS, SEQ ID NO:66), and a change in the light chain CDR3 (QQYSNLPYT, SEQ ID NO:67). Accordingly, in some embodiments, antibodies are provided that comprise combinations of the CDRs from 14E5 and 14E5Mut54, for example:

heavy chain CDRs SEQ ID NOS:64, 59, and 60, and light chain CDRs SEQ ID NOS: 61, 62, and 63; or
heavy chain CDRs SEQ ID NOS:58, 59, and 60, and light chain CDRs SEQ ID NOS:70, 66, and 67; or
heavy chain CDRs SEQ ID NOS:64, 59, and 60, and light chain CDRs SEQ ID NOS:70, 66, and 67.

14E5Mut54 also has changes in the heavy chain FR3 (KAAITADTSSNTSYMQLTSLTSEDSAVYYCAR, SEQ ID NO:74) and in light chain FR1 and FR2 (DILMTQTPSSLSASLGDRVTIRC, SEQ ID NO:75 and WYQQKPDGTVKLLTY, SEQ ID NO:69, respectively). Thus, in some embodiments, the antibodies comprise a heavy chain variable region comprising SEQ ID NO:74 (e.g., SEQ ID NO:35), optionally with a light chain comprising SEQ ID NO:26. In some embodiments, the antibodies comprise a light chain variable region comprising SEQ ID NO:75 or 69 (e.g., SEQ ID NO:26), and optionally a heavy chain variable region comprising SEQ ID NO:35.

14E5Mut68 has a change in the heavy chain CDR2 (DILPGSGTTNYNEKFKG, SEQ ID NO:76), a change in the light chain CDR1 (SASQGISNYLN, SEQ ID NO:70), a change in the light chain CDR2 (YTSSLHS, SEQ ID NO:66), and a change in the light chain CDR3 (QQYSELPYT, SEQ ID NO:77). Accordingly, in some embodiments, antibodies are provided that comprise combinations of the CDRs from 14E5 and 14E5Mut68, for example:

heavy chain CDRs SEQ ID NOS:58, 76, and 60, and light chain CDRs SEQ ID NOS: 61, 62, and 63; or
heavy chain CDRs SEQ ID NOS:58, 59, and 60, and light chain CDRs SEQ ID NOS:70, 66, and 77; or
heavy chain CDRs SEQ ID NOS:58, 76, and 60, and light chain CDRs SEQ ID NOS:70, 66, and 77.

14E5Mut68 also has changes in the heavy chain FR3 (RATVTADRSSNTSYMQLSSLTSEDSAVYYCAR, SEQ ID NO:78) and in light chain FR1 and FR2 (DIKMTQSPSSLSASLGDRVTISC, SEQ ID NO:79 and WYQQKPDGTVKLLTY, SEQ ID NO:69, respectively). Thus, in some embodiments, the antibodies comprise a heavy chain variable region comprising SEQ ID NO:78 (e.g., SEQ ID NO:36), optionally with a light chain comprising SEQ ID NO:27. In some embodiments, the antibodies comprise a light chain variable region comprising SEQ ID NO:79 or 69 (e.g., SEQ ID NO:27), and optionally a heavy chain variable region comprising SEQ ID NO:36.

14E5Mut65 has a change in the heavy chain CDR1 (TNWIE, SEQ ID NO:64), a change in the light chain CDR1 (SASQGISNYLN, SEQ ID NO:70), a change in the light chain CDR2 (YTSSLHS, SEQ ID NO:66), and a change in the light chain CDR3 (QQFSNLPYT, SEQ ID NO:80). Accordingly, in some embodiments, antibodies are provided that comprise combinations of the CDRs from 14E5 and 14E5Mut65, for example:

heavy chain CDRs SEQ ID NOS:64, 59, and 60, and light chain CDRs SEQ ID NOS: 61, 62, and 63; or
heavy chain CDRs SEQ ID NOS:58, 59, and 60, and light chain CDRs SEQ ID NOS:70, 66, and 80; or
heavy chain CDRs SEQ ID NOS:64, 59, and 60, and light chain CDRs SEQ ID NOS:70, 66, and 80.

14E5Mut65 also has changes in the heavy chain FR1 and FR3 (QVQLQQSGAELMKPGASVKISCKATGYSFS, SEQ ID NO:81 and KAAITADTSSNTSYMQLSSLTSDDSAVYYCAR, SEQ ID NO:82) and in light chain FR1 and FR2 (DIKMTQSPSSLSASLGDRVTISC, SEQ ID NO:79 and WYQQKPDGTVKLLTY, SEQ ID NO:69, respectively). Thus, in some embodiments, the antibodies comprise a heavy chain variable region comprising SEQ ID NO:81 or 82 (e.g., SEQ ID NO:37), optionally with a light chain comprising SEQ ID NO:28. In some embodiments, the antibodies comprise a light chain variable region comprising SEQ ID NO:79 or 69 (e.g., SEQ ID NO:28), and optionally a heavy chain variable region comprising SEQ ID NO:37.

14E5Mut83 has a change in the heavy chain CDR1 (THWIE, SEQ ID NO:83), a change in the light chain CDR1 (SASQGISNYLN, SEQ ID NO:70), a change in the light chain CDR2 (YTSSLHS, SEQ ID NO:66), and a change in the light chain CDR3 (QQYSDLPYT, SEQ ID NO:71). Accordingly, in some embodiments, antibodies are provided that comprise combinations of the CDRs from 14E5 and 14E5Mut83, for example:

heavy chain CDRs SEQ ID NOS:83, 59, and 60, and light chain CDRs SEQ ID NOS: 61, 62, and 63; or
heavy chain CDRs SEQ ID NOS:58, 59, and 60, and light chain CDRs SEQ ID NOS:70, 66, and 71; or
heavy chain CDRs SEQ ID NOS:83, 59, and 60, and light chain CDRs SEQ ID NOS:70, 66, and 71.

14E5Mut83 also has changes in the heavy chain FR1 (EVQLQQSGAVLMKPGASVKISCKATGYTFS, SEQ ID NO:84) and in light chain FR1 and FR2 (DILMTQSPSSLSASLGDRVTISC, SEQ ID NO:68 and WYQQKPDGTVKLLTY, SEQ ID NO:69, respectively). Thus, in some embodiments, the antibodies comprise a heavy chain variable region comprising SEQ ID NO:84 (e.g., SEQ ID NO:38), optionally with a light chain comprising SEQ ID NO:29. In some embodiments, the antibodies comprise a light chain variable region comprising SEQ ID NO:68 or 69 (e.g., SEQ ID NO:29), and optionally a heavy chain variable region comprising SEQ ID NO:38.

14E5Mut95 has a change in the light chain CDR1 (SASQGISNYLN, SEQ ID NO:70), a change in the light chain CDR2 (YTSSLHS, SEQ ID NO:66), and a change in the light chain CDR3 (QQYSDLPYT, SEQ ID NO:71). Accordingly, in some embodiments, antibodies are provided that comprise combinations of the CDRs from 14E5 and 14E5Mut95, for example:

heavy chain CDRs SEQ ID NOS:58, 59, and 60, and light chain CDRs SEQ ID NOS:70, 66, and 71.

14E5Mut95 also has changes in the heavy chain FR1 AND FR3 (EVQLQQTGAELMKPGASVKISCKATGYTFS, SEQ ID NO:85 and KAVITADTSSNTSYMQLSSLTSEDSAVYYCAR, SEQ ID NO:86) and in light chain FR1 and FR2 (DIEMTQSPSSLSASLGDRVTISC, SEQ ID NO:87 and WYQQKPDGTVKLLTY, SEQ ID NO:69, respectively). Thus, in some embodiments, the antibodies comprise a heavy chain variable region comprising SEQ ID NO:86 (e.g., SEQ ID NO:39), optionally with a light chain comprising SEQ ID NO:30. In some embodiments, the antibodies comprise a light chain variable region comprising SEQ ID NO:87 or 69 (e.g., SEQ ID NO:30), and optionally a heavy chain variable region comprising SEQ ID NO:29.

D. 6B9

The 6B9 antibody binds an epitope on β8 that is included in amino acids 61-105 of human β8 (amino acid positions relative to the full length β8 sequence shown in SEQ ID NO:17), and does not interact significantly with murine β8. As shown in the examples, serine 95 is involved in the epitope (either directly bound, or indirectly involved in epitope structure), as substitution of serine with proline at that position essentially eliminates binding. The 6B9 antibody does not compete for binding with 37E1B5, 11E8, or 14E5. In addition, the 6B9 antibody can detect β8 on unfixed and formalin fixed cells and tissues, and distinguish β8 expression levels, e.g., on cells that express different levels of β8 (see Examples, and FIGS. 6 and 8. Expression levels can also be indicative of genomic copy number of β8 in the cell and pathogenesis.

The heavy and light chain variable regions (with CDRs underlined) for antibody 6B9 are set forth below:

SEQ ID NO: 18-Heavy chain variable region for 6B9 (CDRs 1-3 are underlined, SEQ ID NOS: 40-42, respectively)
QVQLQQSGAELVRPGTSVKVSCKASGYAFT<u>DYLIE</u>WVKQRPGQGLEWIG<u>V INPETGGTNYNAKFK</u>GKATLTADKSSSAYMQLSSLTSGDSAVYFCAR<u>EA GNYIYAMDY</u>WGQGTSVTVSS SEQ ID NO: 19-Light chain variable region for 6B9 (CDRs 1-3 are underlined, SEQ ID NOS: 43-45, respectively)
DIQMTQSPASLSASVGETVTITC<u>RASVNIYSYLV</u>WYQQKQGKSPQLLVH<u>N AKTLAEG</u>VPSRFSGSGSGTQFSLKINSLQPEDFGSYYC<u>QHHHGTPYT</u>FGG

GTKLEIKR

Accordingly, antibodies are provided that that comprise heavy chain CDRs SEQ ID NOs:40, 41, and 42, and light chain CDRs SEQ ID NOs: 43, 44, and 45. In some embodiments, the antibodies comprise the heavy chain variable region SEQ ID NO:18 and/or the light chain variable region SEQ ID NO:19.

As shown in FIGS. 11A-B and 12-A-B, an affinity matured antibody of 6B9, designated 6B9Mut1, has been discovered. Notably this affinity matured antibody has a change in the heavy chain CDR2 (VINPETGGTNYNAKF RG; SEQ ID NO: 46). Accordingly, in some embodiments, antibodies are provided that comprise heavy chain CDRs SEQ ID NOS:40, 46, and 42, and light chain CDRs SEQ ID NOS: 43, 44, and 45.

6B9Mut1 also has a change in the light chain FR1 (DI VMTQSPASLSASVGETVTITC; SEQ ID NO:47). In some embodiments, the antibodies comprise a light chain variable region comprising SEQ ID NO:47 (e.g., the variable region could comprise SEQ ID NO:23) and optionally a heavy chain variable region comprising SEQ ID NO:18.

E. 4F1

The 4F1 antibody also binds an epitope on β8 that is included in amino acids 61-105 of β8 (amino acid positions relative to the full length β8 sequence shown in SEQ ID NO:17), and does not interact significantly with murine β8. As shown in the examples, serine 95 is involved in the epitope, as substitution of serine with proline at that position essentially eliminates binding. The 4F1 antibody does not compete for binding with 37E1B5, 11E8, or 14E5. In addition, the 4F1 antibody can detect β8 on unfixed and formalin fixed cells and tissues, and distinguish β8 expression levels, e.g., on cells that express different levels of β8 (Examples and FIGS. 6, 7, 9, and 10). Expression levels can also be indicative of genomic copy number of β8 in the cell and pathogenesis.

The heavy and light chain variable regions (with CDRs underlined) for antibody 4F1 are set forth below:

SEQ ID NO: 20-Heavy chain variable region for 4F1 (CDRs 1-3 are underlined, SEQ ID NOS: 116-118, respectively)
QVQLQQSGAELVRPGTSVKVSCKASGYAFT<u>NYLIE</u>WVKQRPGQGLEWIG<u>V INPGTGGTNYNKKFK</u>VKATLTADKSSSTAYMQLGGLTFDDSAVYFCAR<u>E GNARTYYYAMDY</u>WGQGTSVTVSS SEQ ID NO: 21-Light chain variable region for 4F1 (CDRs 1-3 are underlined, SEQ ID NOS: 119-121, respectively)
DIEMTQTPASLSASVGETVTITC<u>RASENIYSYLV</u>WYQQKQGKSPQVLVY<u>N AKTLAEG</u>VPSRFSGSGSGTQFSLKINSLQPEDFGSYYC<u>QHHNGTPYT</u>FGG

GTKLEIKR

Accordingly, antibodies are provided that that comprise heavy chain CDRs SEQ ID NOs:116, 117, and 118, and light chain CDRs SEQ ID NOs:119, 120, and 121. In some embodiments, the antibodies comprise the heavy chain variable region SEQ ID NO:20 and/or the light chain variable region SEQ ID NO:21.

F. Anti-αvβ8 Antibodies

Provided herein are antibodies that specifically bind to integrin αvβ8, but do not significantly bind to other integrins (e.g., αvβ6, αβ3, etc.). The present antibodies bind to a specific epitope or epitope region within αvβ8. The epitope can be a conformational (non-linear) or nonconformational epitope. Such an antibody can bind to β8 alone, i.e., the epitope is located within β8, or to a non-linear epitope that comprises parts of both subunits, or an epitope that relies on the interaction of αβ and β8. The present antibodies include the αvβ8 specific antibodies described above, as well as humanized, chimeric, and/or labeled versions thereof, and αvβ8 binding fragments and/or variants thereof.

In some embodiments, the antibody binds to β8 and inhibits TGFβ activation, e.g., compared to TGFβ activation in the absence of the antibody. In some embodiments, the antibody does not reduce adhesion of cells expressing αvβ8 to TGFβ, that is, the antibody does not reduce αvβ8-mediated cell adhesion to TGFβ. In some embodiments, the antibody can reduce binding of soluble αvβ8 to TGFβ, compared to αvβ8 binding in the absence of the antibody. In some embodiments, the antibody can bind to an epitope on β8 that is within SEQ ID NO:11. In some embodiments, the epitope includes at least one amino acid selected from amino acids R79, I85, S95, P100, I108, P109, R128, H140, and F179 of human β8. In some embodiments, the epitope includes at least one amino acid selected from amino acids I74, N88, I107, T110, I125, R175, and F180 of human β8. In some embodiments, the epitope includes at least one amino acid selected from amino acids I125, R128, R175, F179, and F180 of human β8. In some embodiments, the antibody binds human, but not mouse β8.

The binding site, i.e., epitope, of an antibody raised against a given antigen can be determined using methods known in the art. For example, a competition assay (e.g., a competitive ELISA) can be carried out using an antibody with a known epitope. If the test antibody competes for antigen binding, then it likely shares at least part of the same epitope. The epitope can also be localized using domain swapping or selective mutagenesis of the antigen. That is, each region, or each amino acid, of the antigen can be "swapped" out, or substituted with amino acids or components that are known to not interact with the test antibody. If substitution of a given region or amino acid reduces binding of the test antibody to the substituted antigen compared to the non-substituted antigen, then that region or amino acid is likely involved in the epitope.

In some embodiments, the antibody is a humanized 37E1B5 antibody with a heavy chain variable region comprising SEQ ID NO:8, and a light chain variable region comprising SEQ ID NO:9. The isotype of the antibody can be IgG1, IgG2, IgG2a, IgG3 or IgG4.

The presently described antibodies can be polyclonal or monoclonal. Polyclonal sera typically contain mixed populations of antibodies specifically binding to several epitopes along the length of αvβ8. However, polyclonal sera can be specific to a particular segment of αvβ8. In some embodiments, the antibody is chimeric, humanized (see Queen et al., *Proc. Natl. Acad. Sci. USA* 86:10029-10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539), or human (Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (1991) EP1481008, Bleck, Bioprocessing Journal 1 (September/October 2005), US2004132066, US2005008625, WO2004072266, WO2005065348, WO2005069970, and WO2006055778. In some embodiments, the antibodies are humanized or chimeric forms of 37E1B5, 11E8, of 14E5. Human isotype IgG1, IgG2, IgG3 or IgG4 can be used for humanized or chimeric antibodies. Some antibodies specifically bind to αvβ8 with a binding affinity greater than or equal to about $10^7$, $10^8$, $10^9$, $10^{10}$, $10^{11}$, or $10^{12}$ M$^{-1}$ (e.g., with a Kd in the micromolar ($10^{-6}$), nanomolar ($10^{-9}$), picomolar ($10^{-12}$), or lower range).

G. Detection of TGF Activity and Effect of Anti-αvβ8 Antibodies

To determine the effect of a antibody on TGFβ activity, a number of TGFβ bioassays are available. For example, TGFβ activation can be tested in a coculture assay. Test cells expressing αvβ8 are co-cultured with TMLC cells, i.e., mink lung epithelial cells stably transfected with a TGF-β responsive promoter fragment driving the luciferase gene (Abe et al. (1994) *Annal Biochem* 216:276). TMLC cells are highly responsive to TGFβ with a very low background of TGFβ activation. TMLC cells can thus be used in coculture with other cell lines or cell-free fractions to test for the presence of active TGFβ using luminescence as a readout. Assays can be performed in the presence or absence of anti TGFβ-blocking antibody (10 µg/ml, 1D11; R&D Systems), anti-β8 (20 µg/ml, 37E1B5) or anti-β6 (150 µg/ml, 10D5) as described (Abe (1994); Munger (1999)).

To measure active TGFβ in tumor tissue, equal weights of tumor tissue can be minced and incubated in sterile DME for 30 min at 4° C. The supernatants containing active TGFβ can be harvested after centrifugation (20 g) at 4° C. The pellets can then be incubated in serum-free DME for 20 min at 80° C. to activate SLC, after which the supernatants can be harvested. The supernatants containing active or heat-activated (latent) TGFβ are then added to pre-plated TMLC cells with or without 1D11. For protease inhibitor assays, inhibitors are added at the initiation of the coculture. The maximal dose of each inhibitor are defined as the highest concentration that do not inhibit the ability of the TMLC cells to respond to recombinant active TGFβ. To measure soluble TGFβ activity from cultured cells, cells are incubated in 100 µl of complete medium with or without 37E1 or 10D5 for 1 h at 37° C. with gentle rotation. Cell-free supernatants are harvested by centrifugation (20 g) for 5 min at 4° C. and then added to preplated TMLC cells in the presence or absence of 1D11. For soluble receptor assays, conditioned medium obtained from overnight cultures of cells are used. Relative luciferase units are defined as activity minus the background activity of the TMLC reporter cells.

IV. Methods of Generating Antibodies

For preparation and use of suitable antibodies as described herein, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, Antibodies, *A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody as described herein can also be produced in various formats, including as a Fab, a Fab', a F(ab')$_2$, a scFv, or a dAB. The antibody fragments can be obtained by a variety of methods, including, digestion of an intact antibody with an enzyme, such as pepsin (to generate (Fab')$_2$ fragments) or papain (to generate Fab fragments); or de novo synthesis. Antibody fragments can also be synthesized using recombinant DNA methodology. In some embodiments, an anti-β8 antibody comprises F(ab')$_2$ fragments that specifically bind β8. An antibody of the invention can also include a human constant region. See, e.g., Fundamental Immunology (Paul ed., 4d ed. 1999); Bird, et al., *Science* 242:423 (1988); and Huston, et al., *Proc. Natl. Acad. Sci. USA* 85:5879 (1988).

Methods for humanizing or primatizing non-human antibodies are also known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20:227, 2007). The antibody or antibody fragment can also be labeled, or conjugated to a therapeutic agent as described below.

The specificity of antibody binding can be defined in terms of the comparative dissociation constants (Kd) of the antibody for the target (e.g., β8) as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target.

The desired affinity for an antibody, e.g., high (pM to low nM), medium (low nM to 100 nM), or low (about 100 nM or higher), may differ depending upon whether it is being used as a diagnostic or therapeutic. For example, an antibody with medium affinity may be more successful in localizing to desired tissue as compared to one with a high affinity. Thus, antibodies having different affinities can be used for diagnostic and therapeutic applications.

A targeting moiety will typically bind with a Kd of less than about 1000 nM, e.g., less than 250, 100, 50, 20 or lower nM. In some embodiments, the Kd of the affinity agent is less than 15, 10, 5, or 1 nM. In some embodiments, the Kd is 1-100 nM, 0.1-50 nM, 0.1-10 nM, or 1-20 nM. The value of the dissociation constant (Kd) can be determined by well-known methods, and can be computed even for complex mixtures by methods as disclosed, e.g., in Caceci et al., *Byte* (1984) 9:340-362.

Affinity of an antibody, or any targeting agent, for a target can be determined according to methods known in the art, e.g., as reviewed in Ernst et al. Determination of Equilibrium Dissociation Constants, *Therapeutic Monoclonal Antibodies* (Wiley & Sons ed. 2009).

Quantitative ELISA, and similar array-based affinity methods can be used. ELISA (Enzyme linked immunosorbent signaling assay) is an antibody-based method. In some cases, an antibody specific for target of interest is affixed to a substrate, and contacted with a sample suspected of containing the target. The surface is then washed to remove unbound substances. Target binding can be detected in a variety of ways, e.g., using a second step with a labeled antibody, direct labeling of the target, or labeling of the primary antibody with a label that is detectable upon antigen binding. In some cases, the antigen is affixed to the substrate (e.g., using a substrate with high affinity for proteins, or a Strepavidin-biotin interaction) and detected using a labeled antibody (or other targeting moiety). Several permutations of the original ELISA methods have been developed and are known in the art (see Lequin (2005) *Clin. Chem.* 51:2415-18 for a review).

The Kd, Kon, and Koff can also be determined using surface plasmon resonance (SPR), e.g., as measured by using a Biacore T100 system. SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given frequency is shined on the surface, the changes to the optical reflectivity of the gold indicate binding, and the kinetics of binding.

Binding affinity can also be determined by anchoring a biotinylated interactant to a streptaviden (SA) sensor chip. The other interactant is then contacted with the chip and detected, e.g., as described in Abdessamad et al. (2002) *Nuc. Acids Res.* 30:e45.

V. Pharmaceutical Applications and Compositions

The anti-αvβ8 antibodies described herein (including αvβ8 binding fragments thereof, labeled antibodies, immunoconjugates, pharmaceutical compositions, etc.) can be used to detect, treat, ameliorate, or prevent chronic obstructive pulmonary disease (COPD) and asthma.

The anti-αvβ8 antibodies described herein (including αvβ8 binding fragments thereof, labeled antibodies, immunoconjugates, pharmaceutical compositions, etc.) can be used to detect, treat, ameliorate, or prevent inflammatory bowel disease.

The anti-αvβ8 antibodies described herein (including αvβ8 binding fragments thereof, labeled antibodies, immunoconjugates, pharmaceutical compositions, etc.) can be used to detect, treat, ameliorate, or prevent an inflammatory brain autoimmune disease, multiple sclerosis, a demylinating disease (e.g., transverse myelitis, Devic's disease, Guillain-Barré syndrome), neuroinflammation, kidney disease, or glioma.

The anti-αvβ8 antibodies described herein (including αvβ8 binding fragments thereof, labeled antibodies, immunoconjugates, pharmaceutical compositions, etc.) can be used to detect, treat, ameliorate, or prevent arthritis.

The anti-αvβ8 antibodies described herein (including αvβ8 binding fragments thereof, labeled antibodies, immunoconjugates, pharmaceutical compositions, etc.) can be used to detect, treat, ameliorate, or prevent various fibrotic disorders, such as airway fibrosis, idiopathic pulmonary fibrosis, non-specific interstitial pneumonia, post-infectious lung fibrosis, diffuse alveolar damage, collagen-vascular disease associated lung fibrosis, drug-induced lung fibrosis, silicosis, asbestos-related lung fibrosis, respiratory bronchiolitis, respiratory bronchiolitis interstitial lung disease, desquamative interstitial fibrosis, cryptogenic organizing pneumonia, chronic hypersensitivity pneumonia, drug-related lung or hepatic fibrosis, renal fibrosis, and liver fibrosis (e.g., induced by alcohol, drug use, steatohepatitis, viral infection (e.g., hepatitis B or C), choleostasis, etc.).

The anti-αvβ8 antibodies described herein (including αvβ8 binding fragments thereof, labeled antibodies, immunoconjugates, pharmaceutical compositions, etc.) can be used to detect, treat, ameliorate, or prevent adenocarcinoma, squamous carcinoma, breast carcinoma, and cancer growth and metastasis.

One of skill will appreciate that the nature of the pharmaceutical composition and route of administration will depend in part on the condition being treated.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

A pharmaceutical composition comprising an antibody described herein (or αvβ8 binding fragment thereof) can be administered, alone or in combination with other suitable components, can be made into aerosol formulations ("nebulized") to be administered via inhalation. Aerosol formulations can be placed into pressurized acceptable propellants, such as dichlorodifluoromethane, propane, nitrogen, etc.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Antibodies are typically administered by parenteral or intravenous administration. The formulations of compounds can be presented in unit-dose or multi-dose sealed containers, such as ampules and vials.

Injection solutions and suspensions can be prepared from sterile powders, granules, and tablets of the kind previously described. Methods for preparing parenterally administrable compositions will be known or apparent to those skilled in the art and are described in more detail in such publications as Remington's Pharmaceutical Science, 15th ed., Mack Publishing Company, Easton, Pa. (1980).

The compositions for administration typically comprises an antibody as described herein (e.g., an anti-αvβ8 antibody or αvβ8 binding fragment or immunoconjugate thereof) dissolved in a pharmaceutically acceptable carrier, e.g., an aqueous carrier. A variety of aqueous carriers can be used, e.g., buffered saline. These solutions are sterile and generally free of undesirable matter. These compositions may be sterilized by conventional, well known sterilization techniques. The compositions can contain pharmaceutically acceptable auxiliary substances as required to approximate physiological conditions such as pH adjusting and buffering agents, for example, sodium acetate, sodium chloride, potassium chloride, calcium chloride, sodium lactate, etc. The concentration of active agent in these formulations can vary widely, and will be selected primarily based on fluid volumes, viscosities, body weight and the like in accordance with the particular mode of administration selected and the patient's needs.

The formulation may also provide additional active compounds, including, chemotherapeutic agents, cytotoxic agents, cytokines, growth inhibitory agent, and anti-hormonal agent. The active ingredients can be prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunocongugates can also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

VI. Diagnostic Compositions and Applications

Integrin avb8 is expressed on fibroblasts, stellate cells, chondrocytes, activated macrophages and subsets of T and B-cells. Integrin avb8 is increased in expression in fibroblasts in COPD and pulmonary fibrosis, and can be used as a surrogate marker for increased fibroblast cell mass. Thus the presently disclosed antibodies can be broadly applicable to bioimaging strategies to detect fibroinflammatory processes. The presently described therapeutic and diagnostic antibodies can be applied to: inflammatory bowel disease (IBD), chronic obstructive pulmonary disease (COPD), asthma, arthritis, a hepatic fibroinflammatory disorder, alcohol induced liver injury, non-alcoholic steatohepatitis (NASH), viral hepatitis, and primary biliary cirrhosis (PBC), graft rejection after liver transplantation, autoimmune hepatitis, an autoimmune disorder, lupus erythematosus, scleroderma, dermatomyositis, bullous pemphigoid, pemphigus vulgaris, a pulmonary fibrotic disorder, an inflammatory brain autoimmune disease, multiple sclerosis, a demyelinating disease, neuroinflammation, kidney disease, glomerulonephritis, hepatocellular carcinoma (HCC), adenocarcinoma, squamous carcinoma, glioma, melanoma, prostate, ovarian, uterine and breast carcinoma.

As explained above, anti-αvβ8 antibodies described herein (including αvβ8 binding fragments thereof, affinity matured variants, and antibody variants less than 50 or 25 kD or scFvs) can be used for diagnosis, either in vivo or in vitro (e.g., using a biological sample obtained from an individual). The antibody is typically conjugated or otherwise associated with a detectable label. The association can be direct e.g., a covalent bond, or indirect, e.g., using a secondary binding agent, chelator, or linker.

A labeled antibody can be provided to an individual to determine the applicability of an intended therapy. For example, a labeled antibody may be used to detect the integrin β8 density within a diseased area. For therapies intended to target TGFβ or αvβ8 activity (to reduce TGFβ or αvβ8 activity), the density of β8 is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MRI, PET scanning, etc.). Such in vivo methods can be carried out using any of the presently disclosed antibodies. In some embodiments, labeled 14E5 is used, as it does not affect TGFβ levels.

Any of the presently disclosed antibodies can also be used for in vitro diagnostic or monitoring methods, e.g., using cells or tissue from a patient sample. In some embodiments, labeled 11E8 (or a β8 binding fragment or affinity-matured variant) is used, as it can bind fixed cells as well as non-fixed cells. In some embodiments, labeled 6B9 (or a β8 binding fragment or affinity-matured variant) is used, as it can bind fixed cells as well as non-fixed cells, and it does not compete for β8 binding with therapeutic antibodies such as 11E8, 37E1, or 37E1B5. In some embodiments, labeled 4F1 (or aβ8 binding fragment or affinity-matured variant) is used, as it can bind fixed cells as well as non-fixed cells, and it does not compete for β8 binding with therapeutic antibodies such as 11E8, 37E1, or 37E1B5.

In some embodiments, the diagnostic antibody is a single-chain variable fragment (scFv). Intact antibodies (e.g., IgG) can be used for radioimmunotherapy or targeted delivery of therapeutic agents because they exhibit high uptake and retention. In some cases, the persistence in circulation of intact mAbs can result in high background (Olafsen et al. (2012) Tumour Biol. 33:669-77; Cai et al. (2007) J Nucl Med. 48:304-10). ScFvs, typically with a molecular mass of ~25 kD, are rapidly excreted by the kidneys, but are monovalent and can have lower affinity. The issues of monovalency can be overcome with advanced antibody engineering (as shown herein), where affinities can be improved to the low nM to pM range. Such antibodies have short enough half-lives to be useful as imaging agents and have suitable binding characteristics for tissue targeting (Cortez-Retamozo et al. (2004) Cancer Res. 64:2853-7). As shown herein, we have created a number of very high affinity scFV antibody derivatives of 4F1, 6B9 and 14E5 that can be converted to humanized scFV platforms. These improved antibodies are not function blocking, and thus can be used in combination with a therapeutic agent that targets β8.

A diagnostic agent comprising an antibody described herein can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). The terms "detectable agent," "detectable moiety," "label," "imaging agent," and like terms are used synonymously herein. A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. PET is particularly sensitive and quantitative, and thus valuable for characterizing fibrotic processes in vivo (Olafsen et al. (2012) *Tumour Biol.* 33:669-77; Cai et al. (2007) *J Nucl Med.* 48:304-10). This is useful beyond a companion diagnostic and would be generally useful to diagnose, clinically stage and follow fibrotic patients during any treatment regimen.

A radioisotope can be incorporated into the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes* 2nd Ed.: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, a diagnostic agent can include chelators that bind, e.g., to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl] benzoic acid (CPTA), Cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra(methylene phosphonic acid) (DOTP), 1,4,8,11-tetraazacyclotetradecane-1,4,8,11-tetraacetic acid (TETA), 1,4,7,10-tetraazacyclododecane-1,4,7,10-tetraacetic acid (DOTA), $N^1,N^1$-bis(pyridin-2-ylmethyl)ethane-1,2-diamine (ENPy2) and derivatives thereof.

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives.

VII. Methods of Treatment

The presently described anti-αvβ8 antibodies, and αvβ8-binding fragments or immunoconjugates thereof can be administered to an individual using known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical (e.g., transdermal), or inhalation routes. Administration can be local or systemic.

The compositions can be administered for therapeutic or prophylactic treatments. In therapeutic applications, compositions are administered to a patient suffering from a disease (e.g., IBD, cancer, fibrosis (pulmonary or hepatic), COPD, asthma, arthritis, etc.) in a "therapeutically effective dose." Amounts effective for this use will depend upon the disorder to be treated, the route of administration, the severity of the condition, and the general state of the patient's health. Single or multiple administrations of the compositions may be administered depending on the dosage and frequency as required and tolerated by the patient. The presently described compositions can be administered to humans and other animals, particularly mammals. Thus the methods are applicable to both human therapy and veterinary applications. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, etc. The presently described compositions can also be combined with radiotherapy or immunotherapy as well as currently developing therapeutics.

Combination therapies contemplate coadministration, using separate formulations or a single pharmaceutical formulation, and consecutive administration in either order.

To determine a therapeutically effective dose, a low dose of an anti-αvβ8 antibody (or αvβ8 binding fragment or immunoconjugate thereof) can be initially administered to the individual, and the dose can be incrementally increased until the condition of the individual begins to improve. For example, the initial dosage can be about 0.001 mg/kg to about 1 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used at later time points if the condition of the individual does not change at the lowest dose. As noted above, one of skill will appreciate that a number of variables must be considered when determining a therapeutically effective dose. The dose administered to a patient should be sufficient to effect a beneficial therapeutic response in the patient over time. The size of the dose also will be determined by the existence, nature, and extent of any adverse side-effects that accompany the administration of a particular composition (or combination therapy) in a particular patient.

VIII. Examples

A. Example 1

37E1B5 Antibody

The heavy and light chain V region sequences of 37E1, 37E1B5, and humanized 37E1B5 (h37E1B5 or Hu37E1B5) are shown in FIG. 1. The framework and CDR regions are indicated. The humanized 37E1B5 antibody retains the high affinity and activity of 37E1B5.

In in vitro culture, 37E1 at a concentration of about 200 µg/ml inhibits release of active, mature TGFβ peptide. As explained above, 37E1B5 has a much higher affinity, and is active in the picomolar range. 37E1B5 at 10 µg/m is very effective for inhibiting release of active, mature TGFβ peptide in in vitro culture.

B. Example 2

Generation of the 11E8 and 14E5 Antibodies

The 11E8 and 14E5 antibodies were produced in hybridoma cells, which were created by fusing SP2/0 myeloma cells with lymphocytes from specifically immunized mice. The mice were immunized by subcutaneous injection of an engineered version of secreted, purified integrin αvβ8.

C. Example 3

Characterization of the β8 Epitope

Chimeric integrin β8 constructs, which swapped mouse sequences into human ITGB8 were used to localize the binding epitopes for the 37E1B5, 11E8, and 14E5 antibodies. The epitope was localized by antibody binding, cell surface staining, and detection by flow cytometry. The epitope is encompassed within amino acids 121-180 of human integrin β8 (relative to the β8 sequence shown in SEQ ID NO:17). All three antibodies bind to human β8, but not to mouse β8. Therefore, at least one of the 9 non-conservative amino acid differences or 7 minor amino acid differences (indicated by + in the middle line of the sequence) are included in the binding epitope, or affect the 3-dimensional structure of the domain in such a way as to distinguish the mouse from the human protein. The epitope falls in what is known as the Psi hybrid and the alpha1 helix and alpha1 linker region of the Beta-I domain of the integrin β8 subunit, and is found on the surface of the molecule.

To better define the epitope of 11E8, a competition assay was performed with 37E1B5. Addition of unlabeled 37E1B5 inhibited binding of labeled 11E8 antibody binding to ITGB8 (human integrin β8) transfected SW480 cells and αvβ8-expressing puro cells. The result indicates that the epitopes of these antibodies significantly overlap.

The variable region sequences for 11E8 were obtained, as shown in SEQ ID NOs:10 and 11. CDRs 1-3 of the 11E8 heavy chain are: SYWIE (SEQ ID NO:48), DILPGS-GTTNYNEKFKG (SEQ ID NO:49), and WGWDTY (SEQ ID NO:50), respectively. CDRs 1-3 of the 11E8 light chain are: SASQGISNYLN (SEQ ID NO:51), YTSSLHS (SEQ ID NO:52), QQYSNLPYT (SEQ ID NO:53), respectively.

```
                                                                    (SEQ ID NO: 2)
M   itgb8   121 GEVSVQLHPGAEANFMLKVRPLKKYPVDLYYLVDVSASMHNNIEKLNSVGNDLSKKMALY   180

(SEQ ID NO: 3)
                GEVS+QL PGAEANFMLKV PLKKYPVDLYYLVDVSASMHNNIEKLNSVGNDLS+KMA +

(SEQ ID NO: 1)
H   ITGB8   121 GEVSIQLRPGAEANFMLKVHPLKKYPVDLYYLVDVSASMHNNIEKLNSVGNDLSRKMAFF   180
```

SEQ ID NO:1 represents the region of human integrin β8 that includes the 37E1B5 epitope (amino acids 121-180). SEQ ID NO:2 represents the homologous murine sequence, which is not bound by the 37E1B5 antibody. The R at position 140 of the murine sequence is polymorphic, and can also be an H. The alignment sequence is represented by SEQ ID NO:3.

Further domain swapping studies within this region, substituting murine sequence for human, were performed to determine which amino acid(s) are included in the 37E1B5 epitope. Substituting murine amino acids 125-180 of Integrin β8 significantly reduced 37E1B5 binding. Thus, the epitope on human Integrin β8 includes at least one amino acid selected from I125, R128, R175, F179, and F180.

D. Example 4

Characterization of the 11E8 Antibody

The 11E8 antibody immunoprecipitates secreted αvβ8, and recognizes an epitope of the β8 subunit that is present on β8 transfected human 293 embryonic kidney cells and SW480 colon carcinoma cells, but not mock-transfected cells.

11E8 specifically blocks αvβ8-mediated TGF-β activation in ITGB8 transfected SW480 cells. Like 37E1B5, 11E8 is a high affinity antibody, and has the TGFβ blocking activity at a very low concentration (40 µg/ml in vitro was the lowest concentration tested). 11E8 does not block TGF-β activation mediated by other, non-β8 mediated mechanisms.

In addition, 11E8 recognizes a β8 epitope that is present on formalin fixed cells, making it well suited for localization studies in human tissues. The 11E8 antibody is active in vitro and in vivo, and can be used as a therapeutic agent to reduce αvβ8-mediated TGFβ activity. The ability of 11E8 to bind to fixed cells is helpful for accelerating regulatory approval, and for selecting a patient group (e.g., to confirm αvβ8 expression in the tissue of interest before initiating treatment), characterizing patient populations (e.g., according to localization of αvβ8 expression, response to various therapeutic agents, etc.), and monitoring disease progression (e.g., during a course of treatment with 11E8 antibody or another therapeutic agent).

E. Example 5

Characterization of the 14E5 Antibody

As disclosed above, the 14E5 antibody recognizes human but not mouse integrin β8, and binds an epitope within amino acids 120-180. The 14E5 antibody binds αvβ8 on αvβ8-expressing cells both in vitro and in vivo, but does not inhibit release of mature, active TGFβ. The 14E5 antibody is useful for diagnostic applications or patient population selection, as it binds with high affinity and works well in FACS assays.

To better define the epitope of the 14E5 antibody, a competition assay was performed with 37E1B5. Addition of unlabeled 37E1B5 antibody inhibited binding of labeled 14E5 antibody binding to ITGB8 transfected SW480 cells and αvβ8-expressing puro cells. The result indicates that the epitope for these antibodies is overlapping.

The variable region sequences for 14E5 were obtained, as shown in SEQ ID NOs:12 and 13. CDRs 1-3 of the 14E5 heavy chain are: TYWIE (SEQ ID NO:58), HILPGSVIT-NYNEKFKG (SEQ ID NO:59), WGWDSY (SEQ ID NO:60), respectively. CDRs 1-3 of the 14E5 light chain are: STSQDISSSLN (SEQ ID NO:61), YTSNLHS (SEQ ID NO:62), QQYSKLPYT (SEQ ID NO:63), respectively.

F. Example 6

The Role of Integrin αvβ8 in Airway Remodeling

TGF-β is involved in the inflammatory and fibrotic response. IL-1β upregulates expression of β8, which is overexpressed in the airways of COPD patients. A mouse model of β8-mediated airway remodeling was designed to determine the interactions of β8, TGF-β, and IL-1β in vivo. The results show that the IL-1-β induced, β8-mediated activation of TGF-β plays a critical role in airway remodeling.

β8 was deleted in C57BL/6 mice using a Cre/LoxP system. Intratracheal adenoviral IL-1β was used as a model for inflammation in 6- to 9-week old mice with one floxed integrin β8 allele and one knockout allele (Floxed/−). Either adenoviral human IL-1β (Ad-hIL-1β) or control adenovirus was administered intratracheally, with or without Ad-Cre.

Mice expressing the Cre-ER(T) fusion recombinase under control of the Collagen Iα2 promoter were used to show that fibroblasts play a major role in αvβ8-mediated activation of TGF-β in bleomycin induced lung fibrosis, ovalbumin induced airway remodeling, and Ad-IL1β-induced airway remodeling. Airway morphology changes were evaluated by histology. Gene expression of several inflammatory cytokines at multiple time points after Ad-hIL-1β administration revealed sequential induction of genes that characterize an inflammatory response.

Results from the β8 conditional knockout mice showed that β8 is required for IL-1β induced transient airway inflammation and fibrosis. Administration of human IL-1β in mice expressing β8 resulted in β8-mediated activation of TGF-β, induction of the mouse ccl2 and ccl20 genes (CC Chemokine Ligand 2 and 20, which are involved in inflammatory responses), recruitment of dendritic cells, and initiation and perpetuation of the adaptive immune response.

Data from the conditional integrin β8 knockouts showed decreased inflammation and fibrotic response to both Ad-hIL-1β and ovalbumin, which resulted in protection from airway remodeling. Thus, targeting β8 reduces IL-1β induced and ovalbumin-induced TGF-β activation in airway remodeling, and bleomycin-induced acute lung injury.

G. Example 7

Anti-Integrin β8 Reduces CoII Expression

Increased ECM production and increased fibroblast contractility are hallmarks of fibrotic responses seen in airway wall thickening, and increased type I collagen (CoII) and Smooth Muscle Actin (α-SMA). Neutralizing anti-β8 was used to assess the contribution of autocrine αvβ8-mediated TGF-β activation to the profibrotic response. Treatment of airway fibroblasts with β8 blocking antibodies inhibited α-SMA expression and CoII secretion, indicating that αvβ8-mediated activation of TGF-β influences the myofibroblast phenotype. Coculture of airway fibroblasts with squamous metaplastic human bronchial epithelial cells led to an increase in CoII protein expression by airway fibroblasts, which was IL-1β- and fibroblast β8-dependent. The increase in CoII expression could be almost completely inhibited by transfection of airway fibroblasts with β8 siRNA, indicating that inhibition of β8 mediated activation of TGFβ can reduce profibrotic responses and ameliorate fibrotic conditions.

H. Example 8

Integrin β8 Expression in COPD Fibroblasts

Integrin β8 expression was detected in fibroblasts from the lungs of human COPD patients using tissue staining and primary culture, and was higher than in non-COPD tissue. Integrin β8 expression was also significantly increased in fibroblasts isolated from patients with idiopathic pulmonary fibrosis, compared to fibroblasts from normal patients. COPD fibroblasts also have increased IL-1β-dependent integrin αvβ8 protein expression, compared to normal lung fibroblasts. These data demonstrate that αvβ8 is both a downstream target and pathologic mediator of IL-1β activity.

The anti-β8 antibodies described herein (e.g., 37E1B5, 14E5, and 11E8) can be used therapeutically and/or diagnostically in diseases where Integrin β8 is expressed, and IL-1β and/or TGF-β play a pathologic role.

I. Example 9

Integrin β8 Neutralizing Antibody Reduces Induced Airway Inflammation

The human BAC clone RP11-431K20 was used to generate transgenic mice expressing human integrin β8 (ITGB8). These mice were bred to mice with one functional allele of mouse itgb8 to generate an F1 generation of mice with human ITGB8 and one functional copy of mouse itgb8. These mice were cross bred to generate an F2 generation that resulted in viable BAC ITGB8, that is, itgb8−/− mice with only a human copy of the gene, demonstrating rescue of itgb8−/− lethality with human ITGB8.

These mice were used to induce airway remodeling using an intratracheal adenoviral-IL-1β delivery model. In this model, robust airway remodeling with an immunological profile similar to human chronic obstructive lung disease (COPD) is reproducibly induced.

The 37E1B5 antibody, at a dose of 7 mg/kg, significantly blocked airway inflammation, with a significant reduction in neutrophils in the bronchoalveolar lavage. Histologically, airway wall inflammation and fibrosis was significantly decreased by 37E1B5. In addition, fibroblast-specific deletion of itgb8 can significantly inhibit adenoviral-IL-1β-induced airway remodeling.

Mice with fibroblast-specific deletion of itgb8 were also used to study allergic airway remodeling (ovalbumin-induced airway inflammation, fibrosis and mucous metaplasia). Remodeling was greatly diminished in the itgb8−/− mice compared to wild type. The allergic model is also dependent on both IL-1β and TGF-β. These data show that itgb8 plays a role in the innate and adaptive immune responses mediated by IL-1β and TGF-β. IL-1β causes an increase in integrin β8 in multiple cell-types, including fibroblasts from the airway and lung, and astrocytes, and IL-1β induced β8 expression is observed in both mice and humans.

J. Example 10

Human Articular Chondrocytes Express Integrin αvβ8

Adult articular cartilage was harvested from the joint space of knee from a patient undergoing elective repair of a knee for chronic osteoarthritis. Primary chondrocytes were grown to 70% confluence and the integrin receptor expression determined by cell staining and flow cytometry. The antibodies used were anti-β8 (37E1B5), and anti-β6 (E7P6). Robust staining was detected with 37E1B5 and no staining was seen with E7P6. Primary chondrocytes were co-cultured with TMLC TGFβ reporter cells (Annes et al. (2004) *J. Cell Biol.* 165:723) in a TGFβ bioassay in the presence or absence of anti-β8 (37E1B5) or anti-β6. Anti-β8 produced a robust blockade of TGFβ activation while anti-β6 produced no such effect.

The results indicate not only that αvβ8 is expressed in chondrocytes, but that the expression results in TGFβ activation. Thus, inhibition of αvβ8 can be used to treat cartilage disorders related to activated TGFβ, such as arthritis and synovial fibrosis (see, e.g., Bakker et al. (2001) *Osteoarthritis and Cartilage* 9:128).

K. Example 11

Hepatic Stellate Cells Express αvβ8

Hepatic stellate cells are contractile cells that can produce collagen in response to activated TGFβ, and the parenchymal cell type involved in liver fibrosis. Liver fibrosis has a number of triggers, including alcohol, drugs, and anesthetics, infection (e.g., hepatitis B and C), autoimmunity, cholestasis (excess bile), and non-alcoholic steatohepatitis.

Integrin β8 expression was detected in the transgenic mice described above (human IGTB8, but not mouse igtb8) to determine whether TGFβ activity in the liver can be targeted using a β8 specific antibody described herein.

FIG. 2 shows that a significant percentage of hepatic stellate cells express β8, as determined using the 14E5 antibody.

L. Example 12

Anti-β8 Antibodies Reduce Small Bowel Inflammation

Symptoms of inflammatory bowel disease (IBD) were observed in the transgenic mice described above that express human IGTB8, but not mouse igtb8. The symptoms include weight loss and small bowel enlargement and inflammation, as well as scoliosis. FIG. 3 shows the gating of immune cells in the guts of these mice. FIG. 3A shows general gating parameters, while FIGS. 3B-3E show the expression pattern of β8 on CD4+, CD8+, B cells, and NK cells, respectively. NK cells did not express β8 at a detectable level. Dendritic cells from the guts of the IGTB8 mice also showed β8 expression.

Figure 4:
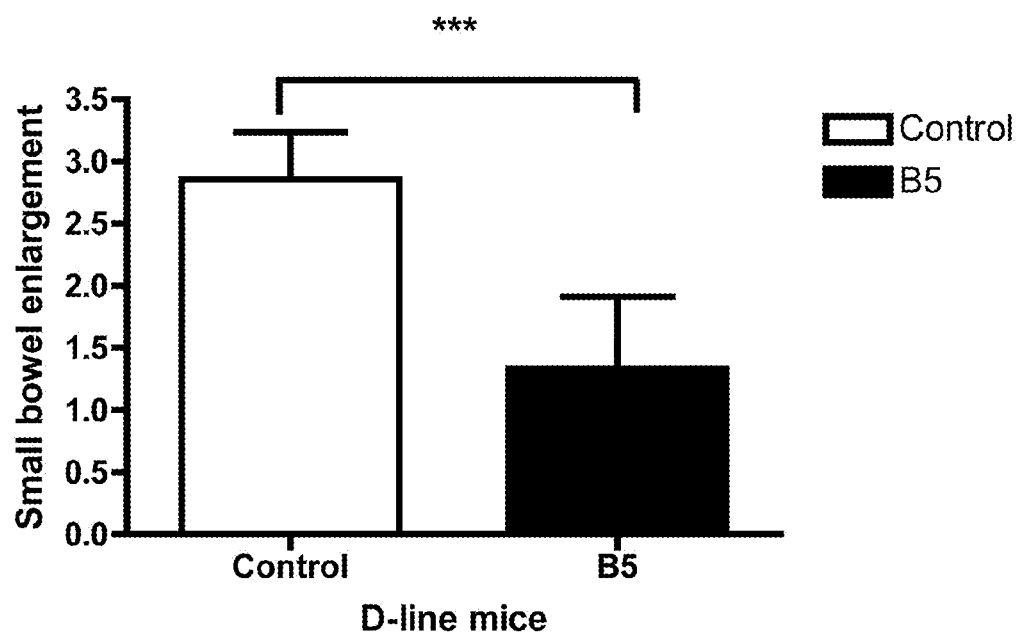
FIG. 4 shows the effect of 37E1B5 administration on the small bowel size (inflammation) in BACtg mice.
Figure 5:
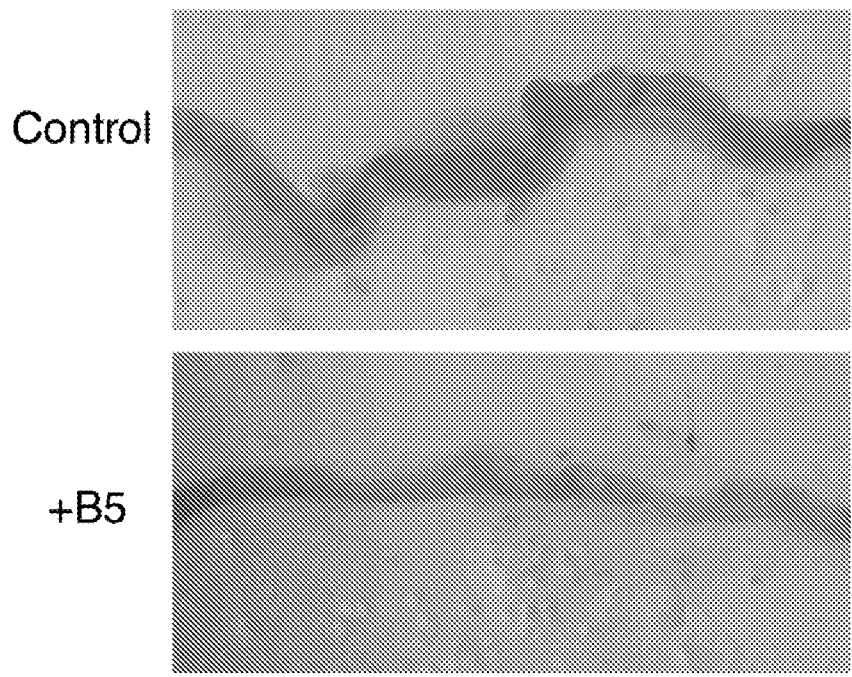
FIG. 5 shows a picture of section of small intestine of control (untreated) and 37E1B5-treated BACtg mice.

The IGTB8 mice were thus used to determine the effect of the anti-β8 antibody 37E1B5 in vivo. IGTB8 transgenic mice were treated with 3 mg 37E1B5/kg, administered IP twice per week for 8 weeks. FIG. 4 shows that treatment with the 37E1B5 antibody significantly reduced the small bowel enlargement associated with inflammation. FIG. 5 further illustrates the effect of the antibody treatment, comparing a segment of bowel taken from an IGTB8, control (untreated) mouse to that of an antibody treated (B5) mouse.

M. Example 13

4F1 and 6B9 Antibodies Bind Human β8 on Fixed Cells and Tissue

Figure 6:
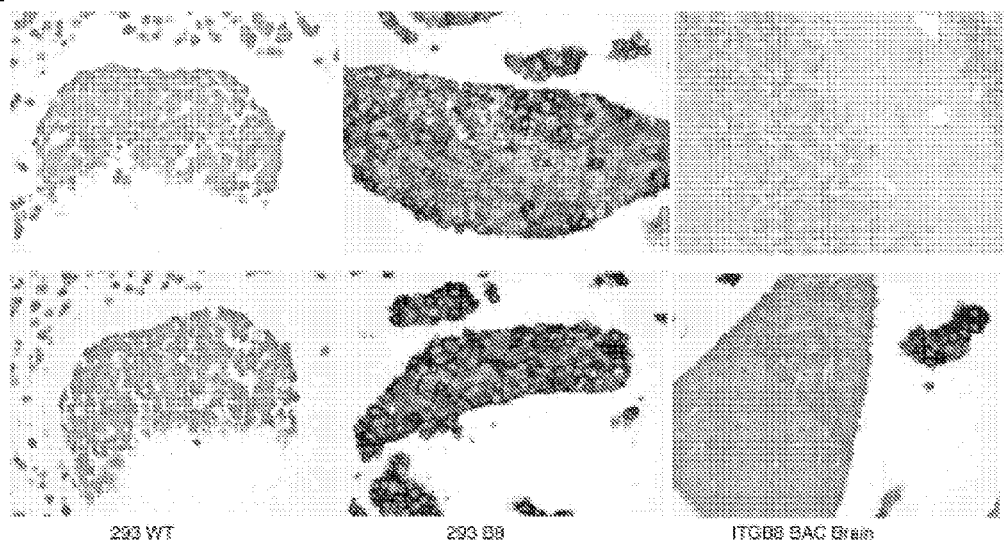
FIG. 6 shows that antibodies 4F1 and 6B9 specifically bind to and stain formalin fixed 293 cells expressing β8 (293 B8) but not non-transfected 293 cells (293 WT). The antibodies also stain formalin fixed brain sections from integrin β8 transgenic mice (ITGB8 BAC).

Hybridoma clones 4F1 and 6B9 specifically stain formalin fixed paraffin embedded 293 human embryonic kidney cells transfected with ITGB8 and brains of ITGB8 BAC transgenic (Tg) mice. Stably transfected 293 cells expressing human integrin αvβ8 (293 B8) or not (293 WT) were fixed overnight in 10% buffered formalin, pelleted, and then embedded in agarose plugs and submitted for routine tissue processing, paraffin embedding, and sectioning. Brain samples from ITGB8 BAC Tg mice were processed in a similar manner. Immunostaining was performed using antigen heat retrieval and antibodies were detected using a commercial kit (Dako). 6B9 was used at 25 ug/ml with 102C antigen heat retrieval for 10 minutes. 4F1 was used at 50-100 ug/ml with 95C antigen heat retrieval for 10 minutes. The results in FIG. 6 show that the antibodies are specific for β8, and can bind β8 on fixed tissue.

Figure 7:
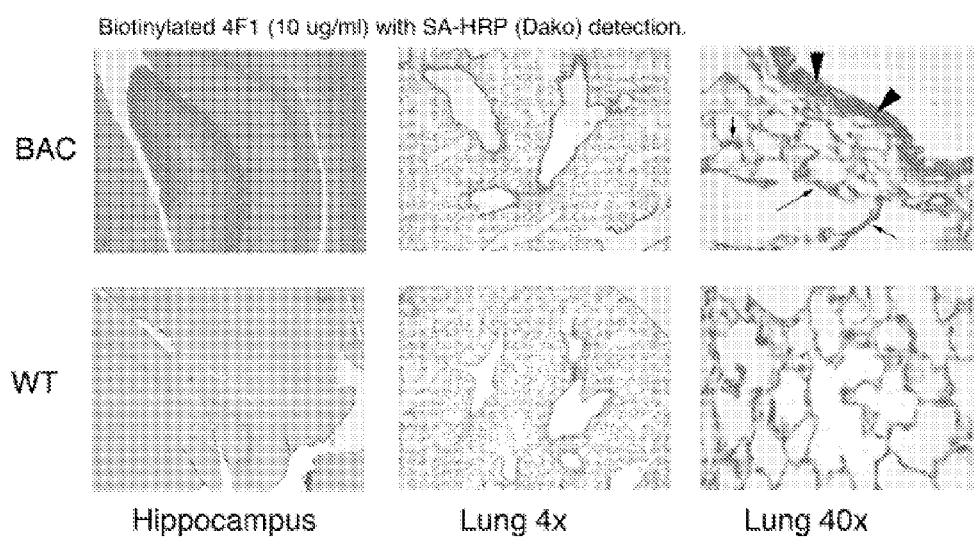
FIG. 7: Hybridoma clone 4F1 specifically stains formalin fixed paraffin embedded brains and lungs of ITGB8 BAC transgenic (Tg) mice. Brains or lungs of ITGB8 BAC Tg or wild-type (WT) mice were fixed overnight in 10% buffered formalin and submitted for tissue processing, paraffin embedding, and sectioning. Immunostaining was performed using the same antigen heat retrieval as above, and antibodies were detected using a commercial kit (Dako).

For hybridoma clone 4F1, brains or lungs of ITGB8 Tg or wild-type (WT) mice were fixed overnight in 10% buffered formalin and submitted for tissue processing, paraffin embedding, and sectioning. Immunostaining was performed using the same antigen heat retrieval as above, and antibodies were detected using a commercial kit. Results are shown in FIG. 7.

N. Example 14

Antibodies 6B9 and 4F1 can Distinguish Cells with Different Genomic Copy Numbers of β8

Figure 8:
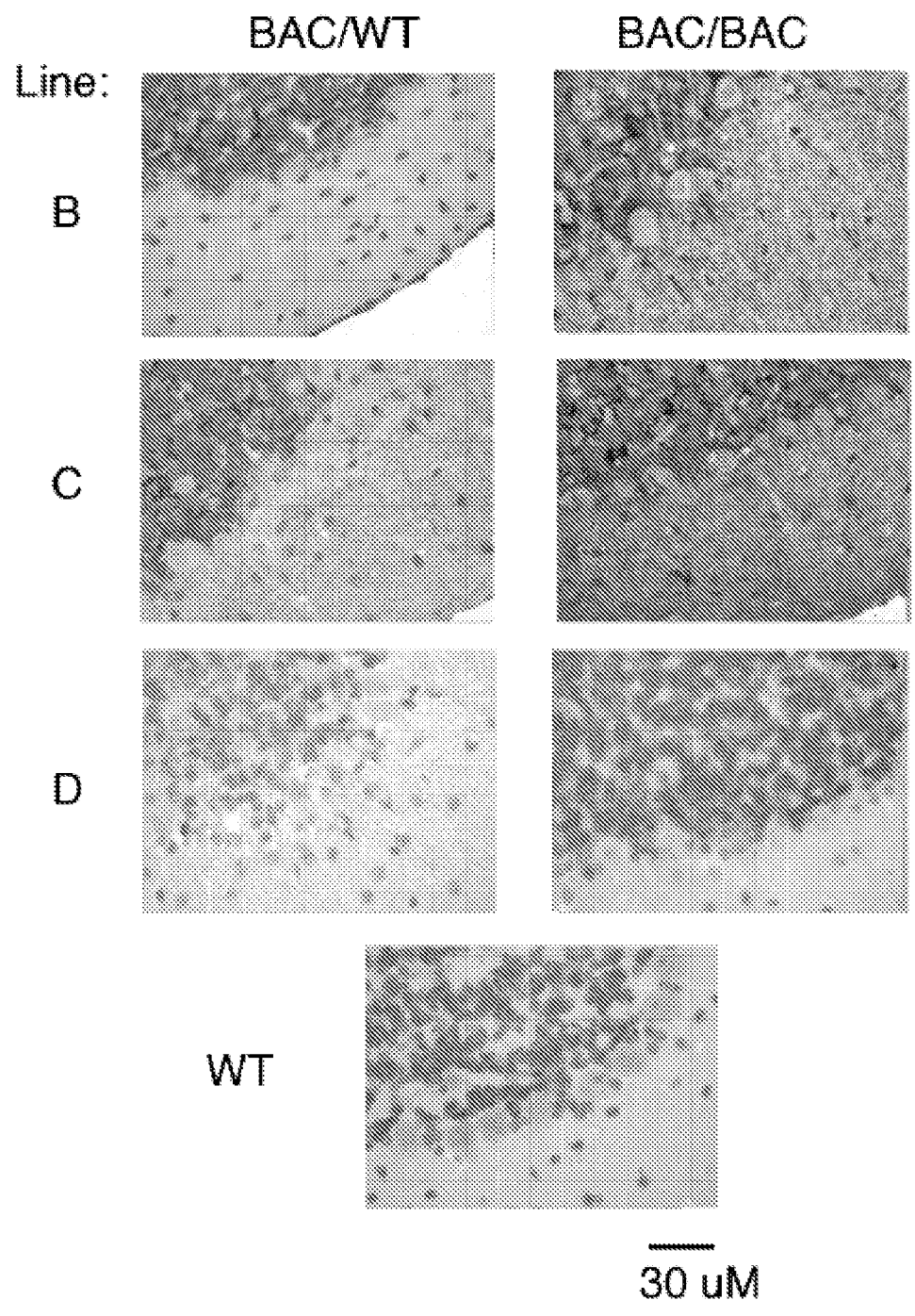
FIG. 8: Hybridoma clone 6B9 can detect copy number variation, as shown by immunostaining of formalin fixed, paraffin embedded ITGB8 BAC transgenic (Tg) mouse brain. Shown are three lines of Tg mice (B, C, and D) compared to WT (bottom panel). Copy numbers are as follows: 1 copy (D—line BAC/WT), 2 copies (B and C—line BAC/WT; D—line BAC/BAC) or 4 copies (B and C—line BAC/BAC).

Hybridoma clone 6B9 can bind to β8 on fixed tissue, and detect copy number variation. FIG. 8 shows immunostaining of formalin fixed, paraffin embedded ITGB8 BAC transgenic (Tg) mouse brain. Brains of ITGB8 BAC Tg or WT mice were fixed overnight in 10% buffered formalin and submitted for routine tissue processing, paraffin embedding, and sectioning. Immunostaining was performed as described above. Shown are three lines of Tg mice (B, C, and D) compared to WT, expressing 1 copy (D—line BAC/WT), 2 copies (B and C—line BAC/WT; D—line BAC/BAC) or 4 copies (B and C—line BAC/BAC).

Figure 9:
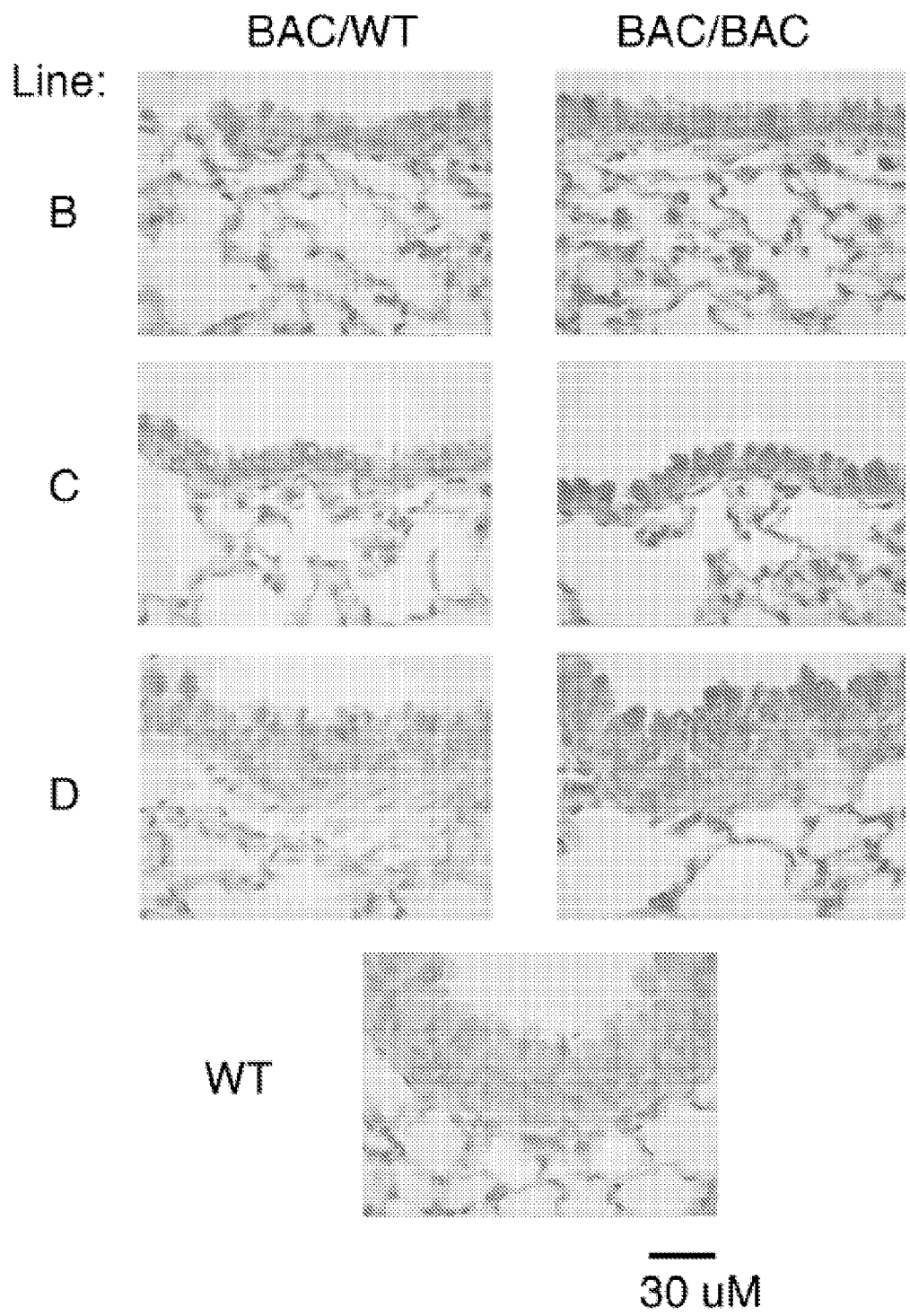
FIG. 9: Recombinant monoclonal rabbit IgG derived from the variable domains of clone 4F1 can detect copy number variation, as shown by immunostaining of formalin fixed paraffin embedded ITGB8 BAC transgenic (Tg) mouse lung. Shown are three lines of Tg mice (B, C, and D) compared to WT (bottom panel). Copy numbers are as follows: 1 copy (D—line BAC/WT), 2 copies (B and C—line BAC/WT; D—line BAC/BAC) or 4 copies (B and C—line BAC/BAC).

Similarly, a recombinant monoclonal rabbit IgG derived from the variable domains of 4F1 can detect copy number variation. FIG. 9 shows the results of immunostaining of formalin fixed paraffin embedded ITGB8 BAC transgenic (Tg) mouse lung. Lungs of ITGB8 BAC Tg or WT mice were fixed overnight in 10% buffered formalin and submitted for tissue processing, paraffin embedding, and sectioning. Immunostaining was performed as described above. Shown are three lines of Tg mice (B, C, and D) compared to WT, expressing 1 copy (D—line BAC/WT), 2 copies (B and C—line BAC/WT; D—line BAC/BAC) or 4 copies (B and C—line BAC/BAC).

Antibodies 4F1 and 6B9 can detect differences in expression between one and two copies of ITGB8 in formalin fixed paraffin embedded tissues isolated from BAC ITGB8 mice. These antibodies are thus potentially useful as diagnostic agents to detect increased expression of b8, as companion diagnostics to therapeutic antibodies (e.g., 37E1B5, 11E8 and b8-binding fragments and affinity matured variants thereof).

O. Example 15

Detection of β8 on Fixed, Human Pathological Lung Tissue

Figure 10:
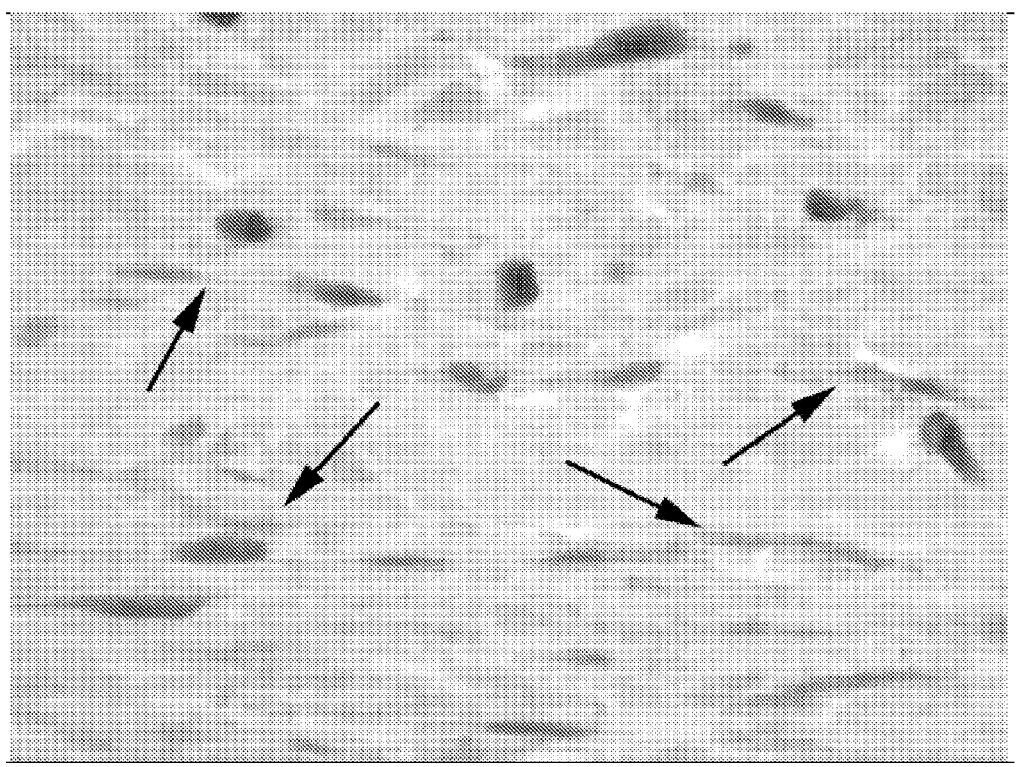
FIG. 10: Recombinant monoclonal rabbit IgG derived from the variable domains of clone 4F1 can detect αvβ8 expression by immunostaining of formalin fixed paraffin embedded human fibrotic lung. Arrows indicate staining of spindle cells, representing fibroblasts embedded in dense fibrous connective tissue.

Recombinant monoclonal rabbit IgG derived from the variable domains of clone 4F1 can detect αvβ8 expression by immunostaining of formalin fixed paraffin embedded human fibrotic lung. Human lung specimens were obtained from surgical pathology tissue from a patient with emphysema and subpleural scarring. The tissue was fixed overnight in 10% buffered formalin and submitted for tissue processing, paraffin embedding, and sectioning. Immunostaining was performed as described above. Results are shown in FIG. 10. Arrows indicate staining of spindle cells, representing fibroblasts embedded in dense fibrous connective tissue.

P. Example 16

Epitope Mapping for 6B9 and 4F1 Antibodies

Chimeric integrin β8 constructs, which swapped mouse sequences into human ITGB8 were used to localize the binding epitopes for the 6B9 and 4F1 antibodies. The epitope was localized by antibody binding, cell surface staining, and detection by flow cytometry. The epitope is encompassed within amino acids 61-105 of human integrin β8. The 6B9 and 4F1 antibodies bind to human, but not to mouse β8. At least one of the 3 non-conservative amino acid differences or 2 minor amino acid differences (indicated by + in the alignment sequence) are included in the binding epitope, or affect the 3-dimensional structure of the domain in such a way as to distinguish the mouse from the human protein.

```
                                              (SEQ ID NO: 15)
Mouse  61  LGPECGWCVQEDFVSGGSGSERCDTVSSLISKGCPVDSIEYLSVH    105

(SEQ ID NO: 16)
           LGPECGWCVQEDF+SGGS SERCD VS+LISKGC VDSIEY SVH (SEQ ID NO: 14)
Human  61  LGPECGWCVQEDFISGGSRSERCDIVSNLISKGCSVDSIEYPSVH    105
```

SEQ ID NO:14 represents the region of human integrin β8 that includes the epitope (amino acids 61-105). SEQ ID NO:15 represents the homologous murine sequence, which is not bound by the 4F1 or 6B9 antibodies. The alignment sequence is represented by SEQ ID NO:16.

Amino acid swapping in this region was carried out to determine which amino acid(s) are included in the β8 epitope. The table below indicates that the serine residue at position 95 of the human β8 sequence is involved in the 6B9 and 4F1 epitopes.

|  |  | % Positive 4F1 | % Positive 6B9 |
|---|---|---|---|
| Mouse | V G T S P (SEQ ID NO: 122) | 3 | 6 |
| Human | I R I N S (SEQ ID NO: 123) | 100 | 100 |
|  | V R I N S (SEQ ID NO: 124) | 92 | 102 |
|  | I G I N P (SEQ ID NO: 125) | 0 | 1 |
|  | I G I N S (SEQ ID NO: 126) | 101 | 104 |

Q. Example 17

Characterization of 6B9 and 4F1 Antibodies

The variable region sequences for 6B9 were obtained, as shown in SEQ ID NOs:18 and 19. CDRs 1-3 of the 6B9 heavy chain are: DYLIE, VINPETGGTNYNAKFKG, and EAGNYIYAMDY, SEQ ID NOs:40-42, respectively. CDRs 1-3 of the 6B9 light chain are: RASVNIYSYLV, NAKTLAE, and QHHHGTPYT, SEQ ID NOs:43-45, respectively.

The variable region sequences for 4F1 were obtained, as shown in SEQ ID NOs:20 and 21. CDRs 1-3 of the 4F1 heavy chain are: NYLIE, VINPGTGGTNYNKKFKV, and EGNARTYYYAMDY, SEQ ID NOs:116-118, respectively. CDRs 1-3 of the 4F1 light chain are: RASENIYSYLV, NAKTLAE, and QHHNGTPYT, SEQ ID NOs:119-121, respectively.

R. Example 18

Characterization of 37E1B5, 14E5, and 11E8 Antibody Epitopes

As shown above, SEQ ID NO:1 represents the region of human integrin β8 that includes the β8 epitope (amino acids 120-180) for the 37E1B5, 14E5, and 11E8 antibodies. SEQ ID NO:2 represents the homologous murine sequence, which is not significantly bound.

Amino acid swapping in this region was carried out to determine which amino acid(s) are included in the β8 epitope. The table below indicates which of amino acids 175-180 of SEQ ID NO:1 are included in the epitope for each antibody.

|  | 37E1B5 % positive | 14E5 % positive | 11E8 % positive |
|---|---|---|---|
| RKMAFF (human) SEQ ID NO: 127 | 108 | 112 | 97 |
| KKMALY (mouse) SEQ ID NO: 128 | 0 | 0 | 0 |
| RKMALY SEQ ID NO: 129 | 14 | 1 | 4 |
| RKMAFY SEQ ID NO: 130 | 89 | 6 | 108 |
| KKMAFY SEQ ID NO: 131 | 3 | 6 | 31 |
| KKMALF SEQ ID NO: 132 | 31 | 1 | 3 |
| KKMAFF SEQ ID NO: 133 | 116 | 9 | 115 |
| RKMALF SEQ ID NO: 134 | 131 | 150 | 125 |

S. Example 19

Affinity Determination for Single Chain Fv Antibodies

We also determined the affinity of the disclosed antibodies, including affinity matured versions. Typically, the affinity Kd of a single chain antibody is 10-100 fold higher than that of the corresponding Ig (i.e., the single chain antibody has 10-100 fold lower affinity than the corresponding Ig).

| Antibody | Kd (nM) of scFv |
|---|---|
| 4F1 | >100 |
| 6B9 | 14.83 |

| Antibody | Kd (nM) of scFv |
|---|---|
| 6B9Mut1 | 9.34 |
| 11E8 | >250 |
| 11E8Mut28 | 3.52 |
| 11E8Mut94 | 3.2 |
| 11E8Mut39 | 21.07 |
| 14E5 | 13.96 |
| 14E5Mut11 | 3.85 |
| 14E5Mut42 | 3.35 |
| 14E5Mut54 | 2.09 |
| 14E5Mut65 | 3.04 |
| 14E5Mut68 | 1.42 |
| 14E5Mut83 | 1.79 |
| 14E5Mut93 | 2.31 |
| 14E5Mut95 | 1.83 |

The examples and embodiments described herein are for illustrative purposes only and that various modifications or changes in light thereof will be suggested to persons skilled in the art and are to be included within the spirit and purview of this application and scope of the appended claims. All publications, websites, accession numbers, patents, and patent applications cited herein are hereby incorporated by reference in their entireties for all purposes.

What is claimed is:

1. An isolated antibody that specifically binds αvβ8, wherein the antibody has a heavy chain variable region comprising SEQ ID NO:8 and a light chain variable region comprising SEQ ID NO:9.

2. The isolated or humanized antibody of claim 1, wherein the antibody is an scFv antibody.

3. The isolated antibody of claim 1 linked to a detectable label.

4. The isolated antibody of claim 1, wherein the isolated antibody is humanized.

5. A pharmaceutical composition comprising the isolated antibody of claim 1 in a pharmaceutically acceptable excipient.

6. A method of reducing TGFβ signaling in an individual, comprising administering the pharmaceutical composition of claim 5 to the individual, thereby reducing TGFβ signaling in the individual.

7. The method of claim 6, wherein the individual has at least one condition selected from the group consisting of inflammatory bowel disease (IBD), chronic obstructive pulmonary disease (COPD), asthma, and a pulmonary fibrotic disorder, and wherein reducing TGFβ signaling results in amelioration of the condition.

8. A method of detecting αvβ8 in a cell from an individual, comprising
    contacting the cell from the individual with the isolated antibody of claim 1, and
    detecting binding of the isolated antibody to the cell.

9. The method of claim 8, wherein the cells are fibroblasts, chondrocytes, or hepatic stellate cells.

* * * * *